(12) United States Patent
Ramana et al.

(10) Patent No.: US 9,890,132 B2
(45) Date of Patent: Feb. 13, 2018

(54) PROCESS FOR THE PREPARATION OF ANTI-INFLAMMATORY AROYLBENZOFURAN COMPOUNDS

(71) Applicant: COUNCIL OF SCIENTIFIC AND INDUSTRIAL RESEARCH, New Delhi (IN)

(72) Inventors: Chepuri Venkata Ramana, Pune (IN); Yadagiri Kommagalla, Pune (IN); Kolluru Srinivas, Pune (IN)

(73) Assignee: COUNCIL OF SCIENTIFIC & INDUSTRIAL RESEARCH, New Delhi (IN)

( * ) Notice: Subject to any disclaimer, the term of this patent is extended or adjusted under 35 U.S.C. 154(b) by 0 days.

(21) Appl. No.: 14/914,378

(22) PCT Filed: Aug. 25, 2014

(86) PCT No.: PCT/IN2014/000546
§ 371 (c)(1),
(2) Date: Feb. 25, 2016

(87) PCT Pub. No.: WO2015/029062
PCT Pub. Date: Mar. 5, 2015

(65) Prior Publication Data
US 2016/0229827 A1    Aug. 11, 2016

(30) Foreign Application Priority Data
Aug. 25, 2013  (IN) ............................ 1876/DEL/2013

(51) Int. Cl.
C07D 307/80  (2006.01)
(52) U.S. Cl.
CPC .................................. C07D 307/80 (2013.01)
(58) Field of Classification Search
None
See application file for complete search history.

(56) References Cited
U.S. PATENT DOCUMENTS 6,869,972 B2   3/2005  Druzgala
7,498,449 B2   3/2009  Druzgala et al.

FOREIGN PATENT DOCUMENTS

EP        0623607 B1    7/1998
WO       03/050102 A2   6/2003
WO      2007011835 A2   1/2007

OTHER PUBLICATIONS

Hiroki Takakata, et al., "Cycloadditions to Ketene-S, N-Acetals, New Syntheses of Benzo[b]- and Naphtho(1, 2-b) Furans, 1-Benz- and Naphth (1, 2-b)Oxepinins, and Benz(b)Furan-2-Ones," Chemistry Letters, 5-6, 1986.
(Continued)

Primary Examiner — Heidi Reese
(74) Attorney, Agent, or Firm — Abelman, Frayne & Schwab

(57) ABSTRACT

Disclosed herein an efficient process for synthesis of benzofuran analogs having anti-inflammatory activity which comprises, Ru-catalyzed branched and linear selective alkylation of aroylbenzofurans formula-I with alpha, beta unsaturated esters of formula-II via C—H activation in presence of base, additives and organic solvent at suitable temperature to give high yield of desired linear alkylated benzofuran compounds of formula-III or branched alkylated benzofuran compounds of formula-IV or mixture thereof.

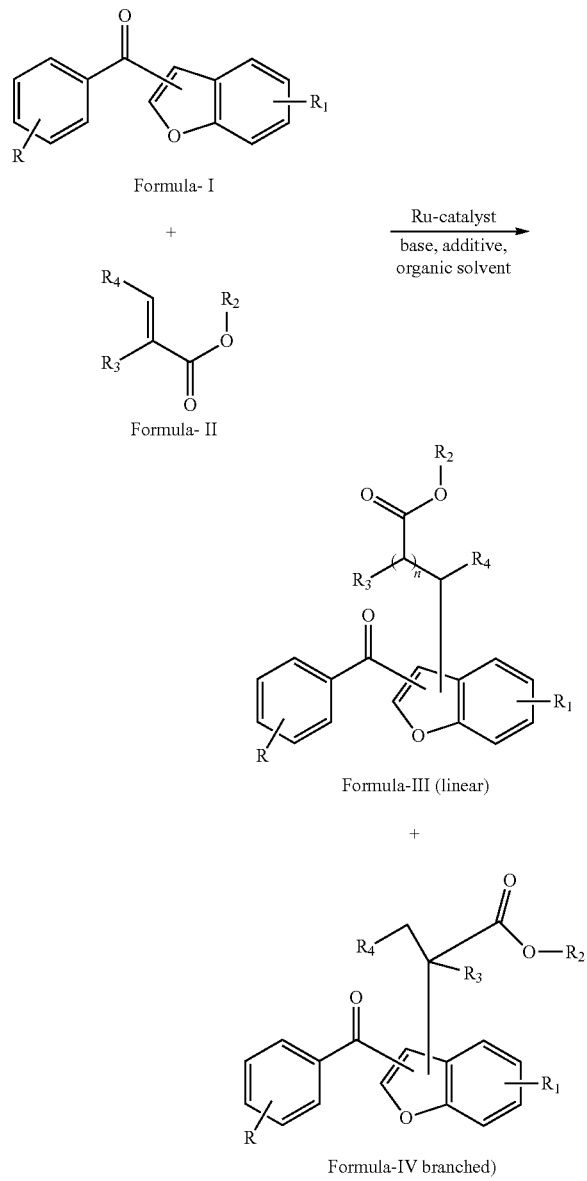

22 Claims, No Drawings

(56) References Cited

OTHER PUBLICATIONS

Daleep Singh Deorha, et al., Notiz uber eine modifizierte Synthase einiger B-[Benzofuryl-(2)]-propionauren, Jahrg. 99, 2063-2064 (1966).

Vincent Ritleng, et al., "Ru-, Rh-, and Pd-Catalyzed C—C Bond Formation Involving C—H Activation and Addition on Unsaturated SUbstrates: Reactions and Mechanistic Aspects," Chem. Rev. 102:1731-1769 (2002).

Backer Sundararaju, et al., "sp3 C—H Bond Activation with Ruthenium(II) Catalysts and C(3)-Alkylation of Cyclic Amines,k" Journal of the American Chemical Society, 133:10340-10343 (2011).

PROCESS FOR THE PREPARATION OF ANTI-INFLAMMATORY AROYLBENZOFURAN COMPOUNDS

FIELD OF THE INVENTION

The present invention relates to a simple process for the preparation of anti-inflammatory compounds. Particularly, the invention provides Ru-catalyzed process for regioselective alkylation of aroylbenzofurans with alpha, beta unsaturated esters via C—H activation in suitable reaction conditions; more particularly the invention provides C3 alkylation of 2-aroylbenzofurans and C2 alkylation of 3-aroylbenzofurans with acrylates via C—H activation in presence of base, additive and organic solvent at high temperature to give high yield of desired alkylated benzofuran products having anti-inflammatory activity.

BACKGROUND AND PRIOR ART

The transition metal catalyzed carbo-carbon and carbon-hetero atom bond formations via the activation of $SP^2/SP^3$ C—H bonds has been recognized as a powerful alternative to the classical cross-coupling reactions involving the pre-functionalized coupling partners. The direct and directed C—H addition of heterocycles to olefins has been extensively investigated by employing various transition metal complexes. In general, these reactions preferentially provide the linear adducts. In rare cases, such as styrene when employed as an olefin counterpart, the branched selective hydroarylation has been documented. Coming to the olefins conjugated with an electron withdrawing group such as acrylates, depending upon the conditions employed, the directed cross dehydrative couplings lead either to alkylation or alkenylation or both in a linear fashion. Surprisingly, with acrylates and related derivatives, there were no reports where the formation of substantial amounts of branched adducts had been noticed.

WO 2007011835 discloses benzofuranyl compounds and hydrates, solvates, salts thereof obtained from pyranobenzofuran.

EP0623607B1 discloses benzofuranyl-and-thiophenyl-alkanecarboxyclic acid derivatives and process for preparation thereof.

Scheme 1. Selected APIs/NCEs having the 2,3-disubtituted benzofuran core

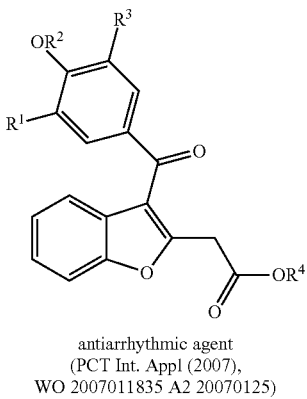

antiarrhythmic agent
(PCT Int. Appl (2007),
WO 2007011835 A2 20070125)

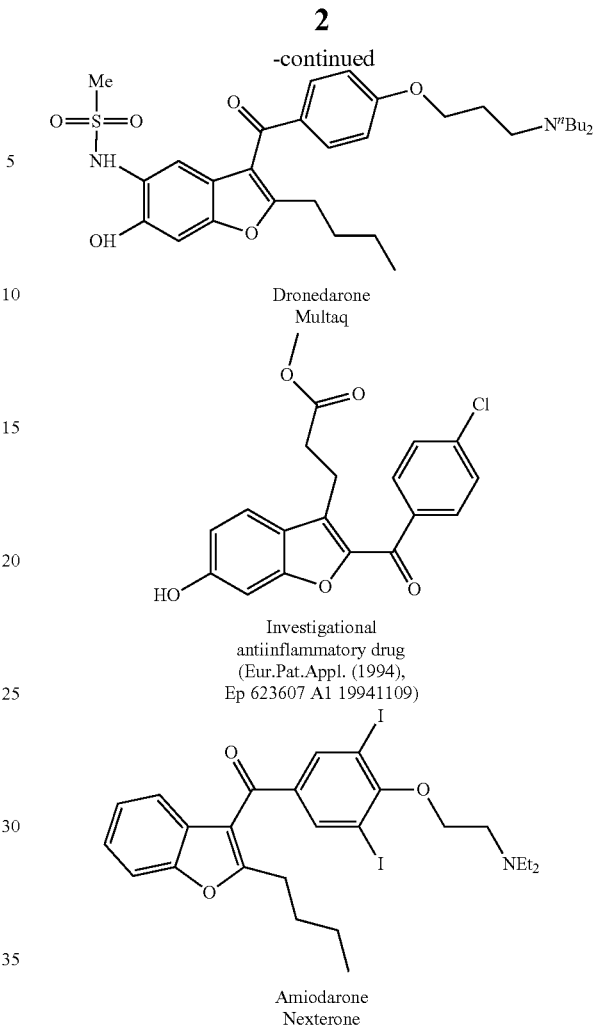

Dronedarone
Multaq

Investigational
antiinflammatory drug
(Eur.Pat.Appl. (1994),
Ep 623607 A1 19941109)

Amiodarone
Nexterone

The benzofuran is an important structural unit present in a variety of natural products and received significant recent interest in the development of new pharmaceuticals. The 2,3-disubstituted benzofurans deserves a special mention as they served as building blocks for a number of natural products synthesis and possess unique biological activities. For example, 3-(2-aroylbenzofuran-3-yl)propanoates and their regiomeric counterparts—the 2-(3-aroylbenzofuran-2-yl)propanoates have been identified as novel anti-inflammatory agents. The former compounds are known to inhibit the type IV phosphodiesterase which results in the elevation of cellular cAMP that regulate the production of superoxide by polymorphonuclear leukocytes (PMN). The reported procedure far the synthesis of these compounds is multistep in nature and involves harsh reaction conditions such as Fridel-Crafts acylation and acid/base mediated condensations. A plausible approach will be the one-pot sequential metal-catalyzed cyclization of 2-alkynylphenols followed by the trapping of the intermediate aryl metal species with α,β-unsaturated carbonyl compounds. The second step can be conducted either in an oxidative fashion leading to C3 alkenylation products or under a redox neutral process to access the C3-alkylated derivatives.

WO2013014480, WO2003050102 and WO2007011835 described the use of aroyl benzofuran compounds as anti-inflammatory agents.

In 2011, T. Satoh, et al. reported ruthenium-catalyzed oxidative vinylation of heteroarene carboxylic acids with alkenes via regioselective C—H bond cleavage in *org. lett.* 2011, 13, 706-708. The method involves the C2 carboxylate directed cross-dehydrogenative coupling of alkyl acrylates and benzo[b]furan-2carboxylate derivatives. The cheap and inexpensive [RuCl$_2$(p-cymene)]$_2$ has been employed as the catalyst and Cu(OAc)$_2$.H$_2$O as the stoichiometric oxidant. The reactions proceeded with complete linear selective alkenylation. The applicability of this ruthenium (II)-mediated cross dehydrogenative couplings has been explored further by several other groups employing a wide range of directing groups on both aryl and heteroaryl rings.

Very recently, a palladium-catalyzed C3 direct arylation of 2-substituted benzo[b]furans with aryl bromides has been reported by Bertounesque and co-workers (*J. Org. Chem.*, 2012, 77 (3), pp 1316-1327).

Shibata and co-workers (*J Am Chem Soc*. 2012 Oct. 24; 134(42): 17474-7) reported the cationic iridium-catalyzed C2-alkylation of N-substituted indole derivatives using alkenes and acrylates. In case of alkenes, the regioselectivity can be tuned towards linear or branched alkylation by selecting an appropriate N-protecting group.

Vincent Ritleng et al. in Chem. Rev. 2002, 102, 1731-1769 discloses Ru-, Rh-, and Pd-catalyzed C—C bond formation which involves C—H activation and addition on unsaturated substrates, it further describes reactions of furans with acrylates in the presence of the Pd(OAc)$_2$-Cu (OAc)$_2$ catalyst system, in presence of tertbutyl perbenzoate as oxidant.

Ruthenium-catalyzed ortho-C—H bond alkylation of aromatic amides with α,β-unsaturated ketones is disclosed by Guy Rouquet et al *Chem. Sci.*, 2013, 4, 2201-2208, whereas Dr. James w. Walton et al in Angewandte Chemie International Edition 51(49), 12166-12168, 2012 describes ruthenium-Catalyzed ortho-alkylation of phenols with alcohols by dehydrative coupling.

Despite its widespread application in dehydrogenative couplings, surprisingly, the Ru-catalyzed regioselective alkylation with acrylates via C—H activation has not yet been documented. Therefore industrially viable, technically advanced process for regioselective alkylation of benzofuran compounds in suitable catalyst involving C—H activation is desirable to obtain biologically active benzofurane derivatives.

OBJECTIVE OF THE INVENTION

The main object of the present invention is to provide a simple process for the preparation of anti-inflammatory compounds.

One more object of the present invention is to provide an efficient, simple, high yielding process for the synthesis of novel benzofuran derivatives via [Ru]-catalysed C—H activation and their uses thereof.

SUMMARY OF THE INVENTION

The present invention provides an efficient, simple, high yielding process for the synthesis of novel, benzofuran analogues/derivatives, which comprises [Ru]-catalyzed regioselective alkylation of aryoylbenzofurans of formula-I with alpha beta unsaturated esters of formula-II via C—H activation in presence of base, additives and organic solvent at suitable temperature to obtain linear alkylated aroylbenzofuran of formula-III or branched alkylated aroylbenzofuran of formula-IV or mixtures thereof.

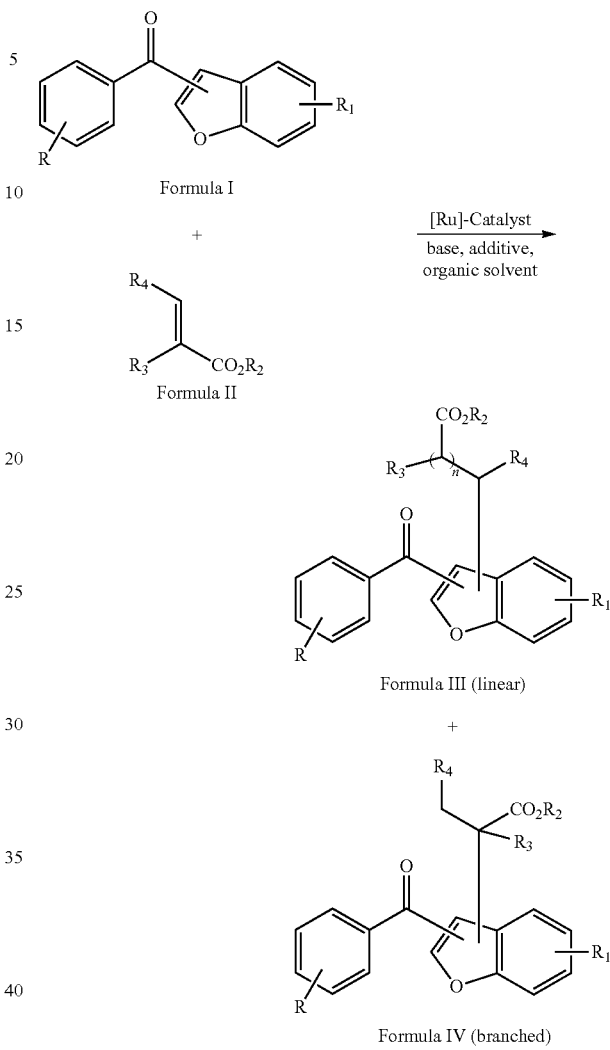

wherein n is an integer ranges from 1 to 6;
R and R$_1$ are independently selected from the group consisting of hydrogen, halogen, (C$_1$-C$_6$) alkyl; (C$_1$-C$_5$) alkoxy; —COR$_5$, where R$_5$ is (C$_1$-C$_6$) alkyl, aryl or alkylaryl;
R$_2$ is hydrogen, halogen, linear or branched (C$_1$-C$_6$) alkyl, (C$_1$-C$_5$) alkoxy, cyclo (C$_4$-C$_8$) alkyl;
R$_3$ is hydrogen, (C$_1$-C$_6$) alkyl; and
R$_4$ is hydrogen, (C$_1$-C$_6$) alkyl, halogen, cycloalkyl, aryl, alkylaryl.

Particularly, the invention provides an efficient process for synthesis of benzofuran analogues, which comprises, Ru-catalyzed branched and linear selective C3 alkylation of 2-aroylbenzofurans and C2 alkylation of 3-aroylbenzofurans with alpha, beta unsaturated esters via C—H activation in presence of base, additives and organic solvent at suitable temperature to give high yield of desired branched/linear alkylated benzofuran compounds.

In another aspect, the invention provides carbonyl directed C3-H activation and selective alkylation of 2-aroylbenzo[b]furans with acrylates either in linear or branched-fashion depending upon the Ru-catalyst employed, wherein linear alkylation is assisted by [Ru(p-cymene)Cl$_2$]$_2$ and branched alkylation is carried out in presence of [Ru(PPh$_3$)$_3$Cl$_2$] in suitable base and organic solvent at elevated temperature (as described in Scheme 2).

Scheme 2

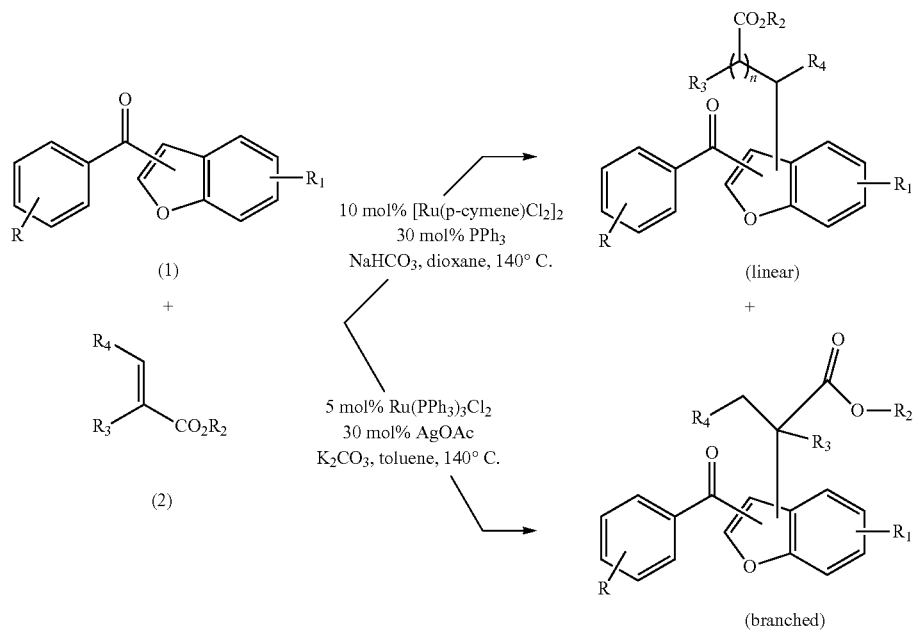

(substituents are same as described herein above)

In yet another aspect, the invention provides ruthenium (II) catalyzed branched and linear selective alkylation of the 3-aroyl benzofuran derivatives at the C2 position by employing acrylate derivatives (alpha beta unsaturated ester) to obtain desired C2 alkylated benzofuran compounds having anti-inflammatory activity, wherein alkylation is carried out in presence of [Ru(PPh$_3$)$_3$Cl$_2$] in suitable base and organic solvent at elevated temperature (as described in Scheme 3).

Scheme 3:

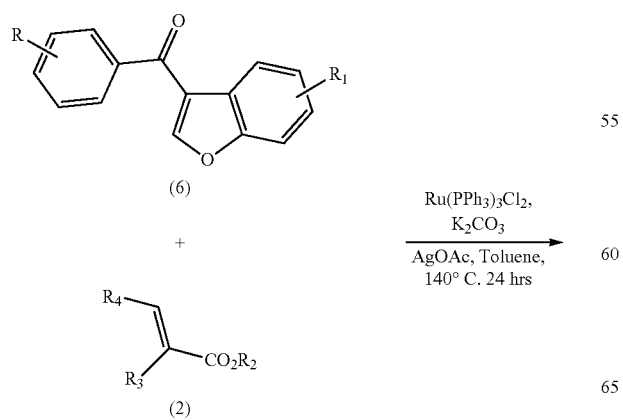

-continued

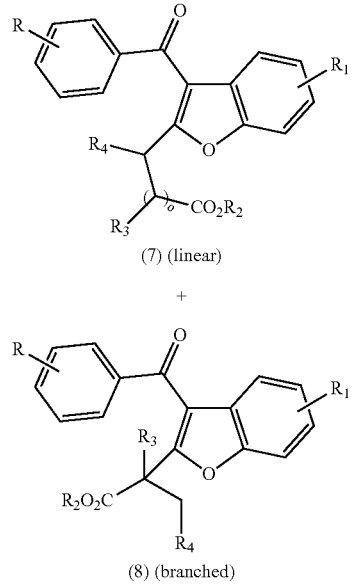

(substituents are same as described above)

In further aspect, the invention provides pharmaceutical composition comprising effective amount of synthesized alkylated aroylbenzofuran analogues along with pharmaceutically acceptable excipients or vehicles or carriers or inactive ingredients for treatment of inflammatory diseases.

DETAILED DESCRIPTION OF THE INVENTION

The invention will now be described in detail in connection with certain preferred and optional embodiments, so that various aspects thereof may be more fully understood and appreciated.

The present invention provides an efficient, simple, high yielding process for the synthesis of novel, benzofuran analogues/derivatives comprising [Ru]-catalyzed selective alkylation of aroylbenzofurans with alpha beta unsaturated esters via C—H activation.

In preferred embodiment the present invention provides an efficient, simple, high yielding process for the synthesis of novel, benzofuran analogues/derivatives comprising [Ru]-catalyzed regioselective alkylation of aroyoylbenzofurans of formula-I with alpha beta unsaturated esters of formula-II via C—H activation, in presence of base, additives and organic solvent at suitable temperature to obtain linear alkylated aroylbenzofuran of formula-III and branched alkylated aroylbenzofuran of formula-IV.

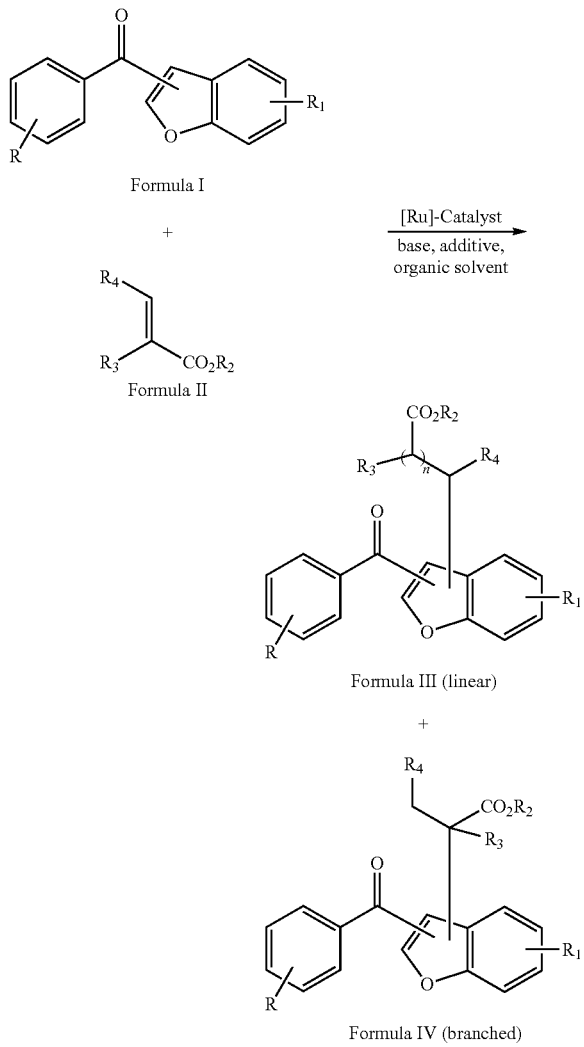

wherein 'n' is an integer ranges from 1 to 6;
R and $R_1$ are independently selected from the group consisting of hydrogen, halogen, $(C_1-C_6)$ alkyl; $(C_1-C_5)$ alkoxy; —$COR_5$, where $R_5$ is $(C_1-C_6)$ alkyl, aryl or alkylaryl;
$R_2$ is hydrogen, halogen, linear or branched $(C_1-C_6)$ alkyl, $(C_1-C_5)$ alkoxy, cyclo $(C_4-C_8)$ alkyl;
$R_3$ is hydrogen, $(C_1-C_6)$ alkyl; and
$R_4$ is hydrogen, $(C_1-C_6)$ alkyl, halogen, cycloalkyl, aryl, alkylaryl.

In another embodiment, the alpha beta unsaturated esters are preferably acrylate derivatives having formula (2).

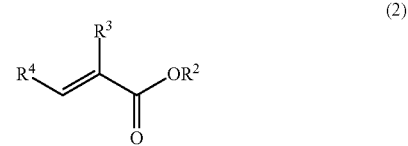

$R_2$ is hydrogen, halogen, linear or branched $(C_1-C_6)$ alkyl, $(C_1-C_5)$ alkoxy, cyclo $(C_4-C_8)$ alkyl;
$R_3$ is hydrogen, $(C_1-C_6)$ alkyl; and
$R_4$ is hydrogen, $(C_1-C_6)$ alkyl, halogen, cycloalkyl, aryl, alkylaryl.

Accordingly the acrylate substrate scope for coupling partners selected from the group consisting of α,β-unsaturated esters, acrylonitrile and acrylamide as depicted in Table 1.

According to the embodiment, the acrylate derivatives of formula-II are selected from the group consisting of linear or branched $(C_1-C_6)$ alkyl acrylates, cyclo $(C_4-C_8)$ alkyl acrylates, $(C_1-C_6)$ alkyl methacrylates, $(C_1-C_6)$ alkyl cinnamate, linear or branched $(C_1-C_6)$ alkyl crotonate, substituted or unsubstituted acrylamide.

Preferably acrylate derivatives are selected from methyl acrylates, ethyl acrylates, n-butyl acrylates, terbutyl acrylates, cyclohexyl acrylates, methyl methacrylate, butyl methacrylate, methyl crotonate, ethyl cinnamate, N-isopropylacrylamide.

The compound of formula-II hereinafter also referred as (2).

In another preferred embodiment the ruthenium complexes are selected from $Ru_3(CO)_{12}$, $RuH_2(CO)(PPh_3)_3$ and $Ru(PPh_3)_3Cl_2$, $[Ru(p\text{-cymene})Cl_2]_2$ ($PPh_3$); wherein the catalyst for best branched selectivity is $Ru_3(CO)_{12}$ and for good yields is $Ru(PPh_3)_3Cl_2$ complex and for linear selectivity $[Ru(p\text{-cymene})Cl_2]_2$ is employed.

The base employed in the process is preferably $K_2CO_3$ and $NaHCO_3$ with concentration 1 to 6 equv.

In yet another preferred embodiment, the additive is selected from the group consisting of adamantane-1-carboxylic acid ($AdCO_2H$), $PivCO_2H$, $CCl_3CO_2H$, $Cu(OAc)_2$, $MesCO_2H$, $Ag(OAc)$; preferably the additive is silver acetate $Ag(OAc)$.

In another embodiment, the present invention provides a process which optionally carried out in presence of additive with a high increase in the amount of intractable compounds mixture.

In another preferred embodiment, the process is carried out in organic solvent selected from 1,4-dioxane or toluene.

The temperature is maintained in the range of 120° C.-160°; preferably 130° to 150° C.

In another embodiment, the aroylbenzofuran of formula-I is selected from the group consisting of 2-aroylbenzofuran (1) and 3-aroylbenzofuran (6); where the Ru catalyzed selective alkylation of 2-aroylbenzofuran (1) takes place at C3-position under optimized reaction condition to obtain branched or linear alkylated benzofuran product (3) and (4) respectively and for 3-aroylbenzofuran (6) the C—H bond formation by alkylation is occurred at C2-position under suitable reaction condition to obtain desired branched or linear alkylated benzofuran product (7) and (8).

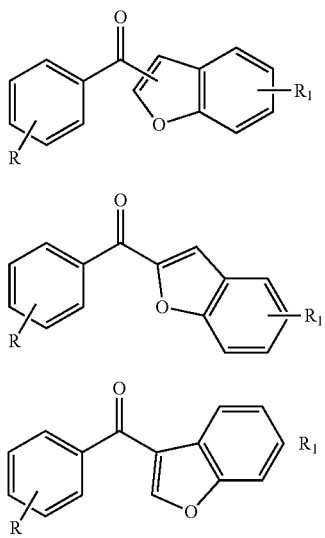

substituents are described herein above

In another embodiment the present invention provides a process for the preparation of 2-aroyl benzofurans from the corresponding substituted acetophenones and salicylaldehyde in acetone under reflux conditions (cf scheme 4).

Scheme 4:

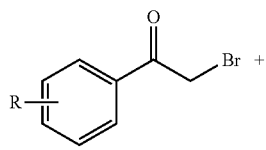

In another preferred embodiment, the present invention provides to Ru-catalyzed process for branched or linear selective C3 alkylation 2-aroylbenzofurans (1) and C2 alkylation of 3-aroylbenzofurans (6) with alpha-beta unsaturated esters (2) via C—H activation in suitable reaction condition to give high yield of desired alkylated benzofuran products of formula-III and IV having anti-inflammatory activity.

In preferred embodiment, the invention provides a process for synthesis of linear or branched C3-alkylated benzofuran products (3) and (4) comprising the steps of:

a) Adding 2-aroylbenzofuran compound (1), alpha beta unsaturated ester (2), base and organic solvent to a reaction vessel containing a mixture of Ru-complex and additive under argon atmosphere to get a solution mixture; and b) Stirring the solution mixture (a) at a temperature in the range of 130 to 150° C., for time in the range of 30 to 40 hrs followed by cooling the solution mixture and work-up afforded the crude products, which is further purified by column chromatography to obtain pure branched (3) or linear (4) alkylated products or mixtures thereof in good yields.

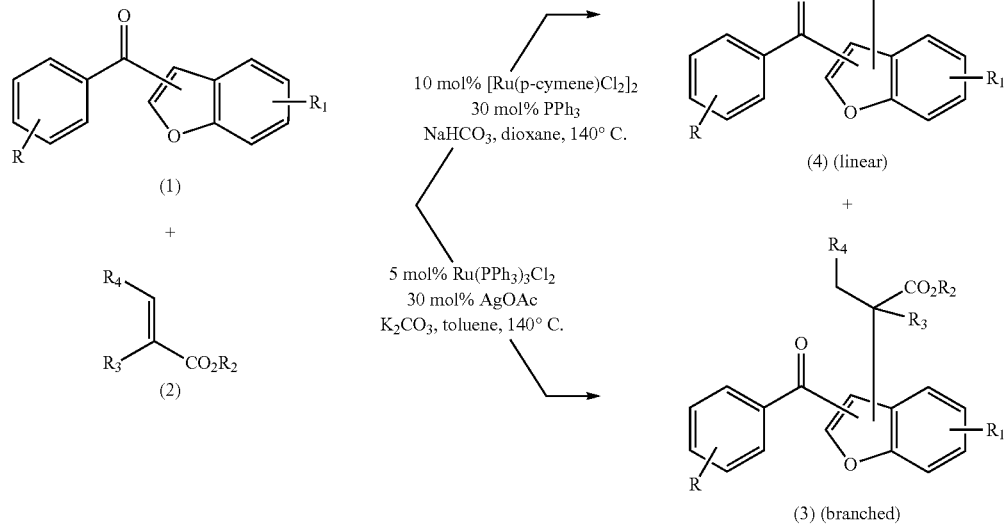

(substituents are same as described herein above)

In another preferred embodiment, the invention provides a process for the synthesis of branched C3-alkylated benzofuran compounds of formula (3), comprising the steps of:

a. Adding 2-aroylbenzofuran (1), acrylate (2), $K_2CO_3$ and toluene to a reaction vessel containing a mixture of $[Ru(PPh_3)_3Cl_2]$, AgOAc under argon atmosphere to get a solution mixture;

b. Stirring the solution mixture at a temperature in the range of 130 to 150° C., for time in the range of 20 to 30 hrs followed by cooling the solution mixture and work-up afforded the crude products which is further purified by column chromatography to obtain pure branched alkylated benzofuran product 3 in good yields.

The process for the synthesis of branched C3-alkylated benzofuran compounds of formula (3) is depicted in Scheme 5:

Scheme 5:

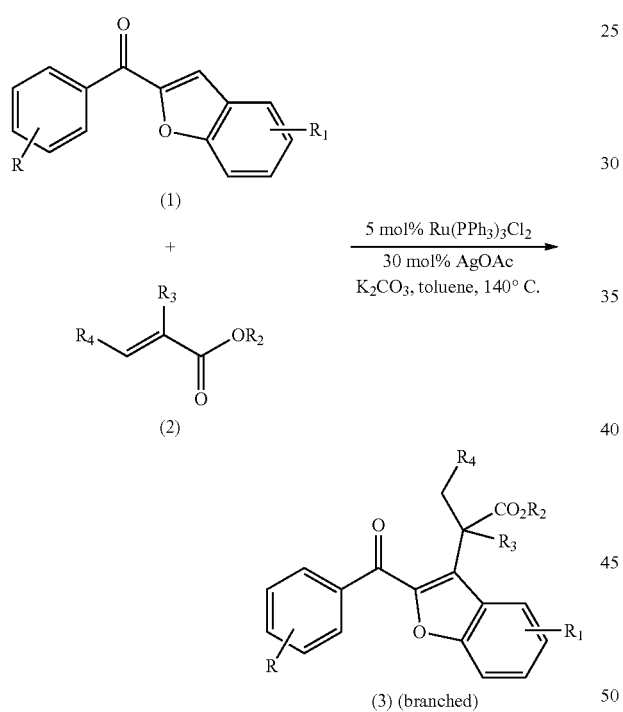

wherein R and $R_1$ are independently selected from the group consisting of hydrogen, halogen, ($C_1$-$C_6$) alkyl, ($C_1$-$C_5$) alkoxy, —$COR_5$, where $R_5$ is ($C_1$-$C_6$) alkyl, aryl or alkylaryl;

$R_2$ is hydrogen, halogen, linear or branched ($C_1$-$C_6$) alkyl, ($C_1$-$C_5$) alkoxy, cyclo ($C_4$-$C_8$) alkyl;

$R_3$ is hydrogen, ($C_1$-$C_6$) alkyl; and $R_4$ is hydrogen, ($C_1$-$C_6$) alkyl, halogen, cycloalkyl, aryl, alkylaryl.

In another preferred embodiment, the branched C3 alkylated benzofuran compounds of Formula (3) synthesized by the instant $Ru(PPh_3)_3Cl_2$ catalyzed selective alkylation process comprising the following compounds;

i. methyl 2-(2-benzoylbenzofuran-3-yl)propanoate (3a):

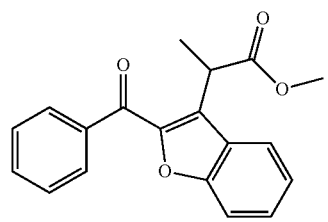 [SMILES: COC(=O)C(C)c1c(C(=O)c2ccccc2)oc2ccccc12]

ii. ethyl 2-(2-benzoylbenzofuran-3-yl)propanoate (3b):

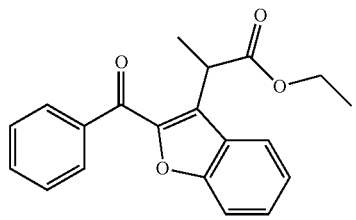 [SMILES: CCOC(=O)C(C)c1c(C(=O)c2ccccc2)oc2ccccc12]

iii. methyl 2-(2-benzoylbenzofuran-3-yl)butanoate (3c):

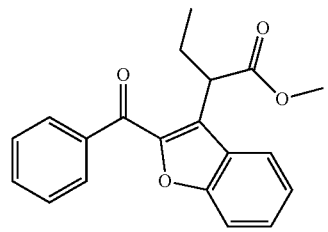 [SMILES: CCC(C(=O)OC)c1c(C(=O)c2ccccc2)oc2ccccc12]

iv. butyl 2-(2-benzoylbenzofuran-3-yl)propanoate (3d):

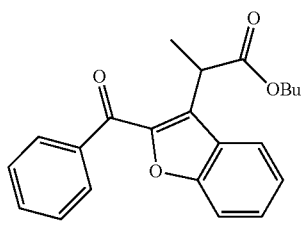

v. cyclohexyl 2-(2-benzoylbenzofuran-3-yl)propanoate (3e):

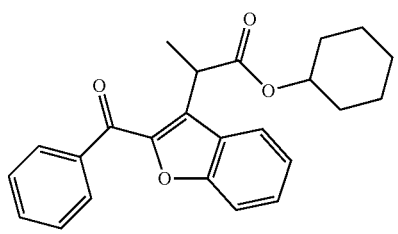 [SMILES: CC(C(=O)OC1CCCCC1)c1c(C(=O)c2ccccc2)oc2ccccc12]

vi. 2-(2-benzoylbenzofuran-3-yl)-N isopropylpropanamide (3i):

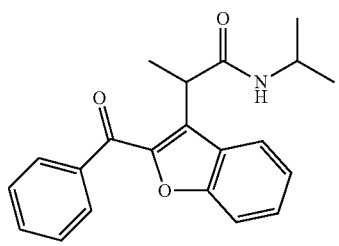 [SMILES: CC(C)NC(=O)C(C)c1c(C(=O)c2ccccc2)oc2ccccc12]

vii. ethyl 2-(2-benzoylbenzofuran-3-yl)-3-phenylpropanoate (3f):

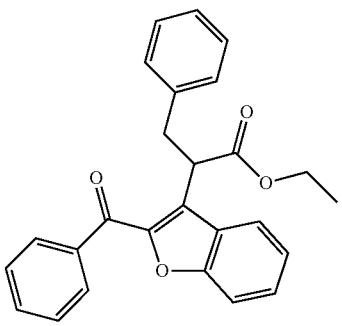 [SMILES: CCOC(=O)C(Cc1ccccc1)c1c(C(=O)c2ccccc2)oc2ccccc12]

viii. methyl 3-(2-benzoylbenzofuran-3-yl)-2-methylpropanoate (3g):

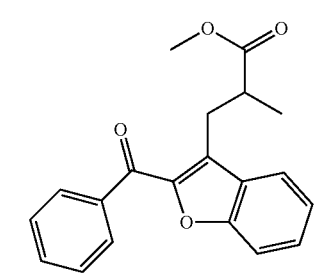 [SMILES: COC(=O)C(C)Cc1c(C(=O)c2ccccc2)oc2ccccc12]

ix. butyl 3-(2-benzoylbenzofuran-3-yl)-2-methylpropanoate (3h):

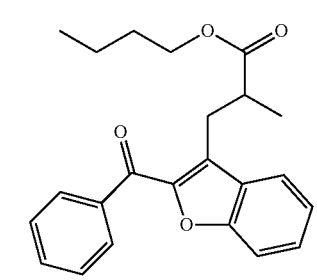 [SMILES: CCCCOC(=O)C(C)Cc1c(C(=O)c2ccccc2)oc2ccccc12]

x. methyl 2-(2-(4-fluorobenzoyl)benzofuran-3-yl)butanoate (3l):

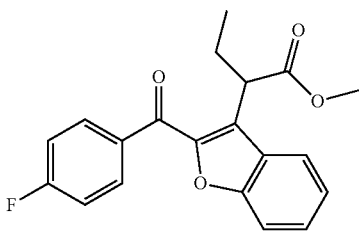 [SMILES: CCC(C(=O)OC)c1c(C(=O)c2ccc(F)cc2)oc2ccccc12]

xi. methyl 2-(2-(4-fluorobenzoyl)benzofuran-3-yl)butanoat:

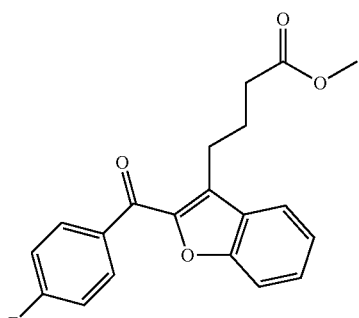

xii. ethyl 2-(2-(4-fluorobenzoyl)benzofuran-3-yl)propanoate (3k):

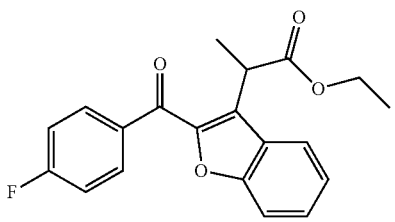 [SMILES: CCOC(=O)C(C)c1c(C(=O)c2ccc(F)cc2)oc2ccccc12]

xiii. methyl 2-(2-(4-fluorobenzoyl)benzofuran-3-yl)propanoate (3j):

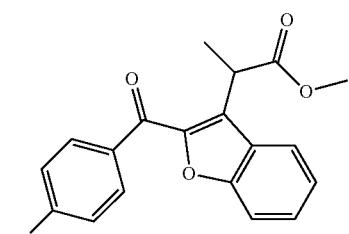

xiv. methyl 2-(2-(4-fluorobenzoyl)benzofuran-3-yl)butanoate (3o):

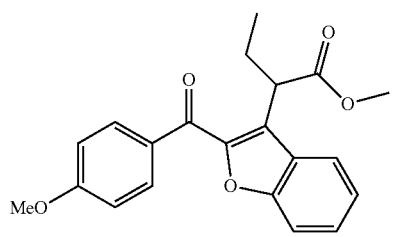 [SMILES: CCC(C(=O)OC)c1c(C(=O)c2ccc(OC)cc2)oc2ccccc12]

xv. methyl 2-(2-(4-fluorobenzoyl)benzofuran-3-yl)butanoate (3n):

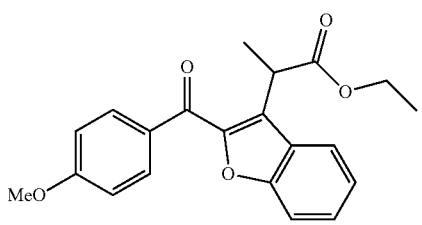 [SMILES: CCOC(=O)C(C)c1c(C(=O)c2ccc(OC)cc2)oc2ccccc12]

xvi. methyl 2-(2-(4-methoxybenzoyl)benzofuran-3-yl)propanoate (3m):

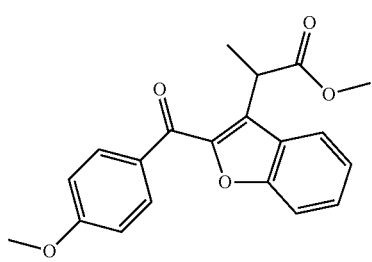

xvii. methyl 2-(5-chloro-2-(4-methoxybenzoyl)benzofuran-3-yl)propanoate (3s):

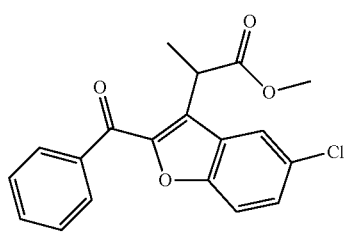 [SMILES: COC(=O)C(C)c1c(C(=O)c2ccccc2)oc2ccc(Cl)cc12]

xviii. methyl 2-(5-chloro-2-(4-methoxybenzoyl)benzofuran-3-yl)propanoate (3t):

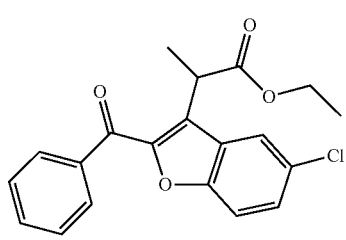 [SMILES: CCOC(=O)C(C)c1c(C(=O)c2ccccc2)oc2ccc(Cl)cc12]

xix. methyl 2-(5-chloro-2-(4-methoxybenzoyl)benzofuran-3-yl)propanoate (3u):

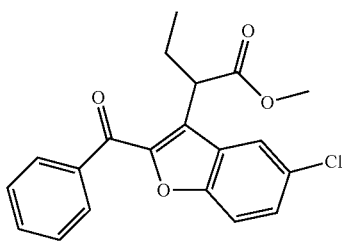 [SMILES: CCC(C(=O)OC)c1c(C(=O)c2ccccc2)oc2ccc(Cl)cc12]

xx. methyl 2-(5-chloro-2-(4-methoxybenzoyl)benzofuran-3-yl)propanoate (3p):

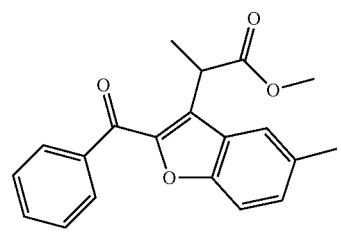 [SMILES: COC(=O)C(C)c1c(C(=O)c2ccccc2)oc2ccc(C)cc12]

xxi. methyl 2-(5-chloro-2-(4-methoxybenzoyl)benzofuran-3-yl)propanoate (3q):

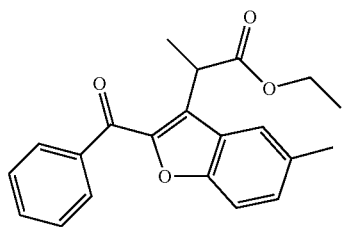 [SMILES: CCOC(=O)C(C)c1c(C(=O)c2ccccc2)oc2ccc(C)cc12]

xxii. methyl 2-(2-benzoyl-5-methoxybenzofuran-3-yl)butanoate (3r):

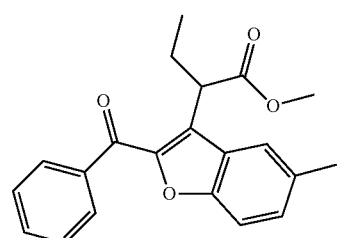

xxiii. Methyl 2-(2-benzoylbenzofuran-3-yl)propanoate (3aa):

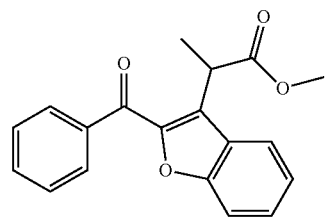 [SMILES: COC(=O)C(C)c1c(C(=O)c2ccccc2)oc2ccccc12]

xxiv. Ethyl 2-(2-benzoylbenzofuran-3-yl)propanoate (3ab):

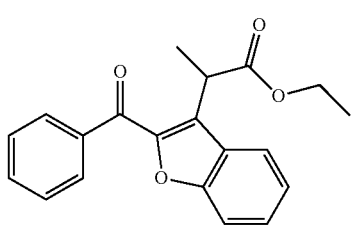 [SMILES: CCOC(=O)C(C)c1c(C(=O)c2ccccc2)oc2ccccc12]

xxv. Butyl 2-(2-benzoylbenzofuran-3-yl)propanoate (3ac):

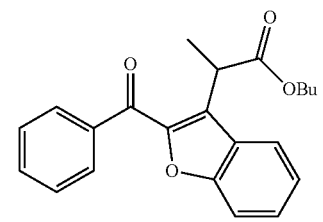

xxvi. Cyclohexyl 2-(2-benzoylbenzofuran-3-yl)propanoate (3ad):

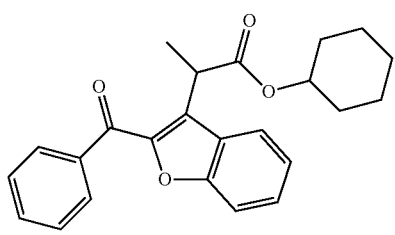 [SMILES: CC(C(=O)OC1CCCCC1)c1c(C(=O)c2ccccc2)oc2ccccc12]

xxvii. Methyl 2-(2-benzoylbenzofuran-3-yl)butanoate (3ae):

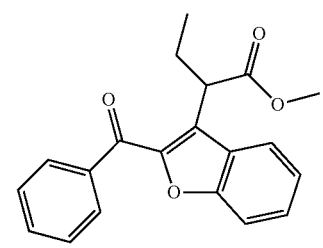 [SMILES: CCC(C(=O)OC)c1c(C(=O)c2ccccc2)oc2ccccc12]

xxviii. Ethyl 2-(2-benzoylbenzofuran-3-yl)-3-phenylpropanoate (3af):

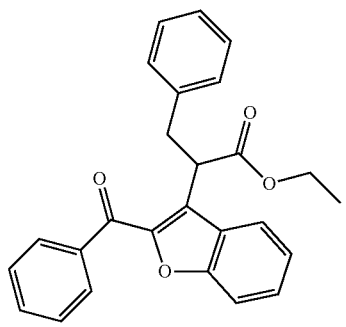 [SMILES: CCOC(=O)C(Cc1ccccc1)c1c(C(=O)c2ccccc2)oc2ccccc12]

xxix. Methyl 2-(2-(4-fluorobenzoyl)benzofuran-3-yl)propanoate (3ba):

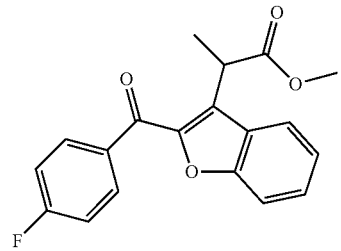 [SMILES: COC(=O)C(C)c1c(C(=O)c2ccc(F)cc2)oc2ccccc12]

xxx. Ethyl 2-(2-(4-fluorobenzoyl)benzofuran-3-yl)propanoate (3bb):

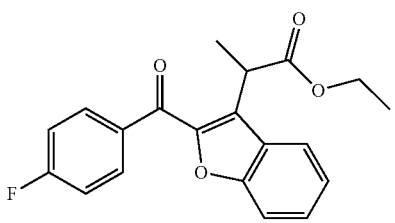 [SMILES: CCOC(=O)C(C)c1c(C(=O)c2ccc(F)cc2)oc2ccccc12]

xxxi. Methyl 2-(2-(4-fluorobenzoyl)benzofuran-3-yl)butanoate (3be):

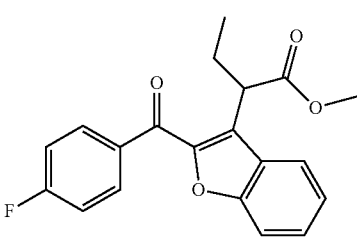 [SMILES: CCC(C(=O)OC)c1c(C(=O)c2ccc(F)cc2)oc2ccccc12]

xxxii. Methyl 2-(2-(4-methoxybenzoyl)benzofuran-3-yl)propanoate (3ca):

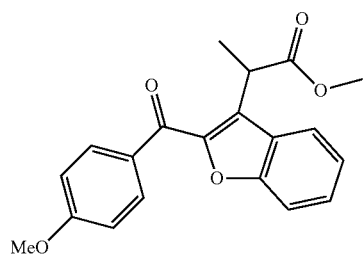 [SMILES: COC(=O)C(C)c1c(C(=O)c2ccc(OC)cc2)oc2ccccc12]

xxxiii. Ethyl 2-(2-(4-methoxybenzoyl)benzofuran-3-yl)propanoate (3cb):

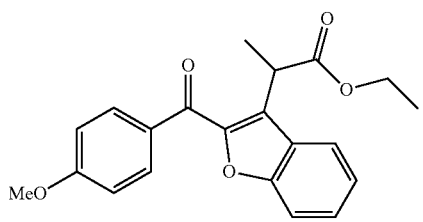 [SMILES: CCOC(=O)C(C)c1c(C(=O)c2ccc(OC)cc2)oc2ccccc12]

xxxiv. Methyl 2-(2-(4-methoxybenzoyl)benzofuran-3-yl)butanoate (3ce):

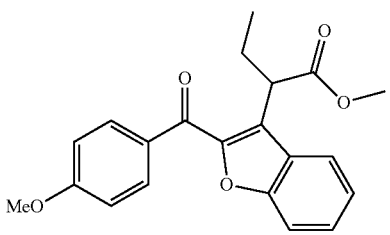

xxxv. Methyl 2-(2-benzoyl-5-methylbenzofuran-3-yl)propanoate (3da):

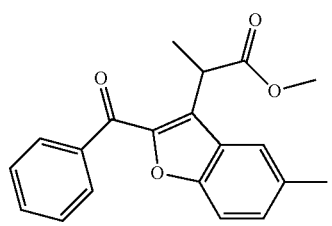 [SMILES: COC(=O)C(C)c1c(C(=O)c2ccccc2)oc2ccc(C)cc12]

xxxvi. Ethyl 2-(2-benzoyl-5-methylbenzofuran-3-yl)propanoate (3db):

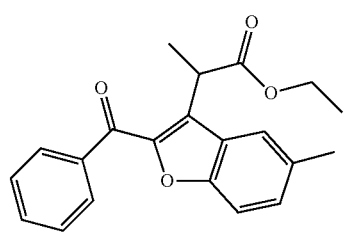 [SMILES: CCOC(=O)C(C)c1c(C(=O)c2ccccc2)oc2ccc(C)cc12]

xxxvii. Methyl 2-(2-benzoyl-5-methylbenzofuran-3-yl)butanoate (3de):

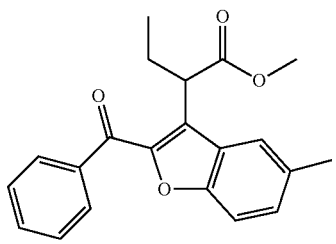 [SMILES: CCC(C(=O)OC)c1c(C(=O)c2ccccc2)oc2ccc(C)cc12]

xxxviii. Methyl 2-(2-benzoyl-5-chlorobenzofuran-3-yl)propanoate (3ea):

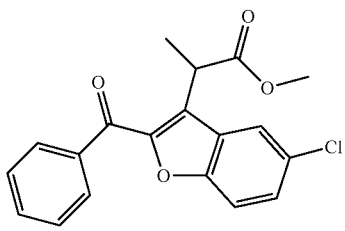 [SMILES: COC(=O)C(C)c1c(C(=O)c2ccccc2)oc2ccc(Cl)cc12]

xxxix. Ethyl 2-(2-benzoyl-5-chlorobenzofuran-3-yl)propanoate (3eb):

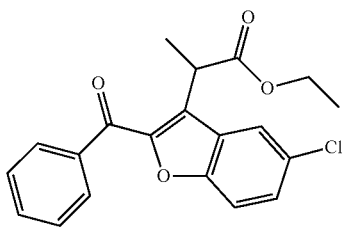 [SMILES: CCOC(=O)C(C)c1c(C(=O)c2ccccc2)oc2ccc(Cl)cc12]

xl. Methyl 2-(2-benzoyl-5-chlorobenzofuran-3-yl)butanoate (3 ee):

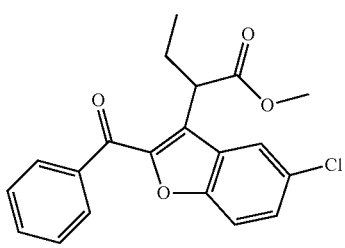 [SMILES: CCC(C(=O)OC)c1c(C(=O)c2ccccc2)oc2ccc(Cl)cc12]

xli. 2-(2-benzoylbenzofuran-3-yl)-N-isopropylpropanamide (3aj):

xlii. (3-phenethylbenzofuran-2-yl)(phenyl)methanone (3al)

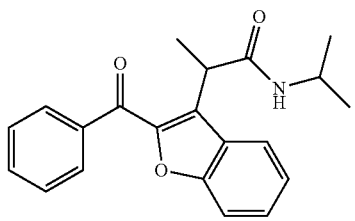 [SMILES: CC(C)NC(=O)C(C)c1c(C(=O)c2ccccc2)oc2ccccc12]

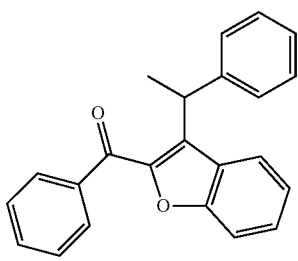 [SMILES: CC(c1ccccc1)c1c(C(=O)c2ccccc2)oc2ccccc12]

In additional embodiment, the present invention provides a process for the synthesis of compounds of formula 3, comprising the steps of:
a. Adding [Ru(PPh$_3$)$_3$Cl$_2$, AgOAc, alkene, K$_2$CO$_3$ to a reaction vessel containing a mixture of 2-aroylbenzofuran and toluene under argon atmosphere to get a solution mixture;
b. Stirring the solution mixture at a temperature in the range of 130 to 150° C., for time in the range of 20-30 hrs followed by cooling the solution mixture and work-up afforded the crude products which is further purified by column chromatography to obtain pure product 3 in good yields.

According to the embodiment the alkene or olefin derivatives are having formula 2';

wherein, R$_2$ is selected from group consisting of aryl, (C$_1$-C$_6$) alkyl substituted acetamide, branched or linear(C$_1$-C$_{12}$) preferably phenyl, CONHiPr, C$_{10}$H$_{21}$.

The scope of the alkene/olefins in branched selective alkylation to obtain benzofuran product either linear or branched or mixtare thereof is depicted in table 2.

In another preferred embodiment, the invention provides a process for the synthesis of linear C3-alkylated benzofuran compounds of formula (4), comprising the steps of:
a. Adding 2-aroylbenzofuran (1), acrylate (2) and dioxane to a reaction vessel containing a mixture of [Ru(p-cymene)Cl$_2$]$_2$, PPh$_3$ and NaHCO$_3$ under argon atmosphere to get a solution mixture;
b. Stirring the solution mixture at a temperature in the range of 130 to 150° C., for time in the range of 30 to 40 hrs followed by cooling the solution mixture and work-up afforded the crude products which is further purified by column chromatography to obtain pure linear alkylated, products in good yields.

The process for the synthesis of linear C3-alkylated benzofuran compounds of formula (4) is depicted in Scheme 6:

Scheme 6:

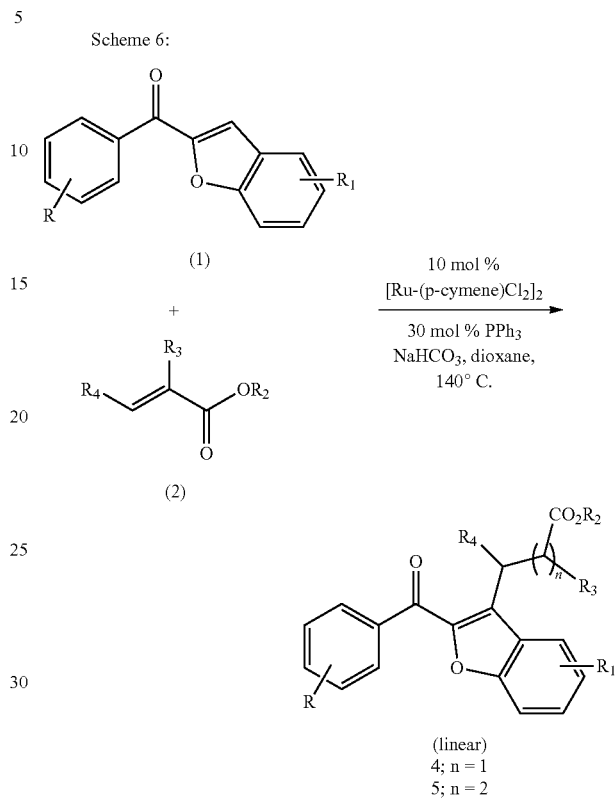

wherein 'n' is an integer ranges from 1 to 6;
wherein R and R$_1$ are independently selected from the group consisting of hydrogen, halogen, (C$_1$-C$_6$) alkyl, (C$_1$-C$_5$) alkoxy, —COR$_5$, where R$_5$ is (C$_1$-C$_6$) alkyl, aryl or alkylaryl;
R$_2$ is hydrogen, halogen, linear or branched (C$_1$-C$_6$) alkyl, (C$_1$-C$_5$) alkoxy, cyclo (C$_4$-C$_8$) alkyl;
R$_3$ is hydrogen, (C$_1$-C$_6$) alkyl; and
R$_4$ is hydrogen, (C$_1$-C$_6$) alkyl, halogen, cycloalkyl, aryl, alkylaryl.

In another preferred embodiment, the linear C3-alkylated benzofuran compounds of Formula (4) synthesized by the instant Ru(p-cymene)Cl$_2$]$_2$, PPh$_3$ catalyzed selective alkylation process comprising the following compounds;
i. ethyl 2-(2-(4-fluorobenzoyl)benzofuran-3-yl)propanoate (4i):

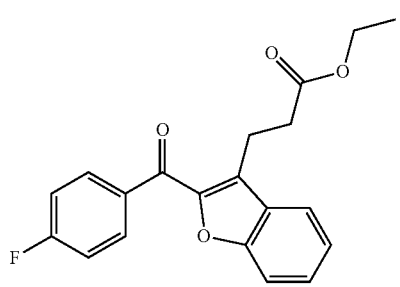 [SMILES: CCOC(=O)CCc1c(C(=O)c2ccc(F)cc2)oc2ccccc12]

ii. methyl 2-(2-(4-fluorobenzoyl)benzofuran-3-yl)propanoate (4h):

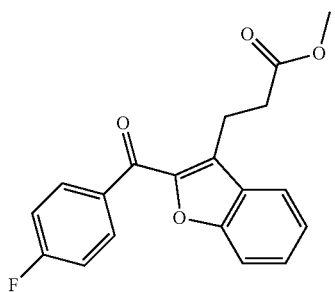 [SMILES: COC(=O)CCc1c(C(=O)c2ccc(F)cc2)oc2ccccc12]

iii. Methyl 3-(2-benzoylbenzofuran-3-yl)propanoate (4a):

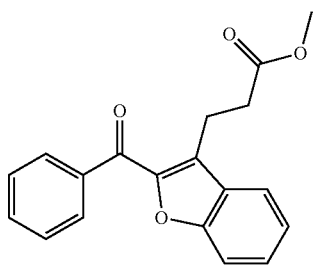 [SMILES: COC(=O)CCc1c(C(=O)c2ccccc2)oc2ccccc12]

iv. Ethyl 3-(2-benzoylbenzofuran-3-yl)propanoate (4b):

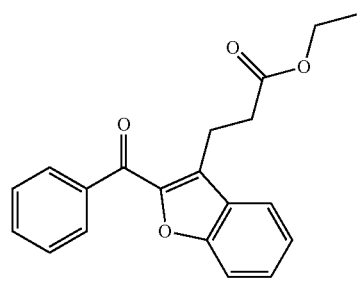 [SMILES: CCOC(=O)CCc1c(C(=O)c2ccccc2)oc2ccccc12]

v. Butyl 3-(2-benzoylbenzofuran-3-yl)propanoate (4c):

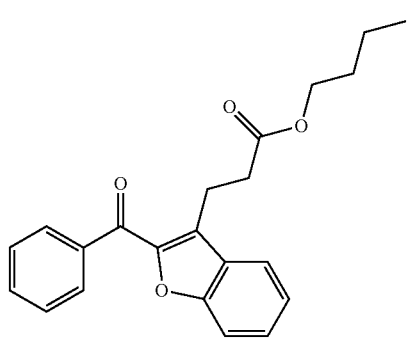 [SMILES: CCCCOC(=O)CCc1c(C(=O)c2ccccc2)oc2ccccc12]

vi. Methyl 3-(2-(4-methoxybenzoyl)benzofuran-3-yl)propanoate (4j):

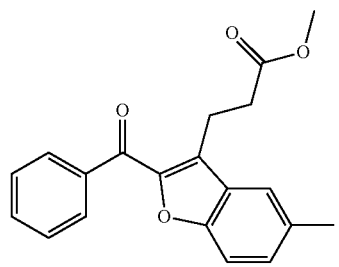 [SMILES: COC(=O)CCc1c(C(=O)c2ccccc2)oc2ccc(C)cc12]

vii. Ethyl 3-(2-(4-methoxybenzoyl)benzofuran-3-yl)propanoate (4k):

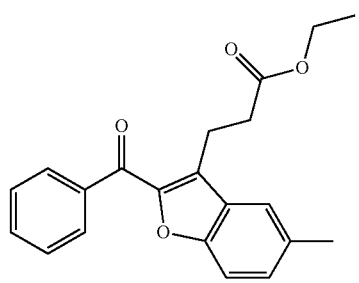 [SMILES: CCOC(=O)CCc1c(C(=O)c2ccccc2)oc2ccc(C)cc12]

viii. Methyl 3-(2-benzoyl-5-chlorobenzofuran-3-yl)propanoate (4f):

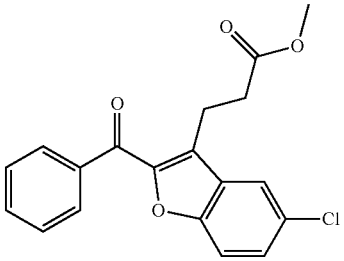 [SMILES: COC(=O)CCc1c(C(=O)c2ccccc2)oc2ccc(Cl)cc12]

ix. Ethyl 3-(2-benzoyl-5-chlorobenzofuran-3-yl)propanoate (4g):

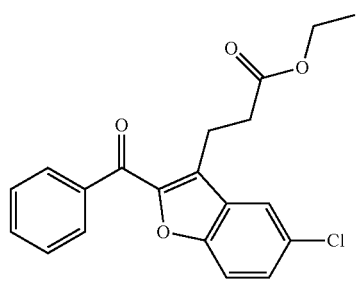 [SMILES: CCOC(=O)CCc1c(C(=O)c2ccccc2)oc2ccc(Cl)cc12]

x. Methyl 3-(2-(4-methoxybenzoyl)benzofuran-3-yl)propanoate (4d):

xi. Ethyl 3-(2-(4-methoxybenzoyl)benzofuran-3-yl)propanoate (4c):
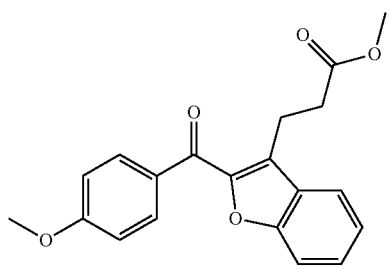
xii. Methyl 3-(2-benzoylbenzofuran-3-yl)-2-methylpropanoate (4ag):
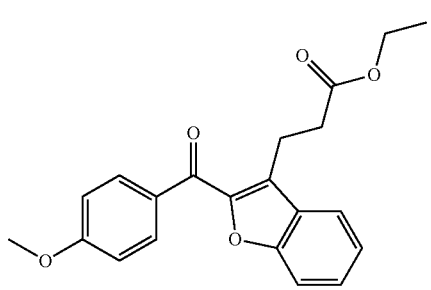 [SMILES: CCOC(=O)CCc1c(C(=O)c2ccc(OC)cc2)oc2ccccc12]
xiii. Butyl 3-(2-benzoylbenzofuran-3-yl)-2-methylpropanoate (4ah):
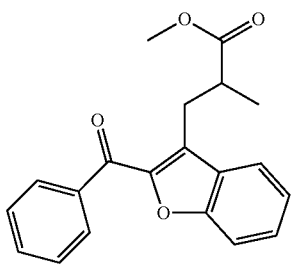 [SMILES: COC(=O)C(C)Cc1c(C(=O)c2ccccc2)oc2ccccc12]
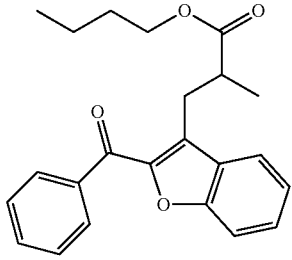 [SMILES: CCCCOC(=O)C(C)Cc1c(C(=O)c2ccccc2)oc2ccccc12]
xiv. Methyl 3-(2-benzoylbenzofuran-3-yl)propanoate (4ha):
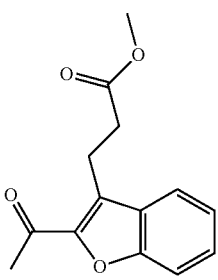 [SMILES: COC(=O)CCc1c(C(C)=O)oc2ccccc12]
xv. (phenyl(3-(1-phenylethyl)benzofuran-2-yl)methanone (4al):
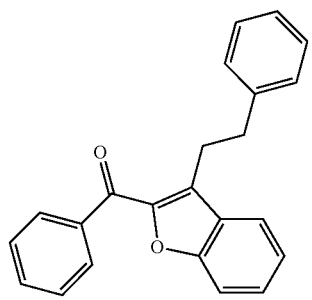 [SMILES: O=C(c1ccccc1)c1oc2ccccc2c1CCc1ccccc1]
xvi. Phenyl(3-undecylbenzofuran-2-yl)methanone (4am):
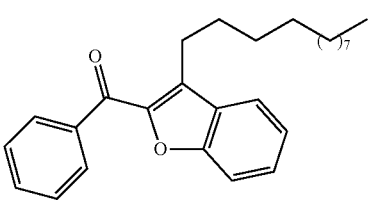
xvii. Methyl 3-(2-benzoylbenzofuran-3-yl)propanoate (4aa):
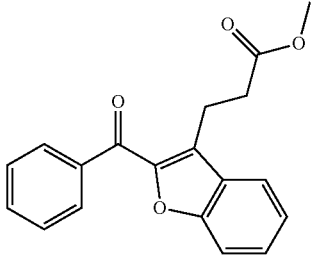 [SMILES: COC(=O)CCc1c(C(=O)c2ccccc2)oc2ccccc12]

xviii. Ethyl 3-(2-benzoylbenzofuran-3-yl)propanoate (4ab):

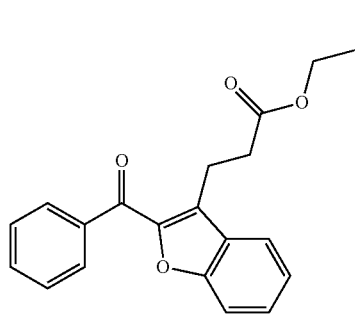 [SMILES: CCOC(=O)CCc1c(C(=O)c2ccccc2)oc2ccccc12]

xix. Butyl 3-(2-benzoylbenzofuran-3-yl)propanoate (4ac):

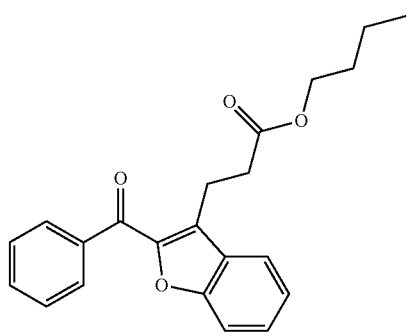 [SMILES: CCCCOC(=O)CCc1c(C(=O)c2ccccc2)oc2ccccc12]

xx. Methyl 3-(2-(4-fluorobenzoyl)benzofuran-3-yl)propanoate (4ba):

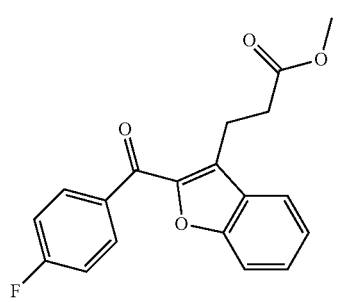 [SMILES: COC(=O)CCc1c(C(=O)c2ccc(F)cc2)oc2ccccc12]

xxi. Ethyl 3-(2-(4-fluorobenzoyl)benzofuran-3-yl)propanoate (4bb):

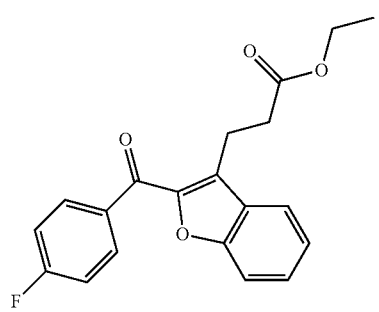 [SMILES: CCOC(=O)CCc1c(C(=O)c2ccc(F)cc2)oc2ccccc12]

xxii. Methyl 3-(2-(4-methoxybenzoyl)benzofuran-3-yl)propanoate (4ca):

xxiii. Ethyl 3-(2-(4-methoxybenzoyl)benzofuran-3-yl)propanoate (4cb):

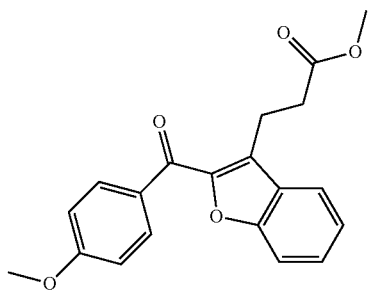

xxiv: Methyl 3-(2-benzoyl-5-methylbenzofuran-3-yl)propanoate (4da):

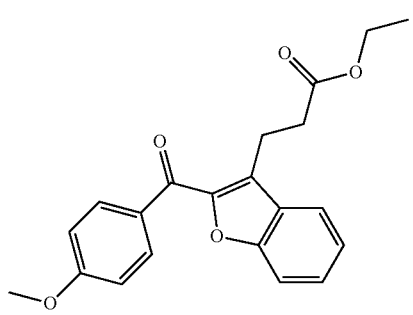 [SMILES: CCOC(=O)CCc1c(C(=O)c2ccc(OC)cc2)oc2ccccc12]

xxv. Ethyl 3-(2-benzoyl-5-methylbenzofuran-3-yl)propanoate (4db):

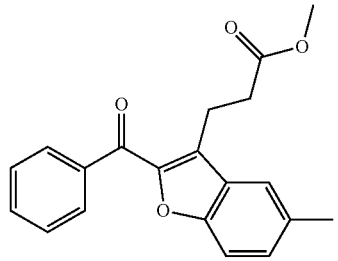 [SMILES: COC(=O)CCc1c(C(=O)c2ccccc2)oc2ccc(C)cc12]

xxvi. Methyl 3-(2-benzoyl-5-chlorobenzofuran-3-yl)propanoate (4ea):

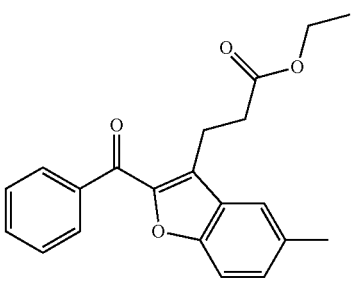

xxvii. Ethyl 3-(2-benzoyl-5-chlorobenzofuran-3-yl)propanoate (4eb):

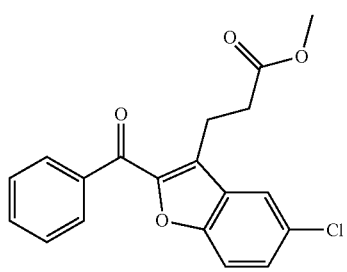 [SMILES: COC(=O)CCc1c(C(=O)c2ccccc2)oc2ccc(Cl)cc12]

xxviii. Methyl 4-(2-benzoylbenzofuran-3-yl)butanoate (5):

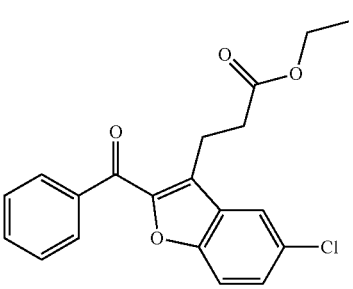 [SMILES: CCOC(=O)CCc1c(C(=O)c2ccccc2)oc2ccc(Cl)cc12]

xxix. Methyl 4-(2-(4-fluorobenzoyl)benzofuran-3-yl)butanoate (5be):

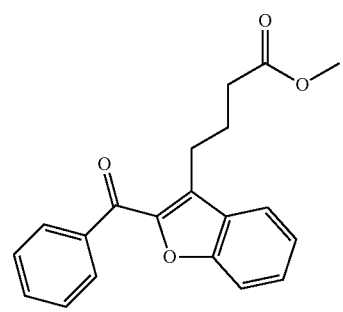 [SMILES: COC(=O)CCCc1c(C(=O)c2ccccc2)oc2ccccc12]

According to the process the better linear selectivity that has been noticed with the [Ru(p-cymene)Cl$_2$]$_2$ complex and the previous findings of Darses and Genet (*J. Org. Chem.* 2010, 75, 208) on the use of additional phosphine for the high linear selectivity in alkylations with styrenes. The addition of 30 mol % PPh$_3$ and the use of NaHCO$_3$ as base (5 eq.) and 1,4-dioxane as solvent ameliorate the linear product with excellent yield and with good selectivity.

In yet another embodiment the invention provides the scope of the substrate (1) and acrylates (2) to yield desired product (3) and (4) in good yield, cf scheme 7a-7d.

Scheme 7a:

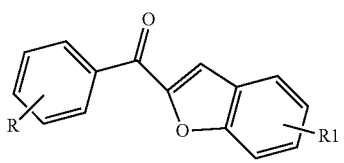

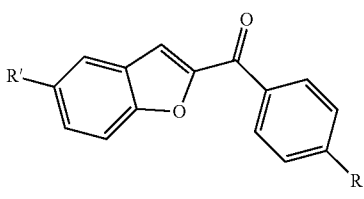

R' = R1
1a ( R = H, R' = H)
1b ( R = F, R' = H)
1c ( R = OMe, R' = H)
1d ( R = H, R' = Me)
1e ( R = H, R' = Cl)

Scheme 7b:

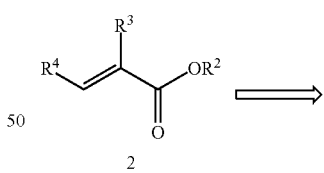

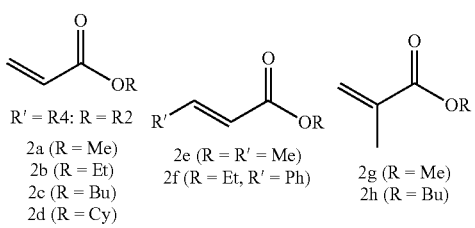

R' = R4: R = R2
2a (R = Me)
2b (R = Et)
2c (R = Bu)
2d (R = Cy)

2e (R = R' = Me)
2f (R = Et, R' = Ph)

2g (R = Me)
2h (R = Bu)

Scheme 7c:

Branched alkylated benzofuran (3)

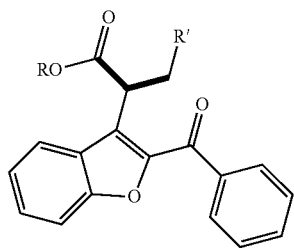

R = R2 ; R' = R4 (Formula-3)

3ab, R = Et, R' = H, 88% (92:8)
3ac, R = Bu, R' = H, 86% (92:8)
3ad, R = Cy R' = H, 87% (91:9)
3ae, R = R' = Me, 84% (91.9)[a]
3af, R = Et, R' = Ph, 54% (94:6)

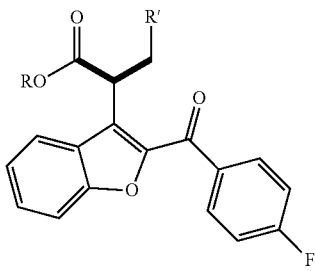

3ba, R = Me, R' = H, 87% (88:12)
3bb, R = Et, R' = H, 89% (87:13)
3be, R = R' = Me, 90% (87:13)[a]

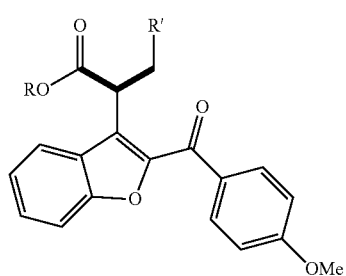

3ca, R = Me, R' = H, 83% (91:9)
3cb, R = Et, R' = H, 80% (92:8)
3ce, R = R' = Me, 86% (91:9)[a]

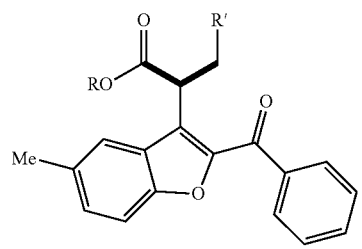

3da, R = Me, R' = H, 82% (88:12)
3db, R = Et, R' = H, 79% (86:14)
3de, R = R' = Me, 80% (85:15)[a]

-continued

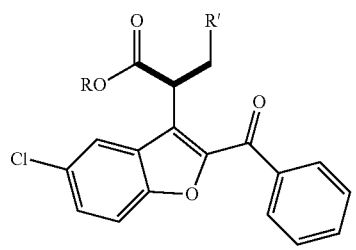

3ea, R = Me, R' = H, 87% (91:9)
3eb, R = Et, R' = H, 86% (93:7)
3ee, R = R' = Me, 89% (91:9)[a]

[a]the ratio given corresponds branched vs 1,5-addition products (3:5)

Scheme 7d:

Linear alkylated benzofurans

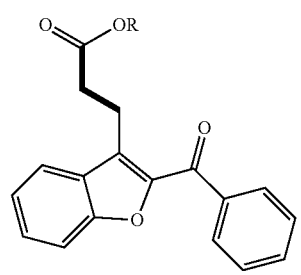

4aa, R = Me, 73% (14:86)
4ab, R = Et, 74% (12:88)
4ac, R = Bu, 79% (14:86)

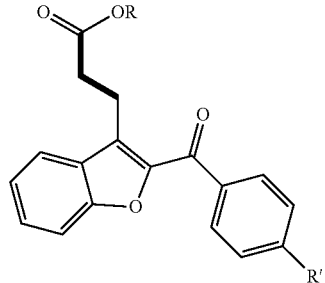

4ba, R = Me, R' = F, 66% (14:86)
4bb, R = Et, R' = F, 74% (23:77)
4ca, R = Me, R' = OMe, 64% (27:73)
4cb, R = Et, R' = OMe, 72% (40:60)

R = R2; R' = R (Formula-4)

4da, R = Me, 69% (18:82)
4db, R = Et, 65% (6:94)

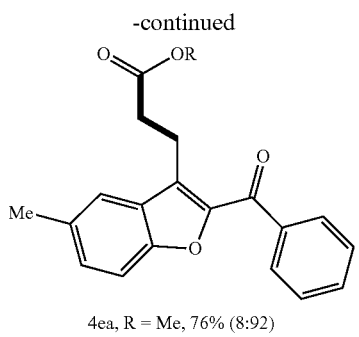

4ea, R = Me, 76% (8:92)
4eb, R = Et, 71% (7:93)

[a] the ratio indicates branched vs linear products (3:4),
[b] ration of branched vs linear determined by HPLC With regard to the invention, the compatibility of various α,β-unsaturated esters (2) as coupling partners has been explored under the optimized conditions employing 1a as the substrate. The reaction of 1a with ethyl-, butyl-, and cyclohexyl acrylates (2b-2d) gave the corresponding products in very good isolated yields without substantial difference in the branched/linear selectivity.

In case of methyl crotonate (2e), the reaction proceeded smoothly and the corresponding branched adduct 3ae was obtained as the major product and the 1,5-addition linear adduct (5) was obtained as the minor isomer with an overall yield of 84%. However, with both methyl- and butyl methacrylates (2g and 2h), were formed the corresponding linear adducts 4ag and 4ah as the only products. This result indicates that steric factors might be playing a substantial role in deciding the linear vs branched selectivity. In the case of ethyl cinnamate (2f), the reaction was sluggish and the branched adduct 3af was obtained as the major product in moderate yield/conversion.

The scheme 7 summarizes the generality branched selective alkylation of 2-aroylbenzofurans 1b-1e with acrylates 2a, 2b, 2e. As indicated, the yields are good to excellent. The presence of electron donating groups on the phenyl ring and of the electron withdrawing groups on the benzofuran ring seems to increase the branched selectivity. This complementary electronic effect on the branched vs linear selectivity induced by the substituents present on either of the aryl and benzofuran rings suggest that the polarity of the Ru—C carbon bond of the intermediate organo-ruthenium species is susceptible for electronic perturbations from either side.

Further the scope of the linear selective alkylation was established by employing 1a-1e and acrylates 2a/2b. As described above, the best linear selectivity was observed with the substrate 1e (with chlorine at the C5 of the benzofuran ring). On the other hand, the presence of the electron donating groups on the phenyl ring (substrate 1c) reduced the selectivity (3cb/4cb=40:60). As mentioned earlier, the same substrate 1c gave the best branched selectivity (3ca/4ca=92:8). This indicates a competing steric vs electronic influence on the branched vs linear selectivity. The reactions with methyl crotonate, in general, are sluggish.

In an embodiment, the present invention provides the deuterium labeling experiments that reveals that both the pendant aryl C2-H and benzofyranly C3-H are equally susceptible for cleavage, the alkylation exclusively occurred on the C3 position of the benzofuran unit.

Therefore the instant invention provides ruthenium-catalyzed complementary branched and linear selective alkylation of aroylbenzofuran with acrylates via C—H activation. The remarkable feature of the present transformation is the regioselectivity of the coupling process. Even though the deuterium labelling experiments reveal that both the pendant aryl C2'/C6'-H and benzofuranyl C3-H are equally susceptible for cleavage, the alkylation has exclusively occurred on the C3 of the benzofuran unit. The catalyst dependent complementary linear vs branched selectivity that has been observed has been ascertained to be due to competing steric vs electronic factors. Further investigations on understanding the detailed mechanism of this reaction and also on the applicability of this method with the other aryl/hetero aryl systems are currently in progress.

In yet another preferred embodiment, the invention provides Ru catalyzed C2-alkylation of 3-aroylbenzofuran with alpha beta unsaturated ester (acrylate) via C—H activation under optimum condition (as described in Scheme 3).

Scheme 3:

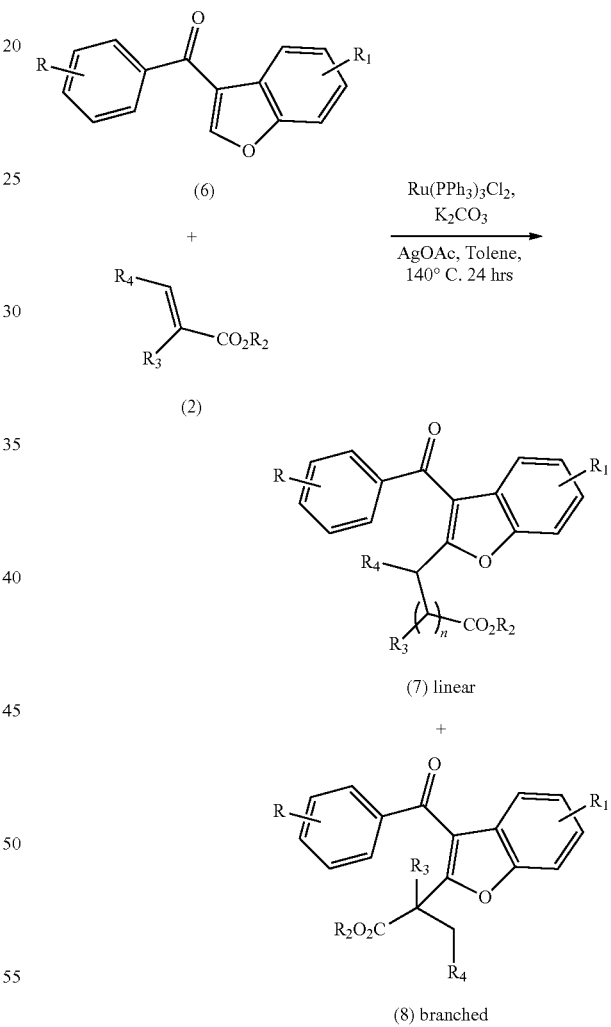

wherein 'n' is an integer ranges from 1 to 6;
R and $R_1$ are independently selected from the group consisting of hydrogen, halogen, $(C_1-C_6)$ alkyl, $(C_1-C_5)$ alkoxy, —$COR_5$, where $R_5$ is $(C_1-C_6)$ alkyl, aryl or alkylaryl;
$R_2$ is hydrogen, halogen, linear or branched $(C_1-C_6)$ alkyl, $(C_1-C_5)$ alkoxy, cyclo $(C_4-C_8)$ alkyl;
$R_3$ is hydrogen, $(C_1-C_6)$ alkyl; and
$R_4$ is hydrogen, $(C_1-C_6)$ alkyl, halogen, cycloalkyl, aryl, alkylaryl.

In another preferred embodiment, the invention provides a process for the synthesis of linear or branched C2-alkylated benzofuran compounds of formula (7) and (8), comprising the steps of:
a. Adding 3-aroylbenzofuran (6), acrylate (2), $K_2CO_3$ and toluene to a reaction vessel containing a mixture of $[Ru(PPh_3)_3]Cl_2$, AgOAc under argon atmosphere to get a solution mixture;
b. Stirring the solution mixture at a temperature in the range of 130 to 150° C., for time in the range of 20 to 30 hrs followed by cooling the solution mixture and work-up afforded the crude products which is further purified by column chromatography to obtain pure benzofuran products (7) or (8) or mixture thereof in good yields.

According to the invention, both electron donating and electron withdrawing groups are placed on aryl and benzofuran ring (6) to test the electronic effects of substitutents on the rate and selectivity of reaction.

The benzofuran compounds (6) are selected from the group consisting of;

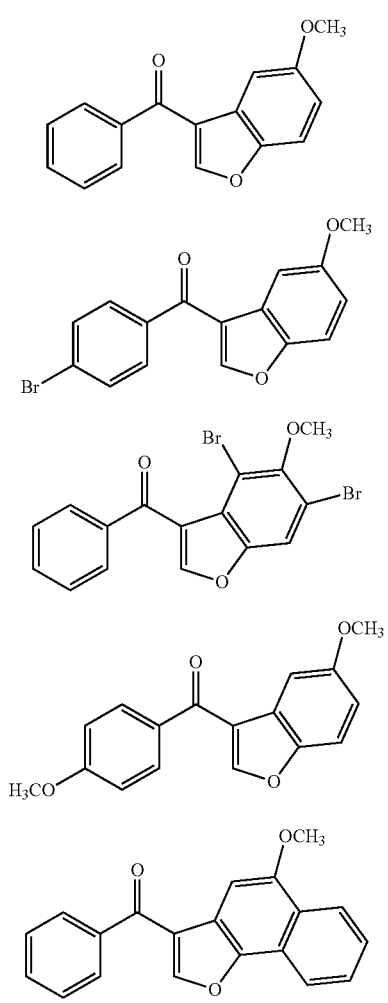

The acrylate derivatives (2) are linear or branched ($C_1$-$C_6$)alkyl, cyclo ($C_4$-$C_8$)alkyl, ($C_1$-$C_6$)alkyl methacrylates, linear or branched ($C_1$-$C_6$) alkyl crotonate, substituted or unsubstituted acrylamide. Preferably acrylate derivatives (2) are selected from methyl, ethyl, terbutyl, cyclohexyl acrylates, methyl methacrylate, methyl crotonate, N-isopropylacrylamide.

In further embodiment, the C2-alkylation of 3-aroylbenzofuran compounds with linear or branched or cyclic alkyl acrylates results in exclusively linear alkylated benzofuran product (7). However reaction in presence of methylcrotonate and N-isopropylacrylamide gives mixture of branched and linear alkylated adducts (7) and (8). Reactions using acrylonitrile, acrylic acid, triethoxyvinylsilane were not successful.

In another typical embodiment, the invention provides synthesis of linear C2-alkylated benzofuran compounds of formula (7), comprises reaction of (5-methoxy-1-benzofuran-3-yl)(phenyl)methanone (6a) with linear or branched ($C_1$-$C_6$)alkyl, cyclo ($C_4$-$C_8$)alkyl acrylates in presence of $K_2CO_3$, $Ru(PPh_3)_3Cl_2$ and AgOAc, toluene at 140° C. (bath temperature) for 24 h, followed by cooling the reaction mixture to room temperature to obtain the crude products which is further purified by column chromatography (pet ether/AcOEt) to give analytically pure linear alkylated products (cf scheme 8).

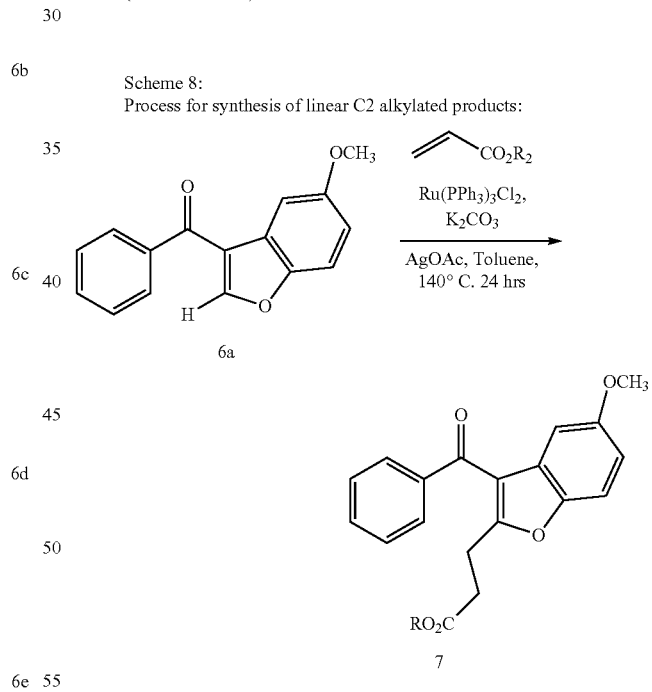

Scheme 8:
Process for synthesis of linear C2 alkylated products:

Similarly, the substrate (6a-6e) gives corresponding linear C2 alkylated products on treatment with acrylates (2) under same conditions.

In yet another embodiment, the linear C2 alkylated products synthesized by the instant process encompass the following compounds;

i. Methyl 3-(3-benzoyl-5-methoxybenzofuran-2-yl)propanoate: (7a)

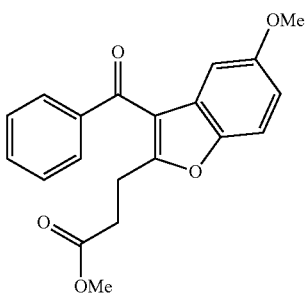 [SMILES: COC(=O)CCc1oc2ccc(OC)cc2c1C(=O)c1ccccc1]

ii. Ethyl 3-(3-benzoyl-5-methoxybenzofuran-2-yl)propanoate: (7b)

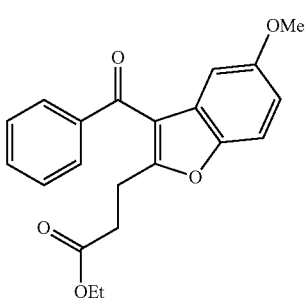 [SMILES: CCOC(=O)CCc1oc2ccc(OC)cc2c1C(=O)c1ccccc1]

iii. Tert-butyl 3-(3-benzoyl-5-methoxybenzofuran-2-yl)propanoate: (7c)

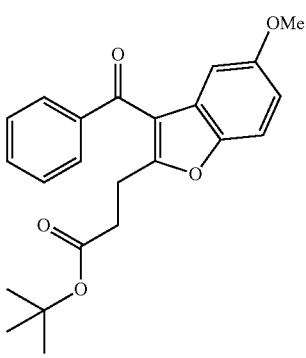 [SMILES: COc1ccc2oc(CCC(=O)OC(C)(C)C)c(C(=O)c3ccccc3)c2c1]

iv. Methyl 3-(3-benzoyl-5-methoxybenzofuran-2-yl)-2-methylpropanoate: (7d)

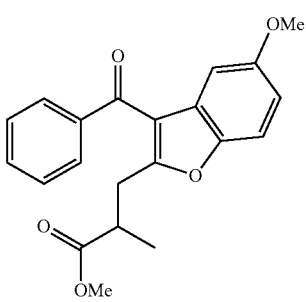 [SMILES: COC(=O)C(C)Cc1oc2ccc(OC)cc2c1C(=O)c1ccccc1]

v. Cyclohexyl 3-(3-benzoyl-5-methoxybenzofuran-2-yl)propanoate: (7e)

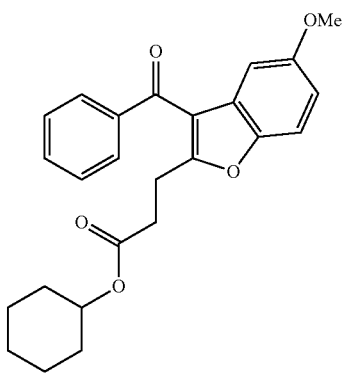 [SMILES: COc1ccc2oc(CCC(=O)OC3CCCCC3)c(C(=O)c3ccccc3)c2c1]

vi. Methyl 2-(3-benzoyl-5-methoxybenzofuran-2-yl)butanoate: (7f)

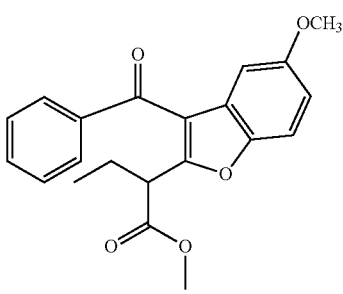 [SMILES: CCC(C(=O)OC)c1oc2ccc(OC)cc2c1C(=O)c1ccccc1]

vii. Methyl 4-(3-benzoyl-5-methoxybenzofuran-2-yl)butanoate: (7g)

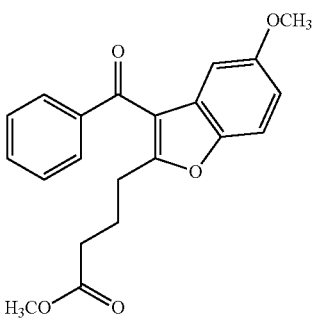 [SMILES: COC(=O)CCCc1oc2ccc(OC)cc2c1C(=O)c1ccccc1]

viii. 2-(3-benzoyl-5-methoxybenzofuran-2-yl)-N-isopropylpropanamide: (7h)

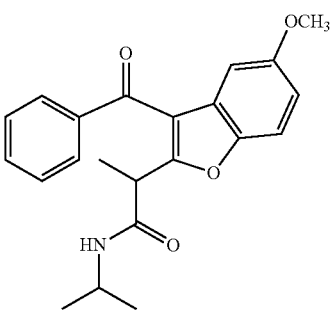 [SMILES: COc1ccc2oc(C(C)C(=O)NC(C)C)c(C(=O)c3ccccc3)c2c1]

ix. 3-(3-benzoyl-5-methoxybenzofuran-2-yl)-N-isopropyl-propanamide: (7i)

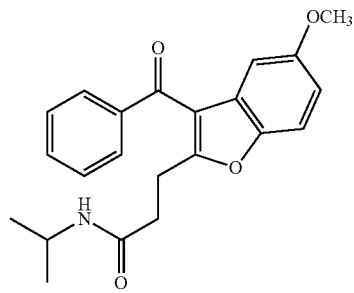 [SMILES: COc1ccc2oc(CCC(=O)NC(C)C)c(C(=O)c3ccccc3)c2c1]

x. Tert-butyl 3-(5-methoxy-3-(4-methoxybenzoyl)benzofuran-2-yl)propanoate: (7j)

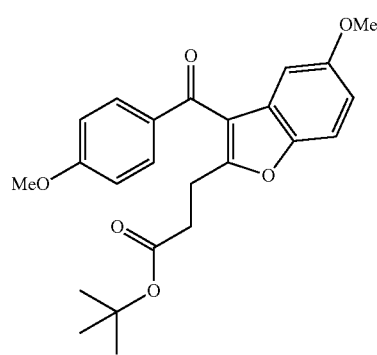 [SMILES: COc1ccc(C(=O)c2c(CCC(=O)OC(C)(C)C)oc3ccc(OC)cc23)cc1]

xi. Methyl 3-(5-methoxy-3-(4-methoxybenzoyl)benzofuran-2-yl)-2-methylpropanoate: (7k)

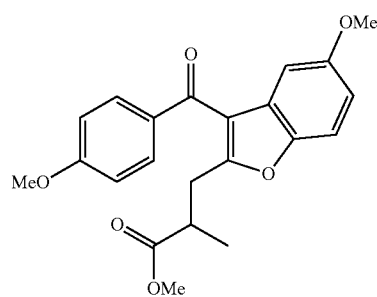 [SMILES: COC(=O)C(C)Cc1oc2ccc(OC)cc2c1C(=O)c1ccc(OC)cc1]

xii. Methyl 4-(5-methoxy-3-(4-methoxybenzoyl)benzofuran-2-yl)butanoate: 7(l)

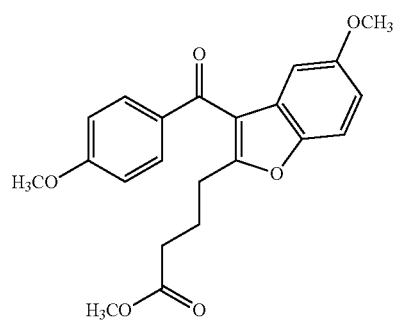 [SMILES: COC(=O)CCCc1oc2ccc(OC)cc2c1C(=O)c1ccc(OC)cc1]

xiii. Tert-butyl 3-(3-(4-bromobenzoyl)-5-methoxybenzofuran-2-yl)propanoate: 7(m)

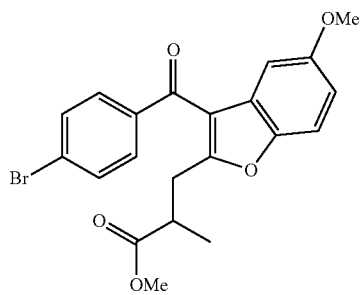 [SMILES: COC(=O)C(C)Cc1oc2ccc(OC)cc2c1C(=O)c1ccc(Br)cc1]

xiv. Methyl 3-(3-(4-bromobenzoyl)-5-methoxybenzofuran-2-yl)-2-methylpropanoate: 7(n)

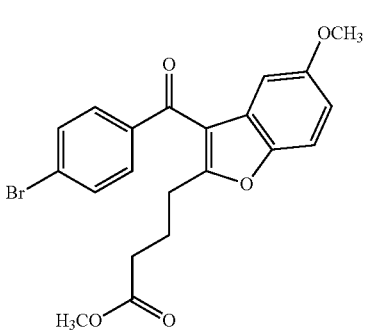 [SMILES: COC(=O)CCCc1oc2ccc(OC)cc2c1C(=O)c1ccc(Br)cc1]

xv. Methyl 4-(3-(4-bromobenzoyl)-5-methoxybenzofuran-2-yl)butanoate: 7(o)

xvi. Tert-butyl 3-(3-benzoyl-5-methoxynaphtho[1,2-b]furan-2-yl)propanoate: 7(p)

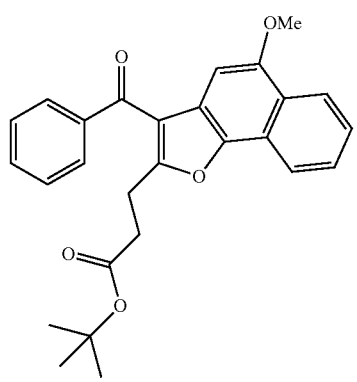 [SMILES: COc1cc2c(C(=O)c3ccccc3)c(CCC(=O)OC(C)(C)C)oc2c2ccccc12]

xvii. Methyl 3-(3-benzoyl-5-methoxynaphtho[1,2-b]furan-2-yl)-2-methylpropanoate: 7(q)

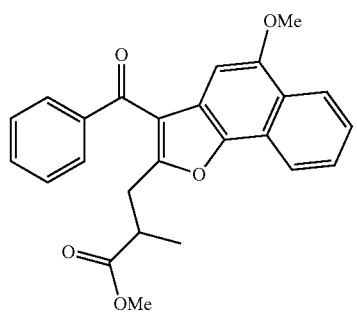 [SMILES: COC(=O)C(C)Cc1oc2c(cc(OC)c3ccccc32)c1C(=O)c1ccccc1]

xviii. Tert-butyl 3-(3-benzoyl-4,6-dibromo-5-methoxybenzofuran-2-yl)propanoate: 7(r)

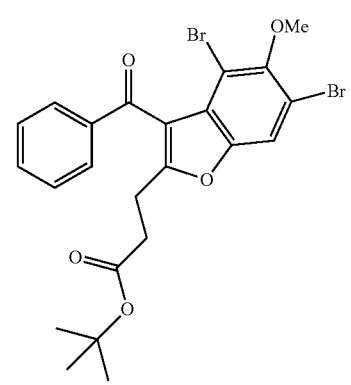 [SMILES: COc1c(Br)cc2oc(CCC(=O)OC(C)(C)C)c(C(=O)c3ccccc3)c2c1Br]

xix. Methyl 3-(3-benzoyl-4,6-dibromo-5-methoxybenzofuran-2-yl)-2-methylpropanoate: 7(s)

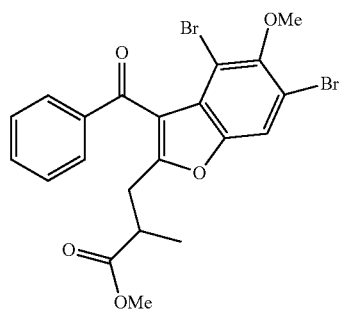 [SMILES: COC(=O)C(C)Cc1oc2cc(Br)c(OC)c(Br)c2c1C(=O)c1ccccc1]

In another typical embodiment, the invention provides synthesis of branched C2-alkylated benzofuran compounds of formula (8), comprises reaction of (5-methoxy-1-benzofuran-3-yl)(phenyl)methanone (6a) with ($C_1$-$C_6$)alkyl crotonate, in presence of $K_2CO_3$, Ru(PPh$_3$)$_3$Cl$_2$ and AgOAc, toluene at 140° C. (bath temperature) for 24 h, followed by cooling the reaction mixture to room temperature to obtain the crude products which is further purified by column chromatography (pet ether/AcOEt) to give mixture of branched and linear alkylated adducts (cf scheme 9).

Scheme 9:

Process for synthesis of branched C2 alkylated products:

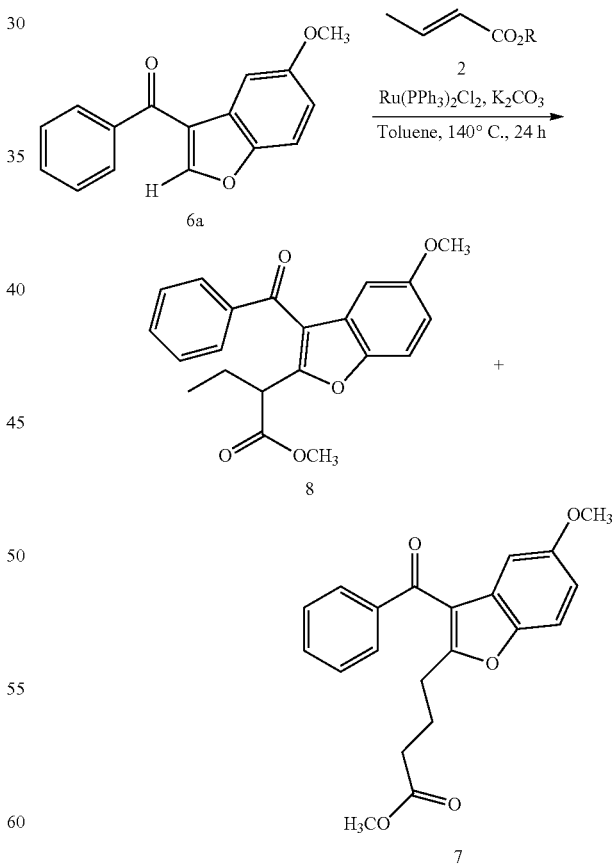

Similarly, branched C2 alkylated benzofuran compounds can be synthesized by using N-isopropylacrylamide in presence of $K_2CO_3$, Ru(PPh$_3$)$_3$Cl$_2$ and AgOAc, toluene at 140° C. (bath temperature) for 24 h, followed by cooling the reaction mixture to room temperature to obtain the crude products which is further purified by column chromatography (pet ether/AcOEt) to give mixture of branched and linear alkylated adducts (cf scheme 10).

Scheme 10:

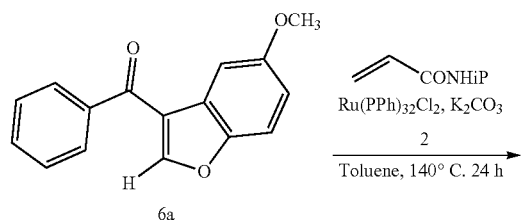

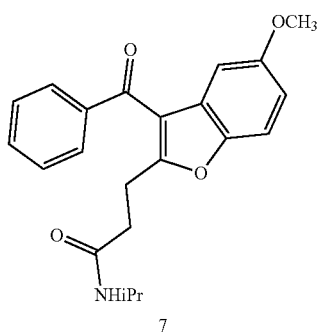

In yet another embodiment, the branched C2 alkylated products synthesized by the instant process encompass the following compounds;

i. Methyl 2-(5-methoxy-3-(4-methoxybenzoyl)benzofuran-2-yl)butanoate: 8(a)

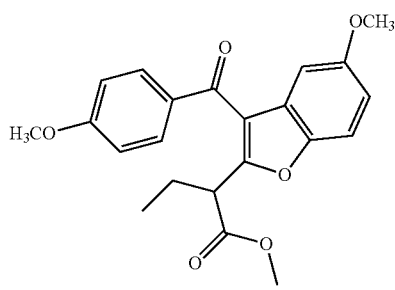 [SMILES: CCC(C(=O)OC)c1oc2ccc(OC)cc2c1C(=O)c1ccc(OC)cc1]

ii. Methyl 2-(3-benzoyl-5-methoxybenzofuran-2-yl)butanoate: 8(b)

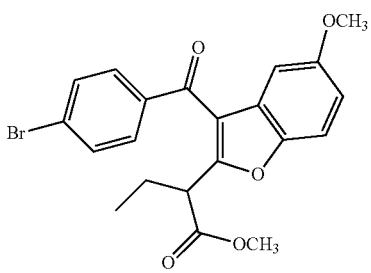 [SMILES: CCC(C(=O)OC)c1oc2ccc(OC)cc2c1C(=O)c1ccc(Br)cc1]

iii. Methyl 2-(3-benzoyl-5-methoxynaphtho[1,2-b]furan-2-yl)butanoate: 8(c)

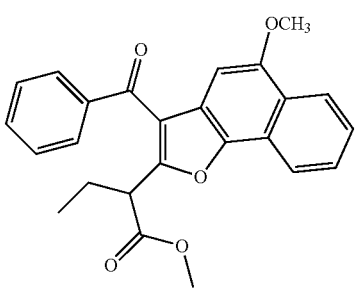 [SMILES: CCC(C(=O)OC)c1oc2c(cc(OC)c3ccccc32)c1C(=O)c1ccccc1]

iv. Methyl 2-(3-benzoyl-4,6-dibromo-5-methoxybenzofuran-2-yl)butanoate: 8(d)

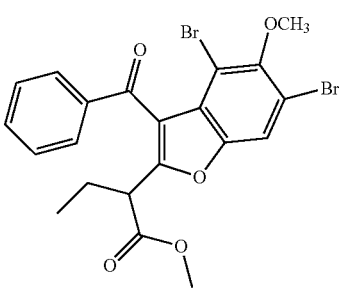 [SMILES: CCC(C(=O)OC)c1oc2cc(Br)c(OC)c(Br)c2c1C(=O)c1ccccc1]

v. N-isopropyl-2-(5-methoxy-3-(4-methoxybenzoyl)benzofuran-2-yl)propanamide: 8(e)

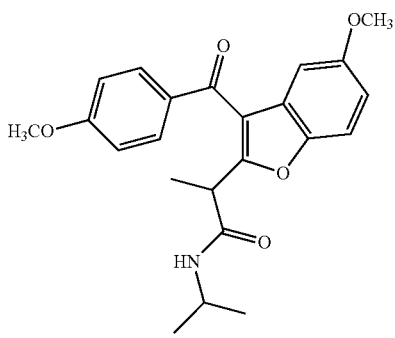 [SMILES: COc1ccc(C(=O)c2c(C(C)C(=O)NC(C)C)oc3ccc(OC)cc23)cc1]

vi. N-isopropyl-3-(5-methoxy-3-(4-methoxybenzoyl)benzofuran-2-yl)propanamide: 8(f)

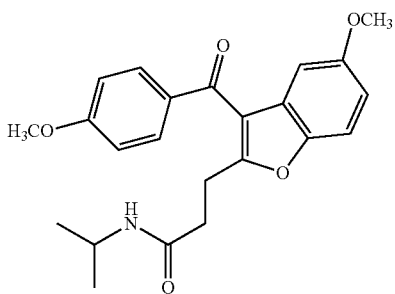 [SMILES: COc1ccc(C(=O)c2c(CCC(=O)NC(C)C)oc3ccc(OC)cc23)cc1]

vii. 2-(3-(4-bromobenzoyl)-5-methoxybenzofuran-2-yl)-N-isopropylpropanamide: 8(g)

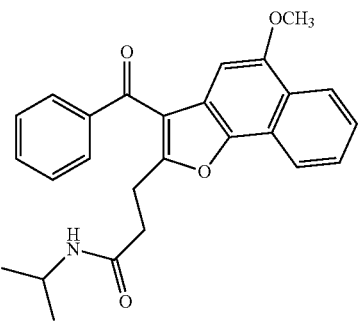

xi. 2-(3-benzoyl-5-methoxybenzofuran-2-yl)-N-isopropyl-propanamide: 8(k)

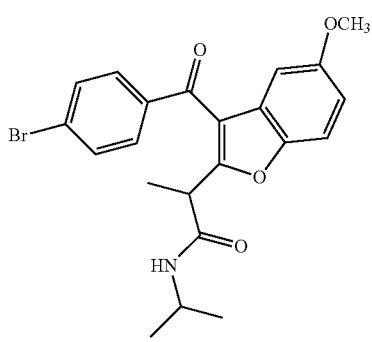 [SMILES: COc1ccc2oc(C(C)C(=O)NC(C)C)c(C(=O)c3ccc(Br)cc3)c2c1]

viii. 3-(3-(4-bromobenzoyl)-5-methoxybenzofuran-2-yl)-N-isopropylpropanamide: 8(h)

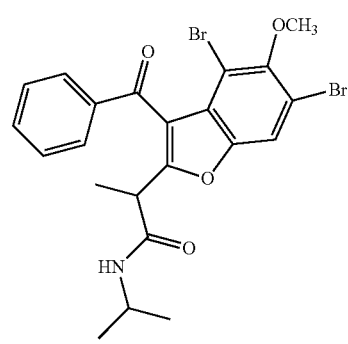

xii. 3-(3-benzoyl-4,6-dibromo-5-methoxybenzofuran-2-yl)-N-isopropylpropanamide: 8(l)

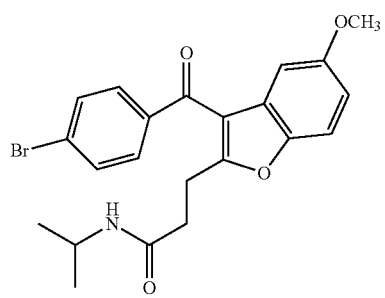 [SMILES: COc1ccc2oc(CCC(=O)NC(C)C)c(C(=O)c3ccc(Br)cc3)c2c1]

ix. 2-(3-benzoyl-5-methoxynaphtho[1,2-b]furan-2-yl)-N-isopropylpropanamide: 8(i)

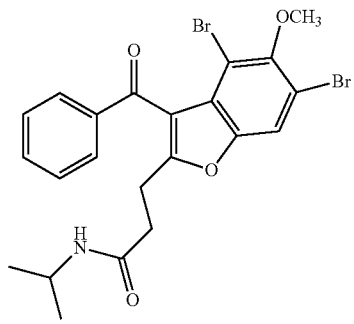

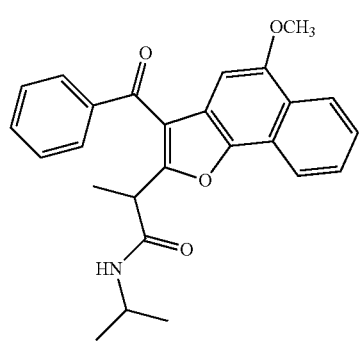 [SMILES: COc1cc2c(C(=O)c3ccccc3)c(C(C)C(=O)NC(C)C)oc2c2ccccc12]

x. 3-(3-benzoyl-5-methoxynaphtho[1,2-b]furan-2-yl)-N-isopropylpropanamide: 8(j)

In another embodiment, the present invention provides a pharmaceutical composition comprising effective amount of instant alkylated aroylbenzofuran compounds of formula III and IV or its pharmaceutically acceptable salts, along with pharmaceutically acceptable excipients or carriers, for the treatment of inflammation, cancer and parasitic infections in a mammal. The synthesized benzofuran compounds are act as anti-inflammatory, anti-cancer and anti-parasitic candidates.

Further the composition may be formulated into preparations like solid, semi-solid, liquid or gaseous forms, such as tablets, capsules, powders, granules, ointments, syrup, solutions, injections, gels and microspheres etc.

The pharmaceutical compositions of the invention can be prepared by combining a compound of the invention with an appropriate pharmaceutically acceptable carrier(s), diluent(s) or excipient(s).

In another embodiment, the present invention relates to administering 'an effective amount' of the 'composition of invention' to the subject suffering from inflammation. Accordingly, compound of the invention and pharmaceutical compositions containing them may be administered using any amount, any form of pharmaceutical composition via any route of administration effective for treating the disease. Typical routes of administering such pharmaceutical compositions include, without limitation, oral, topical, transdermal, inhalation, parenteral, sublingual, buccal, rectal, vaginal, and intranasal.

The invention provides method of treating inflammation, comprises administering an effective amount of aroylbenzofuran compounds or its pharmaceutical salt in association with one or more pharmaceutical carriers.

The said pharmaceutical compositions that will be administered to a subject or patient may take the form of one or more dosage units. The dosage forms can also be prepared as sustained, controlled, modified and immediate dosage forms.

The excipients or carriers are selected from the group such as diluents, disintegrants, crosslinked polymers, binders, lubricants, coatings layer.

Further the synergistic effect of instant pharmaceutical composition can be achieved in combination with additional known anti-inflammatory agents.

In yet another embodiment, the invention furnishes the use of instant aroylbenzofuran compounds for the preparation of medicament useful for treating inflammation diseases in mammal.

Advantages of Invention:
  a. A simple process for the preparation of antiinflammatory compounds.
  b. Efficient, regioselective, high yielding and requires less number of steps compared to currently available processes.
  c. The instant process is industrially viable, technically advanced The following examples, which include preferred embodiments, will serve to illustrate the practice of this invention, it being understood that the particulars shown are by way of examples and for purpose of illustrative discussion of preferred embodiments of the invention only and are not limiting the scope of the invention.

Experimental:
1. Acrylate Substrate Scope[a] is Depicted in Table 1;

TABLE 1

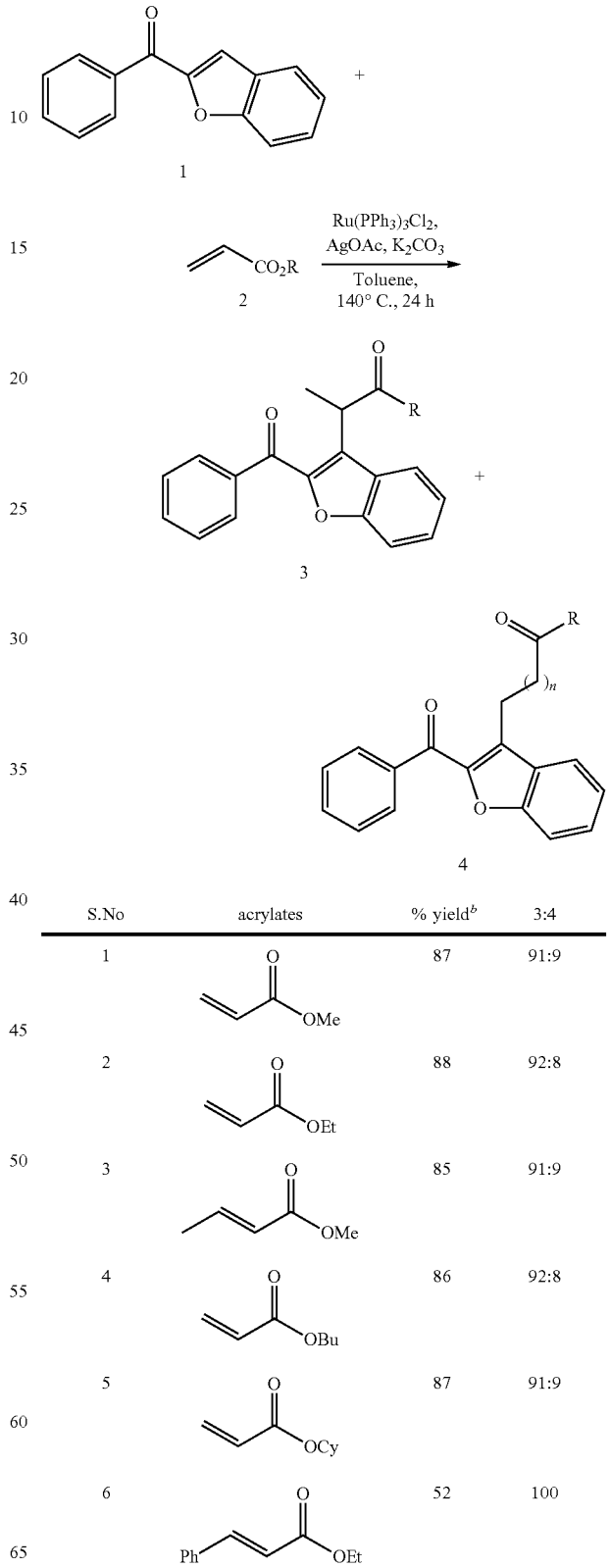

| S.No | acrylates | % yield[b] | 3:4 |
|---|---|---|---|
| 1 | OMe acrylate | 87 | 91:9 |
| 2 | OEt acrylate | 88 | 92:8 |
| 3 | OMe crotonate | 85 | 91:9 |
| 4 | OBu acrylate | 86 | 92:8 |
| 5 | OCy acrylate | 87 | 91:9 |
| 6 | Ph-OEt cinnamate | 52 | 100 |

TABLE 1-continued

[Reaction scheme: 2-benzoylbenzofuran (1) + acrylate CH₂=CH-CO₂R (2) with Ru(PPh₃)₃Cl₂, AgOAc, K₂CO₃, Toluene, 140° C., 24 h → branched product 3 + linear product 4]

| S.No | acrylates | % yield[b] | 3:4 |
|---|---|---|---|
| 7 | methacrylate OMe | 88[c] | 100 |
| 8 | methacrylate OBu | 86[c] | 100 |
| 9 | N-isopropyl acrylamide | 74[d] | 100 |

R = R₂ (formula-2)

[a]Reaction conditions: benzofuran (1 equiv), acrylate (3 equiv), Ru (PPh₃)Cl₂ (10 mol %), K₂CO₃ (3 equiv), Ag (OAc) (30 mol %), 140° C., solvent, 24h.
[b]isolated yield after column chromatographic purification.
[c]exclusively linear adduct,
[d]unreacted starting material (52%) has recovered 2. Scope of the Olefins or Alkanes in Branched Selective Alkylation is Described Herein Below Table 2;

TABLE 2

Scope of directing groups and olefins in branched selective alkylation[a,b]

[Reaction scheme: benzofuran-2-R₁ (1) + CH₂=CH-R₂' (2') → branched 3-(MeO₂C-CH(R₂')-) benzofuran-2-R₁ (3) + linear CH₂CH₂-CO₂Me derivative (4)]

| Entry | R₁ | R₂' | 3 | 4 |
|---|---|---|---|---|
| 1 | 1f (R₁ = —COCH₃) | CO₂Me (2a) | 3fa:4fa (1:1, 71%) | |
| 2 | 1g (R₁ = —CO₂Me) | CO₂Me (2a) | no reaction | |
| 3 | 1h (R₁ = —COOH) | CO₂Me (2a) | no reaction | |
| 4 | 1i (R₁ = —Ph) | CO₂Me (2a) | no reaction | |
| 5 | 1j (R₁ = —$^n$C₅H₂₁) | CO₂Me (2a) | no reaction | |
| 6 | 1a (R₁ = —COPh) | CN (2i) | no reaction | |
| 7 | 1a (R₁ = —COPh) | CONHIPr (2j) | 3aj (74%)[c] | |
| 8 | 1a (R₁ = —COPh) | COCH₃ (2k) | no reaction | |
| 9 | 1a (R₁ = —COPh) | Ph (2l) | 3al:4al (1:1, 83%) | |
| 10 | 1a (R₁ = —COPh) | C₁₀H₂₁ (2m) | | 4am (65%)[d] |

[a]Reaction conditions: 1 (1 mmol), 2 (3 mmol), Ru(PPh₃)₃Cl₂ (5 mol %), K₂CO₃ (3 mmol), AgOAc (30 mol %);
[b]isolated yield and ratio determined by ¹H NMR,
[c]based on 48% conversion of starting material;
[d]based on 42% conversion of starting material.

The compatibility of various other directing groups and also the olefins has been examined. As shown in Table 1, 2-alkyl-, 2-phenyl and 2-carboxylate derivatives are intact under these conditions and 2-acetyl benzofuran gave a ~1:1 mixture of linear/branched alkylation products. The olefin scope has been examined by employing N-isopropylacrylamide, acrylonitrile, methylvinyl ketone, styrene and dodecene as representative olefin partners and 2-benzoylbenzofuran (1a) as a substrate (entries 6-10, Table 1). The reactions with acrylonitrile and methylvinyl ketone were not found to be encouraged under these conditions. The reaction was sluggish with N-isopropyl acrylamide (74% yield based on 48% conversion). However, the reaction exclusively gave the branched product. On the other hand, with dodec-1-ene, the reaction was incomplete (65% yield based on 42% conversion), but interestingly, the reaction gave exclusively the linear alkylation product. A 1:1 regioisomeric mixture was obtained with styrene. These experiments revealed that the nature of directing group and also of the olefin has a directly influence on the branched vs linear selectivity.

3. Optimization of Process by Varying Reaction Parameters Such as Base, Solvent, Temperature and Additives which are Summarized in Table 3.

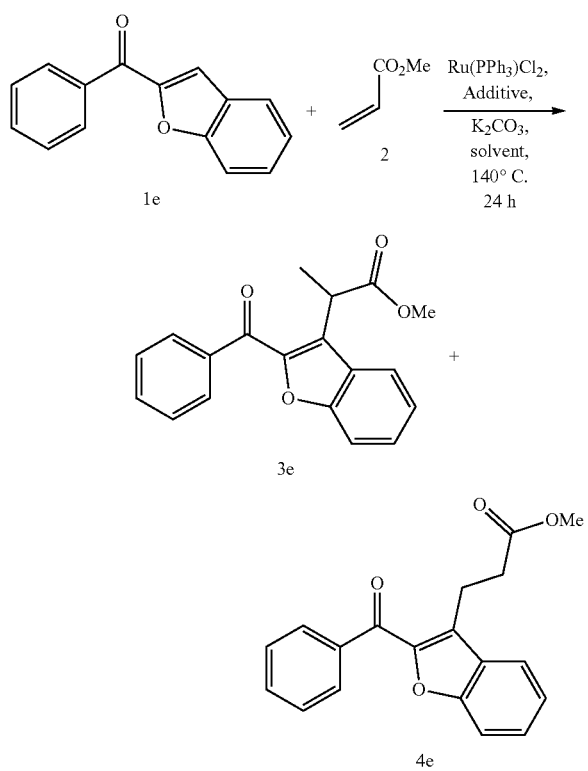

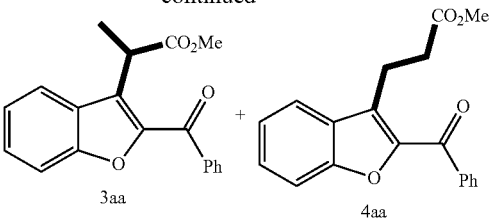

TABLE 4

| Entry | Catalyst | Additive | Yield % (3/4)[c] |
|---|---|---|---|
| 1 | [(p-cymene)RuCl$_2$]$_2$ [A][b] | AdCO$_2$H | 23 (28/72) |
| 2 | Ru$_3$(CO)$_{12}$[b] | AdCO$_2$H | 31 (83/17) |
| 3 | RuCl$_3$·H$_2$O[b] | AdCO$_2$H | complex mixture |
| 4 | RuO$_2$[b] | AdCO$_2$H | no reaction |
| 5 | (PPh$_3$)$_3$Ru(CO)H$_2$[b] | AdCO$_2$H | 73 (89/11) |
| 6 | Ru(PPh$_3$)$_3$Cl$_2$[B][b] | AdCO$_2$H | 82 (94/6) |
| 7 | 5 mol % B | PivCO$_2$H | 74 (91/9) |
| 8 | 5 mol % B | CCl$_3$CO$_2$H | 77 (96/4) |
| 9 | 5 mol % B | MesCO$_2$H | 72 (95/5) |
| 10 | 5 mol % B | Cu(OAc)$_2$ | 74 (94/6) |
| 11 | 5 mol % B | Ag(OAc) | 87 (94/6) |
| 12 | 5 mol % B | — | 61 (90/10) |
| 13[d] | 5 mol % B | Ag(OAc) | no reaction |
| 14[e] | 5 mol % B | Ag(OAc) | 56 (89/11) |
| 15[f] | 5 mol % B | Ag(OAc) | 63 (91/9) |
| 16[g] | 5 mol % B | Ag(OAc) | 86 (94/6) |

[a]Reaction conditions: 1a (1 mmol), methyl acrylate (3 mmol), K$_2$CO$_3$ (3 mmol, unless otherwise mentioned), additive (30 mol %);
[b]10 mol % catalyst,
[c]isolated yield and ratio determined by HPLC and/or $^1$H NMR;
amount of K$_2$CO$_3$ used—[d]0 eq.;[e]1 eq.;[f]2 eq.;[g]5 eq.

TABLE 3

Optimization studies[a]

| S.No | Base | Additive | Solvent | % Yield (3e/4e)[b] |
|---|---|---|---|---|
| 1. | K$_2$CO$_3$ (3 eq) | AdCO$_2$H | Dioxane | 76 (79/21) |
| 2. | K$_2$CO$_3$ (3 eq) | AdCO$_2$H | Toluene | 83 (87/13) |
| 3. | K$_2$CO$_3$ (3 eq) | PivCO$_2$H | Toluene | (91/9) |
| 4. | K$_2$CO$_3$ (3 eq) | CCl$_3$CO$_2$H | Toluene | (96/4) |
| 5. | K$_2$CO$_3$ (3 eq) | MesCO$_2$H | Toluene | (95/5) |
| 6. | K$_2$CO$_3$ (3 eq) | Cu(OAc)$_2$ | Toluene | (93/7) |
| 7. | K$_2$CO$_3$ (3 eq) | Ag(OAc) | Toluene | 87 (94/6$^d$) |
| 8. | K$_2$CO$_3$ (3 eq) | No additive | Toluene | (90/10$^c$) |

[a]Reaction conditions: benzofuran (1 equiv), methacrylate (3 equiv), Ru (PPh$_3$)Cl$_2$ (10 mol %), K$_2$CO$_3$ (3 equiv), Additive (30 mol %), 140° C., solvent, 24 h.
$^b$isolated yield after column chromatographic purification.
$^c$recovered unreacted starting material.
$^d$clean reaction.

4. Optimization of Reaction Conditions for Directed Hydroarylation[a] is Disclosed to Table 4.

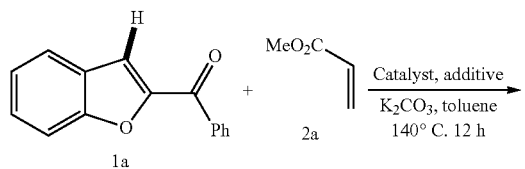

Initial exploratory experiments have been carried, out using benzo[b]furan 1a as the substrate and methyl acrylate 2a as an acceptor. In general, the cationic ruthenium complexes in combination with an oxidant, have been used for the alkenylations. In anticipation of the requisite alkylation, various neutral ruthenium complexes have been explored in this pursuit using adamantane-1-carboxylic acid (AdCO$_2$H) (entries 1-6, Table 3) as an additive. The employed conditions in the exploratory experiments involved the heating of a mixture of 1a with excess acrylate (3 eq.) in the presence of the catalyst (10 mol %), K$_2$CO$_3$ (3.0 eq.) and adamantane-1-carboxylic acid (AdCO$_2$H, 0.3 eq.) in toluene at 140° C. for 12 h in a screw-capped sealed tube. These preliminary experiments revealed that the desired alkylation of 1a was viable. Further the formation of substantial amounts of branched alkylated products has been noticed. The ratio of linear vs branched products seems to be catalyst dependent. Among the various ruthenium complexes screened, the best branched selectivity was obtained with Ru$_3$(CO)$_{12}$, RuH$_2$(CO)(PPh$_3$)$_3$ and Ru(PPh$_3$)$_3$Cl$_2$.

Considerations of the cost, stability and the good yield obtained, when compared with the Ru$_3$(CO)$_{12}$ and RuH$_2$(CO)(PPh$_3$)$_3$ complexes, led us to select the Ru(PPh$_3$)$_3$Cl$_2$ complex for further optimization studies. The optimization experiments were carried out using 5 mol % catalysts, 3 equivalents of K$_2$CO$_3$ and 30 mol % of additive (entries 7-11, Table 3). Silver acetate has been found to be the best additive for improving the selectivity and consequently the products were isolated in excellent yield. Coming to the solvents screened, DMSO, DMF and DCE were found to be completely ineffective. Reduction of the keto group was observed when NMP was used as the solvent. In 1,4-dioxane, the reaction gave good yield, but the selectivity was reduced. Thus, toluene has been identified as the solvent of choice for which both the yield and the selectivity were found to be the best. Control experiments revealed that the reaction also proceeds without AgOAc (entry 12, Table 3), but with a high increase in the amount of intractable compounds in the mixture. Experiments with varying concentrations of $K_2CO_3$ revealed that its presence is essential (entries 13-16, Table 3).

5. Optimization of Reaction Conditions Using $Ru(PPh_3)_3Cl_2$ Complex[a]

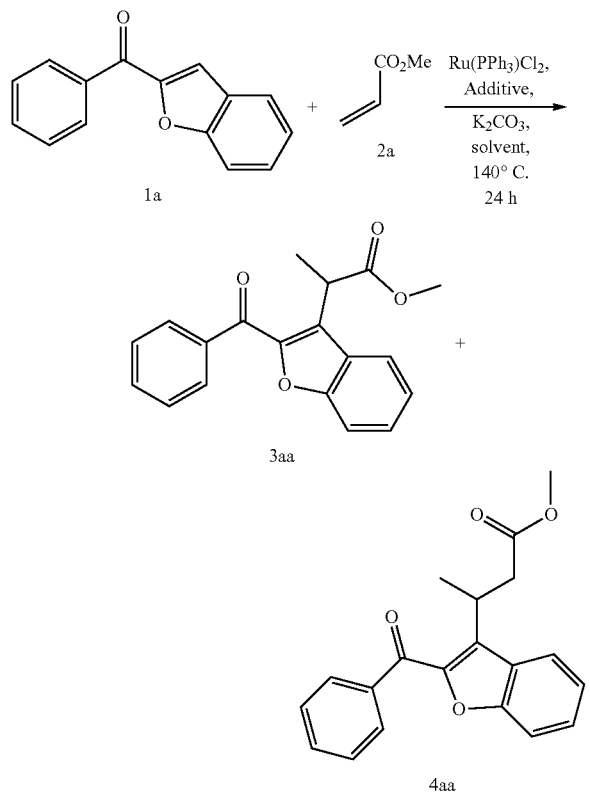

TABLE 5

| S.No | Additive | Solvent | Base | Yield % (3/4)[b] |
|---|---|---|---|---|
| 1. | $PivCO_2H$ | Toluene | $K_2CO_3$ | 74 (91/9) |
| 2. | $CCl_3CO_2H$ | Toluene | $K_2CO_3$ | 77 (96/4) |
| 3. | $MesCO_2H$ | Toluene | $K_2CO_3$ | 72 (95/5) |
| 4. | $Cu(OAc)_2$ | Toluene | $K_2CO_3$ | 74 (94/6) |
| 5. | Ag(OAc) | Toluene | $K_2CO_3$ | 87 (94/6) |
| 6. | No additive | Toluene | $K_2CO_3$ | 61 (90/10)[c] |
| 7. | Ag(OAc) | DMSO | $K_2CO_3$ | complex mixture |
| 8. | Ag(OAc) | DMF | $K_2CO_3$ | complex mixture |
| 9. | Ag(OAc) | DCE | $K_2CO_3$ | 0[d] |
| 10. | Ag(OAc) | NMP | $K_2CO_3$ | 0[e] |
| 11. | Ag(OAc) | Dioxane | $K_2CO_3$ | 67 (79/21) |

[a]Reaction conditions: benzofuran (1 equiv), methylacrylate (3 equiv), $Ru(PPh_3)_3Cl_2$ catalyst (10 mol %), $K_2CO_3$ (unless otherwise mentioned, 3 equivalents with respect to 1a), Additive (30 mol %), 140° C., solvent, 24 h;
[b]isolated yield after column chromatographic purification;
[c]intractable compounds increased in the reaction mixture;
[d]recovered unreacted starting material;
[e]keto group was reduced;

6. HPLC Method

The HPLC was equipped with a Sunfire-C-18, RP 4.6× 250 mm, 5 μm column maintained at a temperature of 20° C. The mobile phase that gave adequate separation between the branched and linear products was found to be 85% methanol, 15% water with a flow rate of 1.0 mL/min. Note that all solvents were HPLC grade. The volume of sample injected was set at 10-25 μL. The runtime for each sample was 30 minutes and retention time/area of the products are given in Table 6.

TABLE 6

Retention time/area of the products (with $[Ru(p-cymene)Cl_2]_2$) in the HPLC chromatogram

| | | Retention time/area % | |
|---|---|---|---|
| S.No | | Branched (3) | Linear (4) |
| 1. | | 3aa (7.039/14.39) | 4aa (7.417/85.61) |
| 2. | | 3ab (8.209/12.11) | 4ab (8.800/87.89) |
| 3. | | 3ac (12.40/13.99) | 4ac (13.772/86.01) |
| 4. | | 3ba (7.647/14.14) | 4ba (8.166/85.86) |
| 5. | | 3bb (8.780/23.03) | 4bb (9.485/76.97) |
| 6. | | 3ca (7.623/27.30) | 4ca (8.626/72.70) |
| 7. | | 3cb (8.820/39.96) | 4cb (10.329/60.04) |
| 8. | | 3da (8.599/17.74) | 4da (9.381/82.26) |
| 9. | | 3db (10.115/5.41) | 4db (11.201/94.59) |
| 10. | | 3ea (9.405/8.15) | 4ea (10.034/91.85) |
| 11 | | 3eb (11.059/6.95) | 4eb (11.882/93.05) |

7. Optimization of Catalyst, Additive and Solvent for C2 Alkylation of 3-Aroylbenzofurans Table 7.

Iridium, Rhodium catalyst were screened by the inventors for the desired alkylation, but were not successful. Then again moved to ruthenium catalyst, among several ruthenium catalyst screened satisfactory results was obtained using $Ru(PPh_3)_3Cl_2$ catalyst. Further different additives like $Ad_2CO_2H$, pivalic acid, $Cu(OAc)_2.H_2O$, $CCl_3CO_2H$ and Ag(OAc) were screened. Among these, satisfactory results were obtained using Ag(OAc) as an additive. The reaction was then screened in different solvents like 1,4-Dioaxane, DMSO, NMP, Toluene, where Toluene was found suitable solvent for the desired alkylation.

TABLE 7

| S.No | Catalyst | Additive | Solvent | % yield |
|---|---|---|---|---|
| 1. | $[Ir(COD)(Py)PCy_3]PF_6$ | — | Toluene | N.R |
| 2. | $Rh(PPh_3)Cl_2$ | Ag(OAc) | Toluene | N.R |
| 3. | $Ru_3(CO)l_2$ | Ag(OAc) | Toluene | 81% (58:42)[a] |
| 4. | $RuCOH_2(PPh_3)_3$ | Ag(OAc) | Toluene | 60% |
| 5. | $Ru(PPh_3)Cl_2$ | Ag(OAc) | Toluene | 87% |
| 6. | $Ru(PPh_3)Cl_2$ | Pivalic acid | Toluene | 84% (13:87)[a] |
| 7. | $Ru(PPh_3)Cl_2$ | $AdCO_2H$ | Toluene | 49% |
| 8. | $Ru(PPh_3)Cl_2$ | $Cu(OAc)_2.H2O$ | Toluene | 57% |
| 9. | $Ru(PPh_3)Cl_2$ | $CCl_3CO_2H$ | Toluene | 73% (22% S.M) |
| 10. | $Ru(PPh_3)Cl_2$ | Ag(OAc) | DMSO | Complex mixture |
| 11. | $Ru(PPh_3)Cl_2$ | Ag(OAc) | Dioxane | 57% (16% S.M) |

N.R = No Reaction,
S.M = starting material,
[a]= Linear to branched ratio

EXAMPLES

Example: 1

Preparation of Starting Materials

Preparation of 2-Aroyl benzofurans

All 2-aroyl benzofurans were synthesized from the corresponding Acetophenones and salicyaldehyde according to the literature procedures. The obtained compounds were purified by silica gel column chromatography (e.g. eluent: pet ether/EtOAc=96/4). Spectral data for these compounds showed coincidence with the literature data:

Example: 2

General Procedure for Synthesis of 2-aroyl benzofuran

To a solution of acetophenone (1.2 eq) in acetone was added $K_2CO_3$ (4 eq) and the appropriate salicylaldehyde (1 eq) under argon. The resulting mixture was stirred at reflux for 20 h. After removal of the solvent water and ethylacetate was added to the residue. The aqueous layer was extracted two times with ethylacetate and combined organic layers was dried over sodium sulphate and concentrated. The crude residue was purified by column chromatography and characterized by NMR and mass spectrometry technique, then compared with literature data.

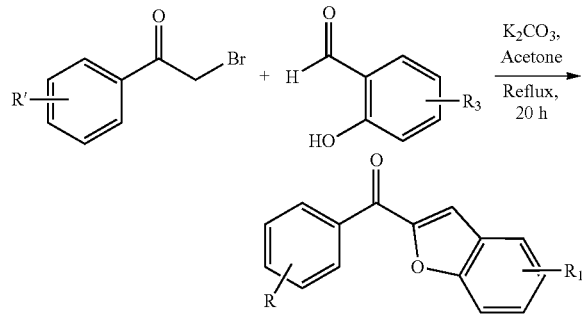

Example: 3

General Procedure for Products 3

Method A:

Ru(PPh$_3$)$_3$Cl$_2$ (0.01 mmol) and AgOAc (0.03 mmol) were placed in a screw-cap pressure tube, which was then evacuated and back filled with argon. To the reaction vessel were added 2-aroylbenzofuran 1 (0.1 mmol), alkene 2' (0.3 mmol), $K_2CO_3$ (0.3 mmol), and toluene (2 mL), unless otherwise noted. The solution was then stirred at 140° C. (bath temperature) for 24 h. The mixture of the reaction was cooled to room temperature. The solvent were evaporated and the crude products were purified by column chromatography to give analytically pure 3.

Method B:

2-aroylbenzo[b]furan (0.1 mmol) was placed in a screw cap pressure tube and dissolved in anhydrous toluene, which was then evacuated and back filled with argon. To the reaction vessel alkene (acrylate) 2 (0.3 mmol), $K_2CO_3$ (0.3 mmol), Ru(PPh$_3$)$_3$Cl$_2$ (0.01 mmol) and AgOAc (0.03 mmol) were added. The solution was then stirred at 140° C. (bath temperature) for 24 h. The reaction mixture was cooled to room temperature. The solvent were evaporated and the crude products were purified by column chromatography 100-200 mesh (pet ether/AcOEt) to give analytically pure.

The compounds prepared according to the invention are listed below:

Example: 4

Methyl 2-(2-benzoylbenzofuran-3-yl)propanoate (3a)

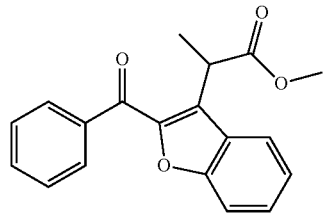 [SMILES: COC(=O)C(C)c1c(C(=O)c2ccccc2)oc2ccccc12]

Isolated by column chromatography (pet ether/AcOEt=9:1, Rf=0.5). The title compound was determined as colourless oil (87%), and the ratio of branch to linear product is (91:9); $^1$H NMR (200 MHz, CDCl$_3$): δ 1.67 (d, J=7.2 Hz, 3H), 3.68 (s, 3H), 4.96 (q, J=7.2 Hz, 1H), 7.32 (ddd, J=1.4, 6.8, 8.1 Hz, 1H), 7.45-7.68 (m, 5H), 7.75 (d, J=8.0 Hz, 1H), 8.13 (dd, J=1.6, 8.5 Hz, 2H) ppm; $^{13}$C NMR (50 MHz, CDCl$_3$): δ 16.8 (q), 35.9 (d), 52.1 (q), 112.5 (d), 122.25 (d), 123.7 (d), 126.7 (s), 128.1 (d), 128.3 (d, 2C), 128.8 (s), 129.9 (d, 2C), 132.9 (d), 137.3 (s), 147.7 (s), 154.3 (s), 173.7 (s), 185.9 (s) ppm; IR (cm$^{-1}$): 3020, 2400, 1735, 1645, 1563, 1261, 1215, 1059, 877, 757, 669; HRMS (ESI) calcd for $C_{19}H_{17}O_4Na$ (M$^+$+Na): 331.0941; found: 331.0938.

Example: 5

Ethyl 2-(2-benzoylbenzofuran-3-yl)propanoate (3b)

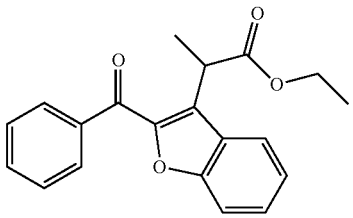 [SMILES: CCOC(=O)C(C)c1c(C(=O)c2ccccc2)oc2ccccc12]

Isolated by column chromatography (pet ether/AcOEt=9:1, Rf=0.5). The title compound was determined as colourless oil (88%), and the ratio of branch to linear product is (92:8); $^1$H NMR (200 MHz, CDCl$_3$): δ 1.15 (t, J=7.2 Hz, 3H), 1.67 (d, J=7.3 Hz, 3H), 4.16 (q, J=7.2 Hz, 2H), 4.90 (t, J=7.3 Hz, 1H), 7.32 (ddd, J=1.4, 6.8, 8.1 Hz, 1H), 7.44-7.67 (m, 5H), 7.77 (d, J=8.0 Hz, 1H), 8.11 (dd, J=1.6, 8.3 Hz, 2H) ppm; $^{13}$C NMR (50 MHz, CDCl$_3$): δ 14.1 (q), 16.9 (q), 36.1 (d), 61.0 (t), 112.4 (d), 122.3 (d), 123.5 (d), 126.7 (s), 128.0 (d), 128.3 (d, 2C), 129.0 (s), 129.9 (d, 2C), 132.9 (d), 137.4 (s), 147.7 (s), 154.3 (s), 173.7 (s), 185.8 (s) ppm; IR (cm$^{-1}$): 3278, 3061, 2984, 1908, 1732, 1645, 1599, 1448, 1300, 1200, 1093, 876, 752, 680; HRMS (ESI) calcd for $C_{20}H_{18}O_4Na$ (M$^+$+Na): 345.1097; found: 345.1095.

Example: 6

Methyl 2-(2-benzoylbenzofuran-3-yl)butanoate (3c)

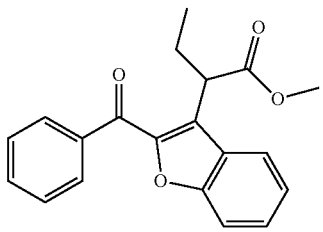 [SMILES: CCC(C(=O)OC)c1c(C(=O)c2ccccc2)oc2ccccc12]

Isolated by column chromatography (pet ether/AcOEt=9:1, Rf=0.5). The title compound was determined as colourless oil (85%), and the ratio of branch to linear product is (91:11); $^1$H NMR (200 MHz, CDCl$_3$): δ 0.94 (t, J=7.5 Hz, 3H), 1.91-2.13 (m, 1H), 2.26-2.47 (m, 1H), 3.67 (s, 3H), 4.84 (dd, J=6.7, 8.6 Hz, 2H), 7.32 (dt, J=1.3, 8.6 Hz, 1H), 7.44-7.67 (m, 5H), 7.84 (d, J=7.6 Hz, 1H), 8.10 (dd, J=1.6, 6.7 Hz, 2H) ppm; $^{13}$C NMR (50 MHz, CDCl$_3$): δ 12.0 (q), 24.8 (t), 42.9 (d), 52.1 (q), 112.4 (d), 122.9 (d), 123.6 (d), 126.9 (s), 127.0 (s), 128.0 (d), 128.3 (d, 2C), 129.9 (d, 2C), 132.9 (d), 137.4 (s), 148.5 (s), 154.3 (s), 173.3 (s), 185.9 (s) ppm; IR (cm$^{-1}$): 3279, 3060, 2968, 1944, 1734, 1647, 1598, 1447, 1361, 1264, 1112, 1002, 979, 875, 752, 680; HRMS (ESI) calcd for C$_{20}$H$_{18}$O$_4$Na (M$^+$+Na): 345.1097; found: 345.1095.

Example: 7

Butyl 2-(2-benzoylbenzofuran-3-yl)propanoate (3d)

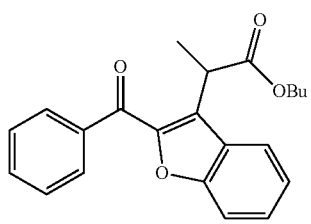

Isolated by column chromatography (pet ether/AcOEt=9:1, Rf=0.5). The title compound was determined as colourless oil (86%), and the ratio of branch to linear product is (92:8); $^1$H NMR (400 MHz, CDCl$_3$): δ 0.79 (t, J=7.3 Hz, 3H), 1.13-1.34 (m, 2H), 1.36-1.57 (m, 2H), 1.68 (d, J=6.87 Hz, 3H), 4.11 (t, J=6.64 Hz, 2H), 4.92 (q, J=7.33 Hz, 1H), 7.33 (td, J=0.92, 7.56 Hz, 1H), 7.50 (ddd, J=1.4, 7.3, 8.9 Hz, 1H), 7.53-7.58 (m, 3H), 7.64 (tt, J=1.4, 7.8 Hz, 1H), 7.77 (d, J=7.8 Hz, 1H), 8.11 (d, J=1.4 Hz, 1H), 8.12 (d, J=7.3 Hz, 1H) ppm; $^{13}$C NMR (101 MHz, CDCl$_3$): δ ppm 13.5 (q) 16.8 (q) 18.9 (t) 30.5 (t) 36.1 (d) 64.9 (t) 112.4 (d) 122.4 (d) 123.6 (d) 126.8 (s) 128.1 (d) 128.3 (d, 2C) 129.0 (s) 129.9 (d, 2C) 132.9 (d) 137.4 (s) 147.7 (s) 154.4 (s) 173.3 (s) 185.9 (s). IR (cm$^{-1}$): 3393, 2959, 1735, 1647, 1448, 1300, 1260, 876, 751, 724; HRMS (ESI) calcd for C$_{22}$H$_{23}$O$_4$ (M$^+$+H): 351.1591; found: 351.1589.

Example: 8

Cyclohexyl 2-(2-benzoylbenzofuran-3-yl)propanoate (3e)

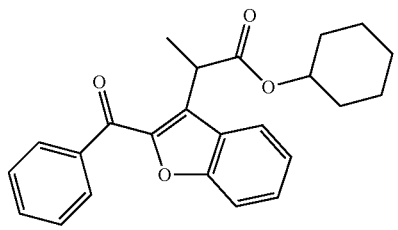 [SMILES: CC(C(=O)OC1CCCCC1)c1c(C(=O)c2ccccc2)oc2ccccc12]

Isolated by column chromatography (pet ether/AcOEt=9:1, Rf=0.5). The title compound was determined as colourless oil (87%), and the ratio of branch to linear product is (91:9) was determined by $^1$H NMR (500 MHz, CDCl$_3$): δ 1.14-1.47 (m, 8H), 1.63-1.65 (m, 1H), 1.66 (d, J=7.3 Hz, 3H), 1.80-1.83 (m, 1H), 4.81-4.86 (m, 1H), 4.87 (q, J=7.3 Hz, 2H), 7.31 (dt, J=0.6, 7.9 Hz, 1H), 7.48 (ddd, J=1.2, 7.3 Hz, 1H), 7.52-7.56 (m, 3H), 7.63 (tt, J=1.2, 7.9 Hz, 1H), 7.77 (d, J=7.9 Hz, 1H), 8.10 (d, J=1.2 Hz, 1H), 8.11 (d, J=7.3 Hz, 1H) ppm; $^{13}$C NMR (125 MHz, CDCl$_3$): δ 16.9 (q), 23.4 (t), 23.6 (t), 25.3 (t), 31.2 (t), 31.4 (t), 36.4 (d), 73.2 (d), 112.4 (d), 122.6 (d), 123.5 (d), 126.8 (s), 128.0 (d), 128.3 (d, 2C), 129.2 (s), 129.9 (d, 2C), 132.9 (d), 137.5 (s), 147.7 (s), 154.4 (s), 172.6 (s), 185.9 (s) ppm; IR (cm$^{-1}$): 2936, 2858, 1729, 1648, 1560, 1448, 1298, 1201, 1017, 876, 750, 723; HRMS (ESI) calcd for C$_{24}$H$_{25}$O$_4$ (M$^+$+H): 377.1747; found: 377.1746.

Example: 9

2-(2-benzoylbenzofuran-3-yl)-N isopropylpropanamide (3i)

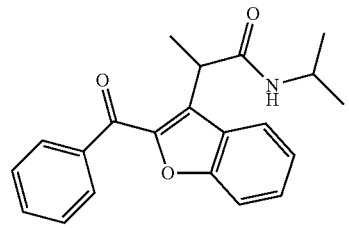 [SMILES: CC(C)NC(=O)C(C)c1c(C(=O)c2ccccc2)oc2ccccc12]

Isolated by column chromatography (pet ether/AcOEt=9:1, Rf=0.5). The title compound was determined as colourless oil (74%), and the ratio of (100) was determined by $^1$H NMR (500 MHz, CDCl$_3$): δ ppm 0.97 (d, J=6.7 Hz, 3H), 1.19 (d, J=6.7 Hz, 3H), 1.69 (d, J=7.3 Hz, 3H), 4.02 (dq, J=13.9, 6.7 Hz, 1H), 4.64 (q, J=7.1 Hz, 1H), 6.57 (d, J=7.3 Hz, 1H), 7.31-7.36 (m, 1H), 7.46-7.51 (m, 1H), 7.52-7.54 (m, 1H), 7.55-7.59 (m, 2H), 7.64-7.69 (m, 1H), 8.09 (d, J=7.9 Hz, 1H), 8.12-8.16 (m, 2H), $^{13}$C NMR (126 MHz, CDCl$_3$): δ ppm 15.8 (q), 22.44 (q), 22.71 (q), 37.29 (d), 41.43 (d), 112.2 (d), 123.7 (d), 124.2 (d), 126.5 (s), 128.3 (d), 128.4 (d, 2C), 130.2 (d, 2C), 131.0 (s), 133.3 (d), 136.9 (s), 147.8 (s), 154.6 (s), 171.2 (s), 186.7 (s); IR (cm$^{-1}$): 3333, 3061, 2973, 1644, 1549, 1449, 1360, 1261, 1174, 1023, 966, 826, 752; HRMS (ESI) calcd for $C_{21}H_{21}O_3NNa$ (M$^+$+Na): 358.1414; found: 358.1411.

Example: 10

Ethyl 2-(2-benzoylbenzofuran-3-yl)-3-phenylpropanoate (3f)

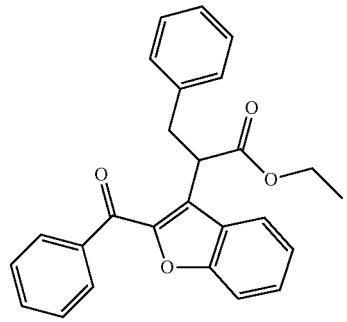 [SMILES: CCOC(=O)C(Cc1ccccc1)c1c(C(=O)c2ccccc2)oc2ccccc12]

Isolated by column chromatography (pet ether/AcOEt=9:1, Rf=0.5). The title compound was determined as colourless oil (74%), and the ratio of branch to linear product is (100) was determined by $^1$H NMR (500 MHz, CDCl$_3$) δ ppm 1.13 (t, J=7.3 Hz, 3H), 3.22 (dd, J=8.2, 13.3 Hz, 1H), 3.63 (dd, J=7.3, 13.3 Hz, 1H), 4.15 (dq, J=2.8, 13.9, 6.7 Hz, 2H), 5.15 (dd, J=6.9, 8.2 Hz, 1H), 7.04-7.13 (m, 5H), 7.31 (m, 1H), 7.45-7.50 (m, 3H), 7.52 (d, J=8.2 Hz, 1H), 7.57-7.61 (m, 2H), 7.85 (d, J=8.2 Hz, 1H), 7.87-7.90 (m, 2H), $^{13}$C NMR (126 MHz, CDCl$_3$): δ ppm 14.1 (q), 37.7 (q), 43.5 (q), 61.2 (d), 112.4 (d), 122.8 (d), 123.6 (d), 126.3 (d), 126.8 (s), 127.9 (s), 128.1 (d, 2C), 128.2 (d, 3C), 129.0 (d, 2C), 129.7 (d, 2C), 132.8 (d), 137.4 (s), 138.5 (s), 148.5 (s), 154.2 (s), 172.2 (s), 185.9 (s) ppm; IR (cm$^{-1}$) 3333, 3061, 2973, 1644, 1549, 1449, 1360, 1261, 1174, 1023, 966, 826, 752; HRMS (ESI) calcd for $C_{21}H_{21}O_3NNa$ (M$^+$+Na): 358.1414; found: 358.1411.

Example: 11

Methyl 3-(2-benzoylbenzofuran-3-yl)-2-methylpropanoate (3g)

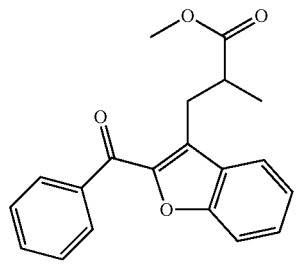 [SMILES: COC(=O)C(C)Cc1c(C(=O)c2ccccc2)oc2ccccc12]

Isolated by column chromatography (pet ether/AcOEt=9:1, Rf=0.5). The title compound was determined as colourless oil (88%), and the ratio of branch to linear product is (100) was determined by $^1$H NMR (400 MHz, CDCl$_3$) δ ppm 1.29 (d, J=6.9 Hz, 3H), 3.02-3.11 (m, 1H), 3.33 (dd, J=7.3, 13.3 Hz, 1H), 3.46 (dd, J=7.3, 13.3 Hz, 1H), 3.56 (s, 3H), 7.35 (dt, J=1.4, 8.2 Hz, 1H), 7.50 (dt, J=1.4, 8.2 Hz, 1H), 7.55 (d, J=7.8 Hz, 2H) 7.61-7.65 (m, 1H), 7.77 (d, J=7.79 Hz, 1H) 8.12 (d, J=7.8 Hz, 1H), 8.13 (d, J=7.3 Hz, 1H); $^{13}$C NMR (100 MHz, CDCl$_3$): δ ppm 17.4 (q), 28.4 (t), 39.9 (d), 51.7 (q), 112.3 (d) 121.9 (d) 123.5 (d) 128.2 (d) 128.3 (d, 2C) 128.6 (s) 128.8 (s) 129.8 (d, 2C) 132.7 (d) 137.54 (s) 148.66 (s) 154.19 (s) 176.47 (s) 185.55 (s); IR (cm$^{-1}$): 3061, 2950, 1735, 1644, 1598, 1558, 1447, 1373, 1291, 1267, 1171, 974, 875, 750, 722, 693; HRMS (ESI) calcd for $C_{20}H_{18}O_4Na$ (M$^+$+Na): 345.1097; found: 345.1094.

Example: 12

Butyl 3-(2-benzoylbenzofuran-3-yl)-2-methylpropanoate (3h)

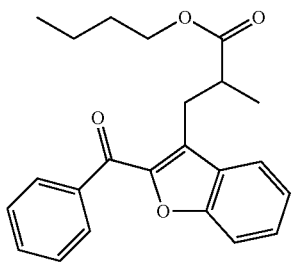 [SMILES: CCCCOC(=O)C(C)Cc1c(C(=O)c2ccccc2)oc2ccccc12]

Isolated by column chromatography (pet ether/AcOEt=9:1, Rf=0.5). The title compound was determined as colourless oil (86%), and the ratio of branch to linear product is (100) was determined by $^1$H NMR (400 MHz, CDCl$_3$) δ ppm 0.83 (t, J=7.3 Hz, 3H), 1.19 (dqd, J=14.94, 7.38, 7.38, 7.38, 3.21 Hz, 2H), 1.29 (d, J=6.9 Hz, 3H) 1.37-1.46 (m, 2H), 3.05 (qd, J=7.3 Hz, 1H), 3.33 (dd, J=6.9, 13.3 Hz, 1H), 3.43 (dd, J=8.2, 13.3 Hz, 1H), 3.88-3.99 (m, 2H), 7.35 (td, J=1.14, 7.44 Hz, 1H) 7.50 (ddd, J=1.4, 6.9, 8.2 Hz, 1H), 7.53-7.57 (m, 3H); 7.63 (tt, J=1.4, 7.3 Hz, 1H), 7.77 (d, J=7.8 Hz, 1H), 8.11-8.15 (m, 2H); $^{13}$C NMR (101 MHz, CDCl$_3$) d ppm 13.6 (q), 17.5 (q), 18.9 (t), 28.5 (t), 30.4 (t), 40.0 (d), 64.3 (t), 112.2 (d), 122.0 (d), 123.5 (d), 128.2 (s), 128.3 (d, 2C), 128.6 (s), 129.0 (s), 129.8 (s, 2C), 132.7 (d), 137.6 (s), 148.6 (s), 154.2 (s), 176.2 (s), 185.5 (s); IR (cm$^{-1}$): 3061, 2960, 1908, 1731, 1644, 1557, 1448, 1373, 1291, 1173, 976, 875, 750, 693; HRMS (ESI) calcd for $C_{23}H_{24}O_4Na$ (M$^+$+Na): 387.1567; found: 387.1563.

Example: 13

Methyl 2-(2-(4-fluorobenzoyl)benzofuran-3-yl)butanoate (3l)

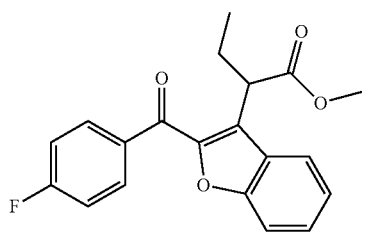 [SMILES: CCC(C(=O)OC)c1c(C(=O)c2ccc(F)cc2)oc2ccccc12]

Isolated by column chromatography (pet ether/AcOEt=9:1, Rf=0.5). The title compound was determined as colourless oil (90%), and the ratio of branch to linear product is (87:13) was determined by $^1$H NMR (200 MHz, CDCl$_3$): δ 0.94 (t, J=7.5 Hz, 3H), 1.91-2.13 (m, 1H), 2.26-2.48 (m, 1H), 3.67 (s, 3H), 4.84 (dd, J=6.7, 8.7 Hz, 2H), 7.18 (tdd, J=2.9, 1.3, 8.6 Hz, 1H), 7.32 (ddd, J=1.4, 6.7, 8.1 Hz, 1H), 7.50 (dt, J=1.3, 8.3 Hz, 2H), 7.57 (d, J=7.7 Hz, 1H), 7.85 (d, J=7.8 Hz, 1H), 8.15 (td, J=2.2, 5.4 Hz, 1H), 8.20 (td, J=2.2, 5.4 Hz, 1H) ppm; $^{13}$C NMR (50 MHz, CDCl$_3$): δ 12.1 (q), 24.8 (t), 42.9 (d), 52.1 (q), 112.3 (d), 115.5 (d, J=22.0 Hz, 2C), 123.0 (d), 123.7 (d), 126.9 (s), 127.4 (s), 128.2 (d), 132.6 (d, J=9.2 Hz, 2C), 133.7 (s), 148.3 (s), 154.3 (s), 165.1 (s, J=254.7 Hz), 168.1 (s), 173.2 (s), 184.2 (s) ppm; IR (cm$^{-1}$): 3073, 2968, 1944, 1737, 1647, 1599, 1560, 1435, 1263, 1231, 1158, 980, 877, 749, 625; HRMS (ESI) calcd for C$_{20}$H$_{17}$O$_4$FNa (M$^+$+Na): 363.1003; found: 363.1001.

Example: 14

Methyl 2-(2-(4-fluorobenzoyl)benzofuran-3-yl)butanoate

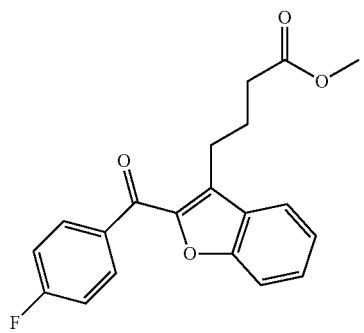 [SMILES: COC(=O)CCCc1c(C(=O)c2ccc(F)cc2)oc2ccccc12]

Isolated by column chromatography (pet ether/AcOEt=9:1, Rf=0.5). The title compound was determined as colourless oil (87%), and the ratio of branch to linear product is (88:12) was determined by $^1$H NMR (200 MHz, CDCl$_3$): δ 2.10 (qt, J=7.5 Hz, 3H), 2.44 (t, J=7.3 Hz, 2H), 3.20 (d, J=7.3 Hz, 2H), 3.66 (s, 3H), 7.18 (td, J=2.1, 8.9 Hz, 1H), 7.20 (td, J=2.1, 8.6 Hz, 1H), 7.34 (dt, J=1.2, 7.9 Hz, 1H), 7.54 (d, J=8.2, 8.3 Hz, 2H), 7.77 (d, J=7.6 Hz, 1H), 8.16 (td, J=2.1, 5.5 Hz, 1H), 8.18 (td, J=2.1, 5.5 Hz, 1H) ppm; $^{13}$C NMR (50 MHz, CDCl$_3$): δ 23.7 (t), 33.5 ((t), 51.5 (q), 112.3 (d), 115.5 (d, J=21.0 Hz, 2C), 121.7 (d), 123.6 (d), 128.3 (d), 128.4 (s), 130.7 (s), 132.5 (d, J=9.5 Hz, 2C), 133.9 (s), 148.1 (s), 154.3 (s), 165.1 (s, J=254.6 Hz), 173.8 (s), 183.9 (s) ppm; IR (cm$^{-1}$): 3067, 2950, 1942, 1736, 1645, 1598, 1437, 1303, 1233, 1158, 880, 748, 624.

Example: 15

Ethyl 2-(2-(4-fluorobenzoyl)benzofuran-3-yl)propanoate (3k)

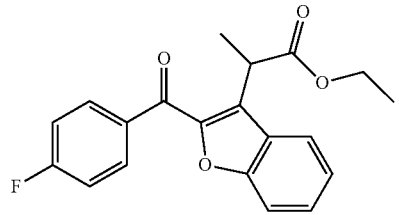 [SMILES: CCOC(=O)C(C)c1c(C(=O)c2ccc(F)cc2)oc2ccccc12]

Isolated by column chromatography (pet ether/AcOEt=9:1, Rf=0.5). The title compound was determined as colourless oil (89%), and the ratio of branch to linear product is (87:13) was determined by $^1$H NMR (200 MHz, CDCl$_3$): δ 1.15 (t, J=7.1 Hz, 3H), 1.67 (d, J=7.2 Hz, 3H), 4.16 (q, J=7.2 Hz, 2H), 4.91 (t, J=7.2 Hz, 1H), 7.19 (td, J=2.2, 8.7 Hz, 1H), 7.24 (td, J=2.2, 8.7 Hz, 1H), 7.32 (ddd, J=1.4, 6.8, 8.1 Hz, 1H), 7.50 (ddd, J=1.3, 8.3, 15.2 Hz, 1H), 7.57 (d, J=8.0 Hz, 1H) 7.77 (d, J=8.0 Hz, 1H), 8.17 (td, J=2.2, 5.4 Hz, 1H), 8.22 (td, J=2.2, 5.4 Hz, 1H) ppm; $^{13}$C NMR (50 MHz, CDCl$_3$): δ 14.1 (q), 16.8 (q), 36.1 (d), 61.0 (t), 112.4 (d), 115.5 (d, J=21.6 Hz, 2C), 122.4 (d), 123.6 (s), 126.7 (d), 128.2 (d, 2C), 129.3 (s), 132.7 (d, J=9.1 Hz, 2C), 133.7 (s), 147.5 (s), 154.3 (s), 165.1 (s, J=255.1 Hz), 173.1 (s), 184.1 (s) ppm; HRMS (ESI) calcd for C$_{20}$H$_{17}$O$_4$FNa (M$^+$+Na): 363.1003; found: 363.1002.

Example: 16

Ethyl 2-(2-(4-fluorobenzoyl)benzofuran-3-yl)propanoate (4i)

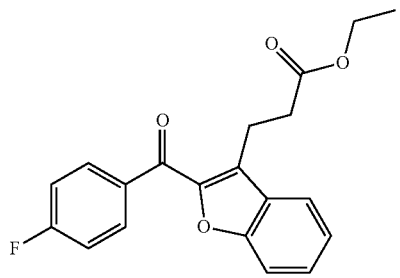 [SMILES: CCOC(=O)CCc1c(C(=O)c2ccc(F)cc2)oc2ccccc12]

Isolated by column chromatography (pet ether/AcOEt=9:1, Rf=0.5). The title compound was determined as colourless oil (87%), and the ratio of branch to linear product is (88:12) was determined by $^1$H NMR (200 MHz, CDCl$_3$): δ 1.19 (t, J=7.3 Hz, 3H), 2.80 (t, J=7.6 Hz, 2H), 3.45 (t, J=7.8 Hz, 2H), 4.10 (q, J=7.2 Hz, 1H), 7.21 (td, J=2.2, 8.6 Hz, 1H), 7.22 (dd, J=2.2, 8.7 Hz, 1H), 7.36 (t, J=7.8 Hz, 1H), 7.51 (ddd, J=1.3, 8.3, 15.2 Hz, 1H), 7.55 (d, J=8.3 Hz, 1H) 7.80 (d, J=8.1 Hz, 1H), 8.21 (dd, J=5.4, 8.3 Hz, 1H), 8.22 (td, J=2.4, 5.4 Hz, 1H) ppm; $^{13}$C NMR (50 MHz, CDCl$_3$): δ 14.1 (q), 20.1 (q), 33.8 (d), 60.5 (t), 112.4 (d), 115.5 (d, J=21.6 Hz, 2C), 121.7 (d), 123.6 (s), 126.2 (d), 128.4 (d), 130.1 (s), 132.6 (d, J=9.3 Hz, 2C), 133.7 (s), 148.2 (s), 154.2 (s), 165.5

(s, J=255.1 Hz), 172.8 (s), 183.7 (s) ppm; IR (cm⁻¹): 3069, 2982, 1909, 1735, 1645, 1598, 1506, 1446, 1347, 1266, 1099, 954, 878, 750, 625.

Example: 17

Methyl 2-(2-(4-fluorobenzoyl)benzofuran-3-yl)propanoate (3j)

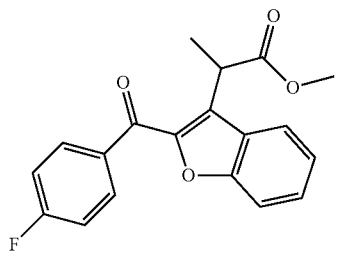 [SMILES: COC(=O)C(C)c1c(C(=O)c2ccc(F)cc2)oc2ccccc12]

Isolated by column chromatography (pet ether/AcOEt=9:1, Rf=0.5). The title compound was determined as colourless oil (87%), and the ratio of branch to linear product is (88:12) was determined by Isolated by thin-layer chromatography (pet ether/AcOEt=9:1, Rf=0.5). The title compound was determined as colourless oil (87%), and the ratio of linear to branch product (88:12) was determined ¹H NMR (200 MHz, CDCl₃) δ ppm 1.67 (d, J=7.2 Hz, 3H), 3.68 (s, 3H), 4.95 (q, J=7.2 Hz, 1H), 7.15-7.26 (m, 2H) 7.29-7.37 (m, 1H) 7.46-7.54 (m, 1H) 7.57 (d, J=8.3 Hz, 1H, 1H) 7.76 (d, J=8.0 Hz, 1H) 8.15-8.25 (m, 2H); ¹³C NMR (50 MHz, CDCl₃): δ 16.8 (q), 35.9 (d), 52.2 (q), 112.4 (d), 115.5 (d, J=21.6 Hz, 2C), 122.3 (d), 123.7 (d), 126.7 (s), 128.2 (d, 2C), 129.2 (s), 132.7 (d, J=9.1 Hz, 2C), 133.5 (s), 133.6 (s, J=2.9 Hz), 147.5 (s), 154.3 (s), 165.1 (s, J=255.1 Hz), 173.6 (s), 184.0 (s) ppm; IR (cm⁻¹): 3459, 2989, 1910, 1739, 1646, 1599, 1304, 1232, 1059, 879, 749; HRMS (ESI) calcd for C₁₉H₁₅O₄FNa (M⁺+Na): 349.0847; found: 349.0843.

Example: 18

Methyl 2-(2-(4-fluorobenzoyl)benzofuran-3-yl)propanoate (4h)

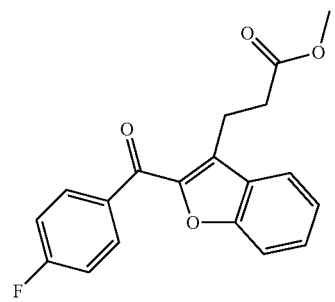 [SMILES: COC(=O)CCc1c(C(=O)c2ccc(F)cc2)oc2ccccc12]

Isolated by column chromatography (pet ether/AcOEt=9:1, Rf=0.5). The title compound was determined as colourless oil (87%), and the ratio of branch to linear product is (88:12) was determined by ¹H NMR (200 MHz, CDCl₃) δ 2.82 (t, J=7.5 Hz, 2H), 3.45 (d, J=7.5 Hz, 2H), 3.64 (q, J=7.2 Hz, 3H), 7.19-7.23 (m, 2H) 7.37 (t, J=7.3 Hz, 1H) 7.49-7.53 (m, 1H) 7.56 (d, J=8.3 Hz, 1H) 7.80 (d, J=8.0 Hz, 1H) 8.19-8.22 (m, 1H) ppm; ¹³C NMR (50 MHz, CDCl₃): δ 20.1 (t), 33.6 (t), 51.7 (q), 112.3 (d), 115.5 (d, J=21.6 Hz, 2C), 121.7 (d), 123.6 (d), 128.1 (s), 128.4 (d, 2C), 130.0 (s, 2C), 132.6 (d, J=9.3 Hz, 2C), 148.2 (s), 154.2 (s), 173.2 (s, 2C), 183.7 (s) ppm; IR (cm⁻¹): 2951, 1736, 1642, 1598, 1559, 1437, 1290, 1233, 1158, 1047, 878, 849, 748.

Example: 19

Methyl 2-(2-(4-fluorobenzoyl)benzofuran-3-yl)butanoate (3o)

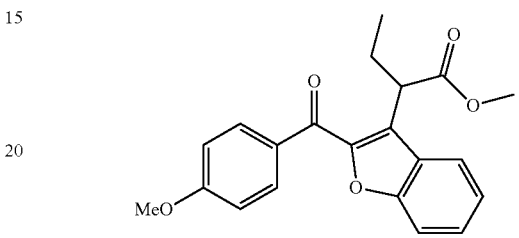

Isolated by column chromatography (pet ether/AcOEt=9:1, Rf=0.5). The title compound was determined as colourless oil (86%), and the ratio of branch to linear product is (91:9) was determined ¹H NMR (200 MHz, CDCl₃): δ 0.94 (t, J=7.5 Hz, 3H), 1.90-2.13 (m, 1H), 2.25-2.46 (m, 1H), 3.67 (s, 3H), 3.91 (s, 3H), 4.82 (dd, J=6.8, 8.6 Hz, 1H), 7.02 (td, J=2.8, 8.6 Hz, 1H), 7.29 (d, J=9.2 Hz, 1H), 7.33 (d, J=7.7 Hz, 2H), 7.47 (dt, J=0.8, 8.3 Hz, 1H), 7.49 (d, J=6.9 Hz, 1H), 7.56 (d, J=8.1 Hz, 1H), 7.84 (d, J=8.0 Hz, 1H), 8.16 (d, J=8.7 Hz, 1H) ppm; ¹³C NMR (50 MHz, CDCl₃): δ 12.1 (q), 24.8 (t), 42.9 (d), 52.0 (q), 55.5 (q), 112.3 (d), 113.7 (d, 2C), 122.9 (d), 123.5 (d), 126.4 (s), 126.9 (s), 127.7 (d), 130.2 (s), 132.5 (d, 2C), 148.8 (s), 154.2 (s), 163.5 (s), 173.4 (s), 184.3 (s) ppm; IR (cm⁻¹): 3017, 2967, 1736, 1639, 1599, 1509, 1460, 1360, 1260, 1113, 1030, 877, 752, 626; HRMS (ESI) calcd for C₂₁H₂₁O₅ (M⁺+H): 353.1384; found: 353.1383.

Example: 20

Methyl 2-(2-(4-fluorobenzoyl)benzofuran-3-yl)butanoate (3n)

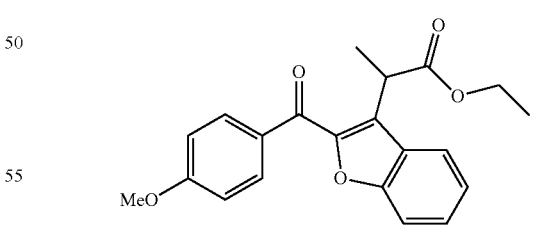

Isolated by column chromatography (pet ether/AcOEt=9:1, Rf=0.5). The title compound was determined as colourless oil (86%), and the ratio of branch to linear product is (92.8) was determined ¹H NMR (200 MHz, CDCl₃): δ 1.15 (t, J=7.2 Hz, 3H), 1.66 (d, J=7.2 Hz, 3H), 3.92 (s, 3H), 4.15 (d, J=7.2 Hz, 2H), 4.89 (d, J=7.2 Hz, 1H), 7.02 (d, J=8.8 Hz, 1H), 7.33 (d, J=1.3, 6.8 Hz, 1H), 7.47 (dt, J=1.1, 8.3 Hz, 1H), 7.57 (d, J=8.2 Hz, 1H), 7.75 (d, J=8.0 Hz, 1H), 8.18 (d, J=9.0 Hz, 1H) ppm; ¹³C NMR (125 MHz, CDCl₃): δ 14.1 (q), 16.9

(q), 36.1 (d), 55.5 (q), 61.0 (t), 112.3 (d), 113.7 (d, 2C), 122.3 (d), 123.5 (d), 126.8 (s), 127.8 (d), 128.3 (s), 130.2 (s), 132.5 (d, 2C), 148.1 (s), 154.2 (s), 163.5 (s), 173.4 (s), 184.2 (s) ppm; IR (cm$^{-1}$): 3070, 2981, 1732, 1638, 1600, 1572, 1456, 1298, 1258, 1167, 1029, 878, 749; HRMS (ESI) calcd for $C_{21}H_{21}O_5$ (M$^+$+H): 353.1384; found: 353.1382.

Example: 21

Methyl 2-(2-(4-methoxybenzoyl)benzofuran-3-yl)propanoate (3m)

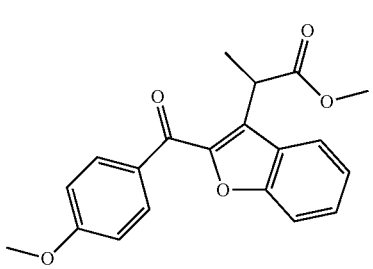

Isolated by column chromatography (pet ether/AcOEt=9:1, Rf=0.5). The title compound was determined as colourless oil (83%), and the ratio of branch to linear product is (91:9) was determined by $^1$H NMR (200 MHz, CDCl$_3$); δ 1.67 (d, J=7.3 Hz, 3H), 3.68 (s, 3H), 3.93 (s, 3H), 4.95 (q, J=7.2 Hz, 1H), 7.03 (d, J=8.7 Hz, 2H), 7.33 (dt, J=0.9, 7.8 Hz, 1H), 7.49 (dt, J=1.4, 8.7 Hz, 1H), 7.58 (d, J=8.3 Hz, 1H), 7.75 (d, J=8.3 Hz, 1H), 8.19 (d, J=8.7 Hz, 2H) ppm; $^{13}$C NMR (50 MHz, CDCl$_3$); δ 16.9 (q), 35.9 (d), 52.2 (q), 55.5 (q), 112.4 (d), 113.7 (d, 2C), 122.2 (d), 123.6 (d), 126.8 (s), 127.8 (d), 128.2 (s), 130.1 (s), 132.5 (d, 2C), 148.1 (s), 154.2 (s), 163.6 (s), 173.9 (s), 184.2 (s) ppm; IR (cm$^{-1}$), 3453, 2953, 1954, 1736, 1643, 1600, 1437, 1364, 1258, 1170, 1027, 989, 878, 754; HRMS (ESI) calcd for $C_{20}H_{19}O_5$ (M$^+$+H): 339.1227; found: 339.1226.

Example: 22

Methyl 2-(5-chloro-2-(4-methoxybenzoyl)benzofuran-3-yl)propanoate (3s)

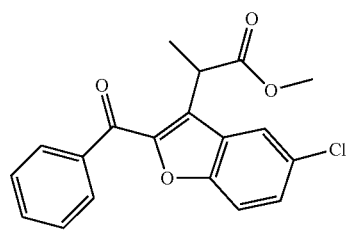

Isolated by column chromatography (pet ether/AcOEt=9:1, Rf=0.5). The title compound was determined as colourless oil (87%), and the ratio of branch to linear product is (91:9) was determined by $^1$H NMR (200 MHz, CDCl$_3$): δ 1.67 (d, J=7.3 Hz, 3H), 3.71 (s, 3H), 4.91 (q, J=7.3 Hz, 1H), 7.03 (d, J=8.7 Hz, 2H), 7.45 (dd, J=2.1, 8.9 Hz, 1H), 7.50 (d, J=8.9 Hz, 1H), 7.54 (d, J=7.3 Hz, 1H), 7.56 (d, J=7.9 Hz, 1H), 7.65 (t, J=7.3 Hz, 1H), 7.75 (d, J=1.8 Hz, 1H) ppm, $^{13}$C NMR (50 MHz, CDCl$_3$): δ 16.9 (q), 35.8 (d), 52.4 (q), 113.6 (d), 121.8 (d), 128.0 (s), 128.1 (s), 128.4 (d, 2C), 128.5 (s), 129.4 (d, 2C), 133.2 (d), 137.1 (s), 148.8 (s), 152.7 (s), 173.4 (s), 185.7 (s) ppm; IR (cm$^{-1}$): 2953, 1956, 1735, 1653, 1437, 1369, 1257, 1199, 1173, 988, 857, 757; HRMS (ESI) calcd for $C_{19}H_{16}O_4Cl$ (M$^+$+H): 343.0732; found: 343.0733.

Example: 23

Methyl 2-(5-chloro-2-(4-methoxybenzoyl)benzofuran-3-yl)propanoate (3t)

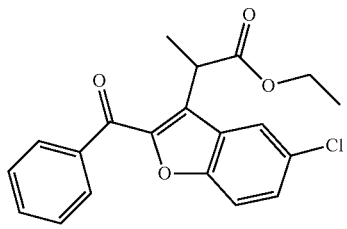 [SMILES: CCOC(=O)C(C)c1c(C(=O)c2ccccc2)oc2ccc(Cl)cc12]

Isolated by column chromatography (pet ether/AcOEt=9:1, Rf=0.5). The title compound was determined as colourless oil (86%), and the ratio of branch to linear product is (93:7) was determined by $^1$H NMR (200 MHz, CDCl$_3$): δ 1.19 (t, J=7.1 Hz, 3H), 1.66 (d, J=7.3 Hz, 3H), 4.19 (q, J=7.1 Hz, 1H), 4.86 (q, J=7.3 Hz, 1H), 7.41-7.51 (m, 2H), 7.53-7.58 (m, 2H), 7.61-7.65 (m, 1H), 7.76 (d, J=1.8, Hz, 1H), 8.09 (dd, J=1.6, 8.5 Hz, 2H) ppm; $^{13}$C NMR (50 MHz, CDCl$_3$): δ 14.1 (q), 16.9 (q), 36.1 (d), 61.2 (t), 113.6 (d), 122.0 (d), 128.0 (s), 128.2 (s), 128.4 (d, 2C), 129.3 (d, 2C), 133.2 (d), 137.1 (s), 148.8 (s), 152.7 (s), 172.9 (s), 185.7 (s) ppm; IR (cm$^{-1}$): 3036, 2928, 1733, 1650, 1598, 1557, 1447, 1295, 1197, 1068, 961, 806, 723, 694; HRMS (ESI) calcd for $C_{20}H_{18}O_4Cl$ (M$^+$+H): 357.0888; found: 357.0887.

Example: 24

Methyl 2-(5-chloro-2-(4-methoxybenzoyl)benzofuran-3-yl)propanoate (3u)

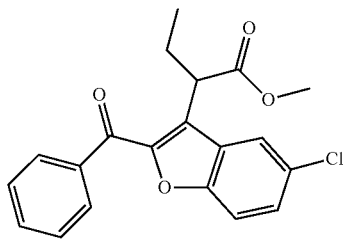 [SMILES: CCC(C(=O)OC)c1c(C(=O)c2ccccc2)oc2ccc(Cl)cc12]

Isolated by column chromatography (pet ether/AcOEt=9:1, Rf=0.5). The title compound was determined as colourless oil (89%), and the ratio of branch to linear product is (91:9) was determined by $^1$H NMR (200 MHz, CDCl$_3$): δ 0.94 (t, J=7.6 Hz, 3H), 2.00 (qt, J=7.3 Hz, 1H), 2.34 (qt, J=7.0 Hz, 1H), 3.70 (s, 3H), 4.78 ( ), 7.44 (dd, J=1.9, 8.5 Hz, 1H), 7.49 (d, J=8.5 Hz, 1H), 7.53 (t, J=7.3 Hz, 3H), 7.64 (tt, J=1.2, 7.3 Hz, 1H), 8.06 (d, J=1.2 Hz, 1H), 8.07 (d, J=7.3 Hz, 1H) ppm; $^{13}$C NMR (50 MHz, CDCl$_3$): δ 12.1 (q), 24.9 (t), 42.9 (d), 52.2 (q), 113.5 (d), 122.5 (d), 126.3 (s), 128.1 (s), 128.4 (d, 2C), 128.5 (s), 129.4 (s), 129.9 (d, 2C), 133.1 (d), 137.2 (s), 149.6 (s), 152.7 (s), 173.0 (s), 185.8 (s) ppm; IR (cm$^{-1}$):

3019, 2970, 2400, 1734, 1648, 1559, 1447, 1292, 1215, 986, 808, 756, 669; HRMS (ESI) calcd for $C_{20}H_8O_4Cl$ (M$^+$+H): 357.0888; found: 357.0888.

Example: 25

Methyl 2-(5-chloro-2-(4-methoxybenzoyl)benzofuran-3-yl)propanoate (3p)

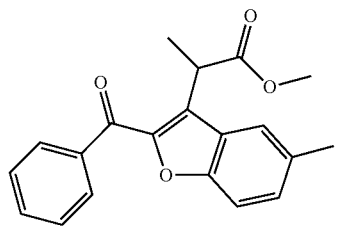 [SMILES: COC(=O)C(C)c1c(C(=O)c2ccccc2)oc2ccc(C)cc12]

Isolated by column chromatography (pet ether/AcOEt=9:1, Rf=0.5). The title compound was determined as colourless oil (82%), and the ratio of branch to linear product is (88:12) was determined by $^1$H NMR (200 MHz, CDCl$_3$): δ 1.67 (d, J=7.3 Hz 3H), 2.48 (s, 3H), 3.69 (s, 3H), 4.95 (q, J=7.3 Hz, 1H), 7.31 (dd, J=1.8, 8.7 Hz, 2H), 7.45 (d, J=8.2 Hz, 1H), 7.53 (d, J=7.3 Hz, 1H), 7.54 (t, J=8.2 Hz, 2H), 7.63 (tt, J=1.4, 7.3 Hz, 1H), 8.11 (d, J=1.4 Hz, 1H), 8.12 (d, J=7.3 Hz, 1H) ppm; $^{13}$C NMR (100 MHz, CDCl$_3$): δ 16.8 (q), 21.5 (q), 35.9 (d), 52.2 (q), 112.0 (d), 121.6 (d), 126.8 (s), 128.3 (d, 2C), 128.6 (s), 129.8 (s), 129.9 (d, 2C), 132.8 (d), 133.4 (s), 137.4 (s), 147.9 (s), 152.9 (s), 173.8 (s), 185.9 (s) ppm; IR (cm$^{-1}$): 2949, 1739, 1645, 1563, 1448, 1300, 1206, 1057, 905, 804, 720; HRMS (ESI) calcd for $C_{20}H_{19}O_4$(M$^+$+H): 323.1278; found: 323.1276.

Example: 26

Methyl 2-(5-chloro-2-(4-methoxybenzoyl)benzofuran-3-yl)propanoate (3q)

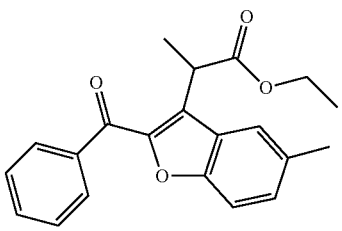 [SMILES: CCOC(=O)C(C)c1c(C(=O)c2ccccc2)oc2ccc(C)cc12]

Isolated by column chromatography (pet ether/AcOEt=9:1, Rf=0.5). The title compound was determined as colourless oil (79%), and the ratio of branch to linear product is (86:14) was determined by $^1$H NMR (500 MHz, CDCl$_3$): δ 1.16 (t, J=7.3 Hz, 3H), 1.66 (d, J=7.0 Hz, 3H), 2.47 (s, 3H), 3.69 (s, 3H), 4.16 (q, J=7.3 Hz, 2H), 4.95 (q, J=7.0 Hz, 1H), 7.30 (dd, J=1.5, 8.5 Hz, 2H), 7.44 (d, J=8.2 Hz, 1H), 7.51-7.54 (m, 3H) 7.62 (tt, J=1.2, 7.3 Hz, 1H), 8.10-8.12 (m, 2H) ppm; $^{13}$C NMR (125 MHz, CDCl$_3$): δ 14.2 (q), 16.9 (q), 21.5 (q), 36.1 (d), 61.1 (t), 112.0 (d), 121.8 (d), 126.9 (s), 128.3 (d, 2C), 128.9 (s), 129.8 (d), 129.9 (d, 2C), 132.8 (d), 133.3 (s), 137.5 (s), 147.9 (s), 152.9 (s), 173.3 (s), 185.9 (s) ppm; IR (cm$^{-1}$): 2981, 1945, 1743, 1648, 1447, 1373, 1259, 1180, 1027, 856, 722, 696; HRMS (ESI) calcd for $C_{21}H_{21}O_4$ (M$^+$+H): 337.1434; found: 337.1430.

Example: 27

Methyl 2-(2-benzoyl-5-methoxybenzofuran-3-yl)butanoate (3r)

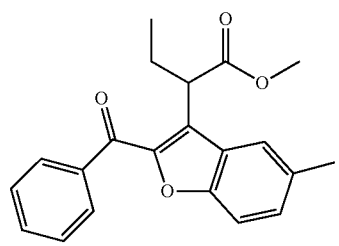 [SMILES: CCC(C(=O)OC)c1c(C(=O)c2ccccc2)oc2ccc(C)cc12]

Isolated by column chromatography (pet ether/AcOEt=9:1, Rf=0.5). The title compound was determined as colourless oil (80%), and the ratio of branch to linear product is (85:15) was determined by $^1$H NMR (400 MHz, CDCl$_3$): δ 0.94 (t, J=7.3 Hz, 3H), 2.04 (qtd, J=1.4, 7.3 Hz, 1H), 2.36 (qt, J=7.3 Hz, 1H), 2.48 (s, 3H), 3.69 (s, 3H), 4.95 (dd, J=6.9, 8.7 Hz, 1H), 7.31 (dd, J=1.8, 8.7 Hz, 2H), 7.44 (d, J=8.7 Hz, 1H), 7.53 (t, J=1.4, 6.9 Hz, 1H), 7.62 (d, J=8.7 Hz, 2H), 7.63 (tt, J=1.4, 7.3 Hz, 1H), 8.09 (d, J=1.4 Hz, 1H), 8.10 (d, J=7.3 Hz, 1H) ppm; $^{13}$C NMR (100 MHz, CDCl$_3$): δ 12.1 (q), 21.5 (q), 24.7 (d), 42.9 (d), 52.1 (q), 111.9 (d), 122.3 (d), 126.8 (s), 126.9 (s), 128.3 (d, 2C), 129.7 (d), 129.9 (d, 2C), 132.8 (d), 133.3 (s), 137.6 (s), 148.7 (s), 152.9 (s), 173.4 (s), 186.0 (s) ppm; IR (cm$^{-1}$): 3350, 2929, 1944, 1736, 1648, 1560, 1436, 1267, 1159, 1042, 907, 803, 694; HRMS (ESI) calcd for $C_{21}H_{21}O_4$ (M$^+$+H): 337.1434; found: 337.1432.

Example: 28

General Procedure for Synthesis of Linear Alkylated Products

[Ru(p-cymene)Cl$_2$]$_2$ (0.01 mmol), PPh$_3$ (0.03 mmol), NaHCO3 (0.5 mmol) were placed in a screw-cap pressure tube, which was then evacuated and back filled with argon. To the reaction vessel was then added 2-aroylbenzofuran (0.1 mmol), alkene (0.3 mmol), and dioxane (2 mL). The solution was then stirred at 140° C. (bath temperature) for 36 h. The reaction mixture was then cooled to room temperature, solvent were evaporated and the crude products were purified by column chromatography 100-200 mesh (pet ether/AcOEt) to give analytically pure linear alkylated products.

Example: 29

Methyl 3-(2-benzoylbenzofuran-3-yl)propanoate (4a)

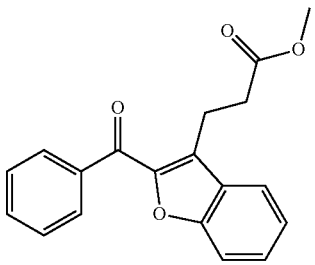 [SMILES: COC(=O)CCc1c(C(=O)c2ccccc2)oc2ccccc12]

Isolated by column chromatography (pet ether/AcOEt=9:1, Rf=0.4). The title compound was determined as colourless oil, and the ratio of linear to branch product is (86:14); $^1$H NMR (400 MHz, CDCl$_3$): δ 2.81 (t, J=7.8 Hz, 2H) 3.44 (t, J=7.8 Hz, 2H) 3.63 (s, 3H) 7.35 (ddd, J=1.4, 6.8, 8.2 Hz 1H) 7.47-7.55 (m, 4H) 7.59-7.64 (m, 1H) 7.78 (d, J=7.78 Hz, 1H) 8.10-8.13 (m, 2H) $^{13}$C NMR (100 MHz, CDCl$_3$): δ 20.4 (t), 33.9 (t), 51.7 (q), 112.3 (d), 121.6 (d), 123.5 (d), 128.1 (s), 128.3 (d, 3C), 129.6 (s), 129.8 (d, 2C), 132.7 (d), 137.5 (s), 148.4 (s), 154.3 (s), 173.3 (s), 185.5 (s). ppm; HRMS (ESI) calcd for C$_{19}$H$_{16}$O$_4$ (M$^+$+Na): 331.0946; found: 331.0941.

Example: 30

Ethyl 3-(2-benzoylbenzofuran-3-yl)propanoate (4b)

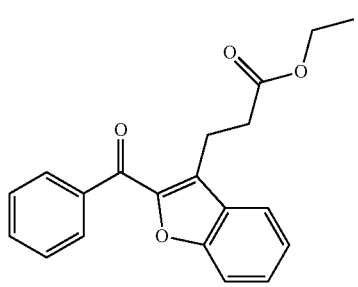 [SMILES: CCOC(=O)CCc1c(C(=O)c2ccccc2)oc2ccccc12]

Isolated by column chromatography (pet ether/AcOEt=9:1, Rf=0.4). The title compound was determined as colourless oil and the ratio of linear to branch product is (88:12), $^1$H NMR (400 MHz, CDCl$_3$): δ 1.20 (t, J=7.1 Hz, 3H) 2.81 (t, J=7.6 Hz, 2H) 3.46 (t, J=7.6 Hz, 2H) 4.10 (q, J=7.1 Hz, 2H) 7.34-7.387 (m, 1H) 7.49-7.56 (m, 4H) 7.61-7.65 (m, 1H) 7.81 (d, J=7.8 Hz, 1H) 8.13 (d, 2H). ppm. $^{13}$C NMR (100 MHz, CDCl$_3$): δ 14.1 (q), 20.1 (t), 33.8 (t), 60.5 (t), 112.3 (d), 121.7 (d), 123.5 (d), 128.2 (s), 128.3 (d, 3C), 129.7 (s), 129.8 (d, 2C), 132.7 (d), 137.5 (s), 148.4 (s), 154.3 (s), 172.8 (s), 185.5 (s) ppm; HRMS (ESI) calcd for C$_{20}$H$_{18}$O$_4$ (M$^+$+Na): 345.1103; found: 345.1097.

Example: 31

Butyl 3-(2-benzoylbenzofuran-3-yl)propanoate (4c)

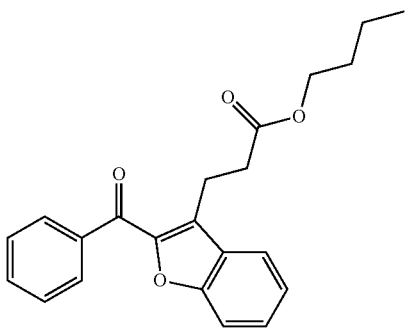 [SMILES: CCCCOC(=O)CCc1c(C(=O)c2ccccc2)oc2ccccc12]

Isolated by column chromatography (pet ether/AcOEt=9:1, Rf=0.4). The title compound was determined as colourless oil and the ratio of linear to branch product is (86:14), $^1$H NMR (400 MHz, CDCl$_3$): δ 0.89 (t, J=7.3 Hz, 3H) 1.26-1.33 (m, 2H) 1.5-1.57 (m, 2H) 2.82 (t, J=7.6 Hz, 2H) 3.46 (t, J=7.6 Hz, 2H) 4.04 (t, J=6.7 Hz, 2H) 7.34-7.38 (m, 1H) 7.49-7.57 (m, 4H), 7.61-7.65 (m, 1H), 7.80 (d, J=7.7 Hz, 1H), 8.13 (d, J=7.7 Hz, 2H) $^{13}$C NMR (100 MHz, CDCl$_3$): δ 13.6 (q), 19.0 (t), 20.1 (t), 30.5 (t), 33.8 (t), 64.5 (t), 112.3 (d), 121.7 (d), 123.5 (d), 128.2 (s), 128.3 (d, 3C), 129.7 (s), 129.8 (d, 2C), 132.7 (d), 137.5 (s), 148.4 (s), 154.3 (s), 172.8 (s), 185.5 (s) ppm; HRMS (ESI) calcd for C$_{22}$H$_{22}$O$_4$ (M$^+$+Na): 373.1416; found: 373.1410.

Example: 32

Methyl 3-(2-(4-methoxybenzoyl)benzofuran-3-yl)propanoate (4j)

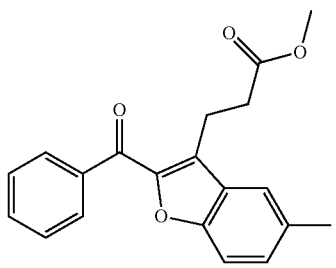 [SMILES: COC(=O)CCc1c(C(=O)c2ccccc2)oc2ccc(C)cc12]

Isolated by column chromatography (pet ether/AcOEt=9:1, Rf=0.4). The title compound was determined as colourless oil, and the ratio of linear to branch product is (75:25), $^1$H NMR (400 MHz, CDCl$_3$): δ 2.50 (s, 3H), 2.81 (t, J=7.9 Hz, 2H) 3.43 (t, J=7.9 Hz, 2H) 3.67 (s, 3H) 7.32 (d, J=8.5 Hz, 1H) 7.44 (d, J=8.5 Hz, 1H) 7.52-7.55 (m, 3H) 7.60-7.64 (m, 1H) 8.12 (d, J=7.8 Hz, 2H) $^{13}$C NMR (100 MHz, CDCl$_3$), δ 20.1 (t), 21.4 (q), 33.6 (t), 51.7 (q), 111.9 (d), 121.0 (d), 128.2 (s), 128.3 (d, 2C), 129.4 (s), 129.8 (d, 2C), 129.9 (d), 132.7 (d), 133.2 (s), 137.6 (s), 148.6 (s), 152.8 (s), 173.3 (s), 185.5 (s). ppm; HRMS (ESI) calcd for C$_{20}$H$_{18}$O$_4$ (M$^+$+Na): 345.1103; found: 345.1097.

Example: 33

Ethyl 3-(2-(4-methoxybenzoyl)benzofuran-3-yl)propanoate (4k)

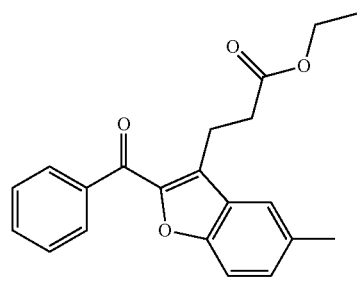

Isolated by column chromatography (pet ether/AcOEt=9:1, Rf=0.4). The title compound was determined as colourless oil, and the ratio of linear to branch product is (92:8), $^1$H NMR (400 MHz, CDCl$_3$): δ 1.22 (t, J=7.1 Hz, 3H) 2.80 (t, J=7.5 Hz, 2H) 3.40 (t, J=7.5 Hz, 2H) 4.12 (q, J=7.1 Hz, 2H) 7.32 (d, J=8.5 Hz, 1H) 7.43 (d, J=8.5 Hz, 1H) 7.52-7.55 (m, 3H) 7.59-7.63 (m, 1H) 8.12 (d, J=7.6 Hz, 2H) $^{13}$C NMR (125 MHz, CDCl$_3$): δ 14.2 (q), 20.1 (t), 21.4 (q), 33.9 (t), 60.5 (t), 111.9 (d), 121.1 (d), 128.3 (d, 2C), 128.3 (s), 129.5 (s), 129.8 (d, 2C), 129.9 (d), 132.6 (d), 133.2 (s), 137.7 (s), 148.6 (s), 152.9 (s), 172.9 (s), 185.5 (s). ppm; HRMS (ESI) calcd for C$_{21}$H$_{20}$O$_4$ (M$^+$+Na): 359.1259; found: 359.1254.

Example: 34

Methyl 3-(2-benzoyl-5-chlorobenzofuran-3-yl)propanoate (4f)

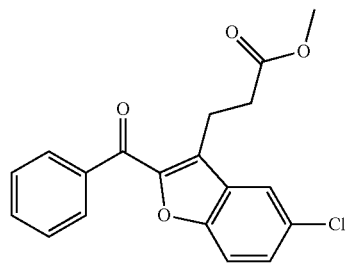 [SMILES: COC(=O)CCc1c(C(=O)c2ccccc2)oc2ccc(Cl)cc12]

Isolated by column chromatography (pet ether/AcOEt=9:1, Rf=0.4). The title compound was determined as colourless oil (86%), and the ratio of branch to linear product is (89:11) was determined by $^1$H NMR (400 MHz, CDCl$_3$): δ 2.79 (t, J=7.6 Hz, 2H) 3.38 (t, J=7.6 Hz, 2H) 3.64 (s, 3H) 7.42-7.54 (m, 4H) 7.59-7.65 (tt, J=1.4, 3.7 Hz, 1H) 7.75 (d, J=2.3 Hz, 1H) 8.07-8.10 (m, 2H) $^{13}$C NMR (100 MHz, CDCl$_3$): δ 20.1 (t), 33.6 (t), 51.9 (q), 113.6 (d), 121.3 (d), 128.5 (d, 2C), 128.7 (d), 128.9 (s), 129.4 (s), 129.6 (s), 129.9 (d, 2C), 133.1 (d), 137.3 (s), 149.6 (s), 152.6 (s), 173.1 (s), 185.4 (s). Ppm; HRMS (ESI) calcd for C$_{19}$H$_{15}$ClO$_4$ (M$^+$+Na): 365.0557; found: 365.0551.

Example: 35

Ethyl 3-(2-benzoyl-5-chlorobenzofuran-3-yl)propanoate (4g)

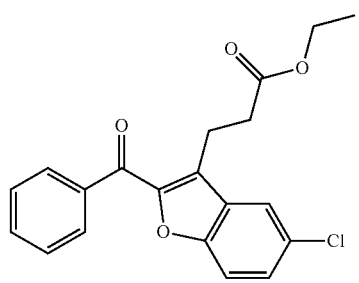

Isolated by column chromatography (pet ether/AcOEt=9:1, Rf=0.4). The title compound was determined as colourless oil (86%), and the ratio of branch to linear product is (84:16) was determined by $^1$H NMR (400 MHz, CDCl$_3$): δ 1.22 (t, J=7.2 Hz, 3H) 2.80 (t, J=7.5 Hz, 2H) 3.40 (t, J=7.5 Hz, 2H) 4.12 (q, J=7.1 Hz, 2H) 7.44-7.56 (m, 4H) 7.62-7.66 (m, 1H) 7.77 (d, J=1.7 Hz, 1H) 8.09-8.11 (m, 2H) ppm; $^{13}$C NMR (100 MHz, CDCl$_3$): δ 14.1 (q), 20.0 (t), 33.8 (t), 60.6 (t), 113.4 (d), 121.2 (d), 128.4 (d, 2C), 128.6 (d), 128.9 (s), 129.3 (s), 129.6 (s), 129.8 (d, 2C), 133.0 (d), 137.2 (s), 149.5 (s), 152.5 (s), 172.6 (s), 185.3 (s). ppm; HRMS (ESI) calcd for C$_{20}$H$_{17}$ClO$_4$ (M$^+$+Na): 379.0713; found: 379.0709.

Example: 36

Methyl 3-(2-(4-methoxybenzoyl)benzofuran-3-yl)propanoate (4d)

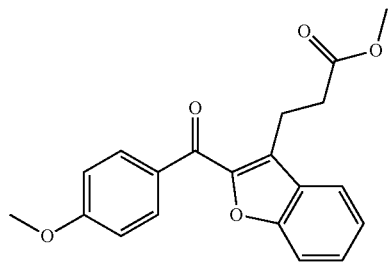

Isolated by column chromatography (pet ether/AcOEt=9:1, Rf=0.4). The title compound was determined as colourless oil (74%), and the ratio of branch to linear product is (80:20) was determined by $^1$H NMR (400 MHz, CDCl$_3$): δ 2.82 (t, J=7.7 Hz, 2H) 3.45 (t, J=7.7 Hz, 2H) 3.65 (s, 3H) 3.92 (s, 3H) 7.03 (d, J=8.8 Hz, 2H) 7.34-7.38 (m, 1H) 7.48-7.52 (m, 1H) 7.55-7.57 (m, 1H) 7.78 (d, J=7.8 Hz, 1H) 8.20 (d, J=9.0 Hz, 2H)) ppm; $^{13}$C NMR (100 MHz, CDCl$_3$): δ 20.1 (t), 33.7 (t), 51.6 (q), 55.5 (q), 112.2 (d), 113.7 (d, 2C), 121.5 (d), 123.4 (d), 128.0 (d), 128.9 (s), 130.2 (s), 132.3 (d, 2C), 148.8 (s), 154.1 (s), 163.4 (s), 173.3 (s), 183.8 (s) ppm; HRMS (ESI) calcd for C$_{20}$H$_{18}$O$_5$ (M$^+$+Na): 361.1052; found: 361.1046.

Example: 37

Ethyl 3-(2-(4-methoxybenzoyl)benzofuran-3-yl)propanoate (4c)

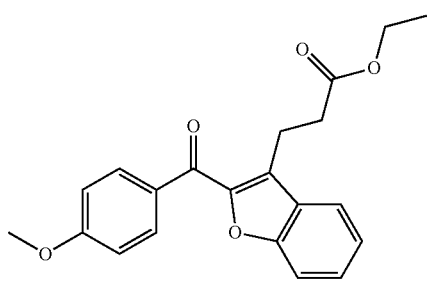 [SMILES: CCOC(=O)CCc1c(C(=O)c2ccc(OC)cc2)oc2ccccc12]

Isolated by column chromatography (pet ether/AcOEt=9:1, Rf=0.4). The title compound was determined as colourless oil (76%), and the ratio of branch to linear product is (82:18) was determined by $^1$H NMR (400 MHz, CDCl$_3$): δ 1.20 (t, J=7.2 Hz, 3H) 2.81 (t, J=7.6 Hz, 2H) 3.44 (t, J=7.6 Hz, 2H) 3.92 (s, 3H) 4.10 (q, J=7.2 Hz, 2H) 7.01-7.05 (m, 2H) 7.33-7.37 (m, 1H) 7.46-7.52 (m, 1H) 7.54-7.58 (m, 1H) 7.79 (dd, J=7.8, 1.1 Hz, 1H) 8.18-8.22 (m, 2H) ppm; $^{13}$C NMR (100 MHz, CDCl$_3$): δ $^{13}$C NMR (100 MHz, CDCl$_3$): δ 14.1 (q), 20.1 (t), 33.9 (t), 55.5 (q), 60.5 (t), 112.2 (d), 113.7 (d, 2C), 121.6 (d), 123.4 (d), 128.0 (d), 128.3 (s), 129.0 (s), 130.3 (s), 132.3 (d, 2C), 148.8 (s), 154.1 (s), 163.4 (s), 172.9 (s), 183.8 (s) ppm; HRMS (ESI) calcd for C$_{21}$H$_{20}$O$_5$ (M$^+$+Na): 375.1208; found: 375.1201.

Example: 38

General Procedure A

Hydroarylation of Acrylates Employing Ru(PPh$_3$)$_3$Cl$_2$ Complex 2-aroylbenzo[b]furan (0.1 mmol) was placed in a screw cap pressure tube and dissolved in anhydrous toluene, which was then evacuated and back filled with argon. To the reaction vessel alkene (acrylate) (0.3 mmol), K$_2$CO$_3$ (0.3 mmol), Ru(PPh$_3$)$_3$Cl$_2$ (0.005 mmol) and AgOAc (0.03 mmol) were added. The solution was then stirred at 140° C. (bath temperature) for 12 h. The reaction mixture was cooled to room temperature. The solvent were evaporated and the crude products were purified by column chromatography (pet ether/AcOEt) to give analytically pure.

Example: 39

Methyl 2-(2-benzoylbenzofuran-3-yl)propanoate (3aa)

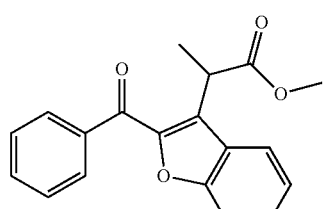

Isolated by column chromatography (pet.ether/AcOEt=9:1, R$_f$=0.5). The title compound was determined as colourless oil (87%), and the ratio of branch to linear product is (94:6). $^1$H NMR (200 MHz, CDCl$_3$): δ 1.67 (d, J=7.2 Hz, 3H), 3.68 (s, 3H), 4.96 (q, J=7.2 Hz, 1H), 7.32 (ddd, J=1.4, 6.8, 8.1 Hz, 1H), 7.45-7.68 (m, 5H), 7.75 (d, J=8.0 Hz, 1H), 8.10-8.16 (m, 2H); $^{13}$C NMR (50 MHz, CDCl$_3$): δ 16.8 (q), 35.9 (d), 52.2 (q), 112.5 (d), 122.2 (d), 123.7 (d), 126.7 (s), 128.1 (d), 128.3 (d, 2C), 128.8 (s), 129.9 (d, 2C), 132.9 (d), 137.3 (s), 147.7 (s), 154.3 (s), 173.7 (s), 185.9 (s) ppm; IR (neat): ν 3020, 2400, 1735, 1645, 1563, 1261, 1215, 1059, 877, 757, 669 cm$^{-1}$; HRMS (ESI) calcd for C$_{19}$H$_{16}$O$_4$Na (M$^+$+Na): 331.0941; found: 331.0938.

Example: 40

Ethyl 2-(2-benzoylbenzofuran-3-yl)propanoate (3ab)

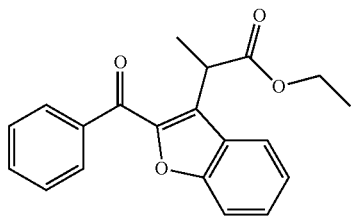 [SMILES: CCOC(=O)C(C)c1c(C(=O)c2ccccc2)oc2ccccc12]

Isolated by column chromatography (pet.ether/AcOEt=9.1, R$_f$=0.5). The title compound was determined as colourless oil (88%) and the ratio of branch to linear product is (92:8). $^1$H NMR (200 MHz, CDCl$_3$): δ 1.15 (t, J=7.2 Hz, 3H), 1.67 (d, J=7.3 Hz, 3H), 4.16 (q, J=7.2 Hz, 2H), 4.91 (q, J=7.3 Hz, 1H), 7.32 (ddd, J=1.4, 6.8, 8.1 Hz, 1H), 7.44-7.67 (m, 5H), 7.77 (d, J=8.0 Hz, 1H), 8.09-8.14 (m, 2H); $^{13}$C NMR (50 MHz, CDCl$_3$): δ 14.1 (q), 16.9 (q), 36.1 (d), 61.0 (t), 112.4 (d), 122.3 (d), 123.5 (d), 126.7 (s), 128.0 (d), 128.3 (d, 2C), 129.0 (s), 129.9 (d, 2C), 132.9 (d), 137.4 (s), 147.7 (s), 154.3 (s), 173.2 (s), 185.8 (s) ppm; IR (neat): ν 3278, 3061, 2984, 1908, 1732, 1645, 1599, 1448, 1300, 1200, 1093, 876, 752, 680 cm$^{-1}$; HRMS (ESI) calcd for C$_{20}$H$_{18}$O$_4$Na (M$^+$+Na): 345.1097; found: 345.1095.

Example: 41

Butyl 2-(2-benzoylbenzofuran-3-yl)propanoate (3ac)

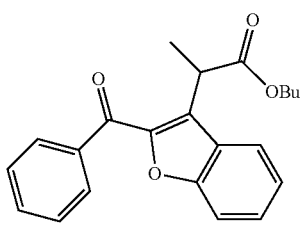

Isolated by column chromatography (pet.ether/AcOEt=9.1, R$_f$=0.5). The title compound was determined as colourless oil (86%), and the ratio of branch to linear product is (92:8). $^1$H NMR (400 MHz, CDCl$_3$): δ 0.77 (t, J=7.3 Hz, 3H), 1.10-1.30 (m, 2H), 1.43-1.54 (m, 2H), 1.66 (d, J=6.9 Hz, 3H), 4.09 (t, J=6.6 Hz, 2H), 4.90 (q, J=7.3 Hz, 1H), 7.31 (td, J=0.9, 7.6 Hz, 1H), 7.46-7.56 (m, 4H), 7.60-7.64 (m, 1H), 7.77 (d, J=7.8 Hz, 1H), 8.07-8.12 (m, 2H); $^{13}$C NMR (100 MHz, CDCl$_3$): δ 13.5 (q), 16.8 (q), 18.9 (t), 30.5 (t), 36.1 (d), 64.9 (t), 112.4 (d), 122.4 (d), 123.6 (d), 126.8 (s), 128.1 (d), 128.3 (d, 2C), 129.0 (s), 129.9 (d, 2C), 132.9 (d), 137.4 (s), 147.7 (s), 154.4 (s), 173.3 (s), 185.9 (s) ppm; IR (neat): ν 3393, 2959, 1735, 1647, 1448, 1300, 1260, 876, 751, 724 cm$^{-1}$; HRMS (ESI) calcd for C$_{22}$H$_{23}$O$_4$ (M$^+$+H): 351.1591; found: 351.1589.

Example: 42

Cyclohexyl 2-(2-benzoylbenzofuran-3-yl)propanoate (3ad)

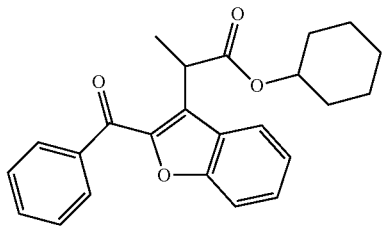 [SMILES: CC(C(=O)OC1CCCCC1)c1c(C(=O)c2ccccc2)oc2ccccc12]

Isolated by column chromatography (pet.ether/AcOEt=9:1, R$_f$=0.5). The title compound was determined as colourless oil (87%), and the ratio of branch to linear product (91:9). $^1$H NMR (500 MHz, CDCl$_3$): δ 1.13-1.47 (m, 8H), 1.63-1.65 (m, 1H), 1.66 (d, J=7.3 Hz, 3H), 1.79-1.82 (m, 1H), 4.80-4.85 (m, 1H), 4.86 (q, 7.3 Hz, 1H), 7.30 (dt, J=0.6, 7.9 Hz, 1H), 7.47 (ddd, J=1.2, 7.3, 8.4 Hz, 1H), 7.51-7.55 (m, 3H), 7.62 (tt, J=1.2, 7.9 Hz, 1H), 7.76 (d, J=7.9 Hz, 1H), 8.08-8.11 (m, 2H); $^{13}$C NMR (125 MHz, CDCl$_3$): δ 16.9 (q), 23.4 (t), 23.6 (t), 25.3 (t), 31.2 (t), 31.4 (t), 36.4 (d), 73.2 (d), 112.4 (d), 122.6 (d), 123.5 (d), 126.8 (s), 128.0 (d), 128.3 (d, 2C), 129.2 (s), 129.9 (d, 2C), 132.9 (d), 137.5 (s), 147.7 (s), 154.4 (s), 172.6 (s), 185.9 (s) ppm; IR (neat): ν 2936, 2858, 1729, 1648, 1560, 1448, 1298, 1201, 1017, 876, 750, 723 cm$^{-1}$; HRMS (ESI) calcd for C$_{24}$H$_{25}$O$_4$ (M$^+$+H): 377.1747; found: 377.1746.

Example: 43

Methyl 2-(2-benzoylbenzofuran-3-yl)butanoate (3ae)

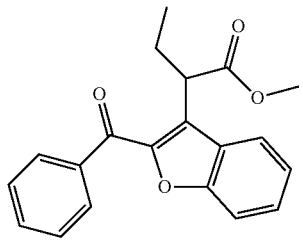 [SMILES: CCC(C(=O)OC)c1c(C(=O)c2ccccc2)oc2ccccc12]

Isolated by column chromatography (pet.ether/AcOEt=9:1, R$_f$=0.5). The title compound was determined as colourless oil (84%), and the ratio of branch to linear product (91:9). $^1$H NMR (200 MHz, CDCl$_3$): δ 0.94 (t, J=7.5 Hz, 3H), 1.91-2.13 (m, 1H), 2.26-2.47 (m, 1H), 3.67 (s, 3H), 4.84 (dd, J=6.7, 8.6 Hz, 1H), 7.32 (dt, J=1.3, 8.6 Hz, 1H), 7.44-7.67 (m, 5H), 7.84 (d, J=7.6 Hz, 1H), 8.07-8.13 (m, 2H); $^{13}$C NMR (50 MHz, CDCl$_3$): δ 12.0 (q), 24.8 (t), 42.9 (d), 52.1 (q), 112.4 (d), 122.9 (d), 123.6 (d), 126.9 (s), 127.0 (s), 128.0 (d), 128.3 (d, 2C), 129.9 (d, 2C), 132.9 (d), 137.4 (s), 148.5 (s), 154.3 (s), 173.3 (s), 185.9 (s) ppm; IR (neat): ν 3279, 3060, 2968, 1944, 1734, 1647, 1598, 1447, 1361, 1264, 1112, 1002, 979, 875, 752, 680 cm$^{-1}$; HRMS (ESI) calcd for C$_{20}$H$_{18}$O$_4$Na (M$^+$+Na): 345.1097; found: 345.1095.

Example: 44

Methyl 4-(2-benzoylbenzofuran-3-yl)butanoate (5)

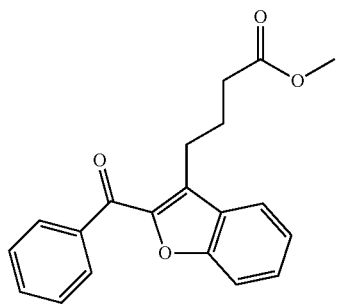 [SMILES: COC(=O)CCCc1c(C(=O)c2ccccc2)oc2ccccc12]

Isolated by column chromatography (pet.ether/AcOEt=9:1, R$_f$=0.5). $^1$H NMR (400 MHz, CDCl$_3$): δ 2.12 (quin, J=7.5 Hz, 2H), 2.46 (t, J=7.5 Hz, 2H), 3.22 (t, J=7.6 Hz, 2H), 3.68 (s, 3H), 7.36 (t, J=7.3 Hz, 1H), 7.47-7.58 (m, 4H), 7.63 (t, J=7.3 Hz, 1H), 7.78 (d, J=7.8 Hz, 1H), 8.11 (d, J=7.1 Hz, 2H); $^{13}$C NMR (101 MHz, CDCl$_3$) δ 23.7 (t), 24.7 (t), 33.5 (t), 51.5 (q), 112.3 (d), 121.6 (d), 123.5 (d), 128.2 (d), 128.3 (d, 2C), 128.5 (s), 129.8 (d, 2C), 130.3 (s), 132.7 (d), 137.7 (s), 148.3 (s), 154.3 (s), 173.8 (s), 185.7 (s) ppm: IR (neat): ν 3067, 2950, 1942, 1736, 1645, 1598, 1437, 1303, 1233, 1158, 880, 748, 624 cm$^{-1}$; HRMS (ESI) calcd for C$_{20}$H$_{19}$O$_4$ (M$^+$+H): 323.1278; found: 323.1280.

Example: 45

Ethyl 2-(2-benzoylbenzofuran-3-yl)-3-phenylpropanoate (3af)

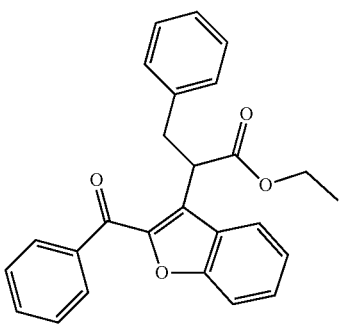 [SMILES: CCOC(=O)C(Cc1ccccc1)c1c(C(=O)c2ccccc2)oc2ccccc12]

Isolated by column chromatography (pet.ether/AcOEt=9:1, R$_f$=0.5). The title compound was determined as colourless oil (54%), and the ratio of branch to linear product (94:6), $^1$H NMR (400 MHz, CDCl$_3$): δ 1.13 (t, J=7.3 Hz, 3H), 3.22 (dd, J=8.2, 13.3 Hz, 1H), 3.63 (dd, J=7.3, 13.3 Hz, 1H), 4.15 (dq, J=2.8, 7.0 Hz, 2H), 5.15 (dd, J=6.9, 8.2 Hz, 1H), 7.04-7.13

(m, 5H), 7.29-7.33 (m, 1H), 7.45-7.50 (m, 3H), 7.52 (d, J=8.2 Hz, 1H), 7.57-7.61 (m, 1H), 7.85 (d, J=8.2 Hz, 1H), 7.87-7.90 (m, 2H); $^{13}$C NMR (100 MHz, CDCl$_3$): δ 14.1 (q), 37.7 (t), 43.5 (d), 61.2 (t), 112.4 (d), 122.8 (d), 123.6 (d), 126.3 (d), 126.8 (s), 127.9 (d), 128.1 (d, 2C), 128.2 (d, 2C), 129.0 (d, 2C), 129.7 (d, 2C), 132.8 (d), 137.4 (s), 138.5 (s, 2C), 148.5 (s), 154.2 (s), 172.2 (s), 185.9 (s) ppm; IR (neat): ν 3448, 3062, 3028, 2927, 1946, 1732, 1648, 1561, 1447, 1366, 1291, 1175, 1002, 929, 876, 752 cm$^{-1}$; HRMS (ESI) calcd for C$_{26}$H$_{22}$O$_4$Na (M$^+$+Na): 421.1410; found: 421.1407.

Example: 46

Methyl 3-(2-benzoylbenzofuran-3-yl)-2-methylpropanoate (4ag)

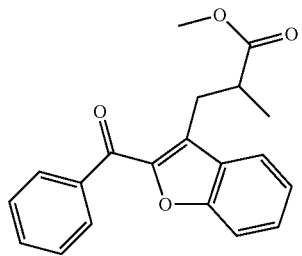 [SMILES: COC(=O)C(C)Cc1c(C(=O)c2ccccc2)oc2ccccc12]

Isolated by column chromatography (pet.ether/AcOEt=9:1, R$_f$=0.4). The title compound was determined as colourless oil (88%). $^1$H NMR (400 MHz, CDCl$_3$): δ 1.27 (d, J=6.9 Hz, 3H), 3.02-3.07 (m, 1H), 3.30 (dd, J=7.3, 13.3 Hz, 1H), 3.44 (dd, J=7.3, 13.3 Hz, 1H), 3.54 (s, 3H), 7.33 (dt, J=1.4, 8.2 Hz, 1H), 7.46-7.51 (m, 2H), 7.53 (d, J=7.8 Hz, 2H), 7.59-7.63 (m, 1H), 7.77 (d, J=7.79 Hz, 1H), 8.11-8.14 (m, 2H); $^{13}$C NMR (100 MHz, CDCl$_3$): δ 17.4 (q), 28.4 (t), 39.9 (d), 51.7 (q), 112.3 (d), 121.9 (d), 123.5 (d), 128.2 (d), 128.3 (d, 2C), 128.6 (s), 128.8 (s), 129.8 (d, 2C), 132.7 (d), 137.5 (s), 148.7 (s), 154.2 (s), 176.5 (s), 185.6 (s) ppm; IR (neat): ν 3061, 2950, 1735, 1644, 1598, 1558, 1447, 1373, 1291, 1267, 1171, 974, 875, 750, 722, 693 cm$^{-1}$; HRMS (ESI) calcd for C$_{20}$H$_{18}$O$_4$Na (M$^+$+Na): 345.1097; found: 345.1094.

Example: 47

Butyl 3-(2-benzoylbenzofuran-3-yl)-2-methylpropanoate (4ah)

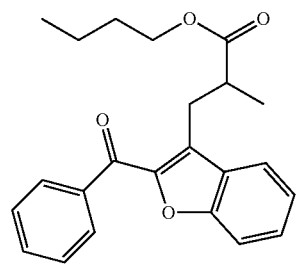 [SMILES: CCCCOC(=O)C(C)Cc1c(C(=O)c2ccccc2)oc2ccccc12]

Isolated by column chromatography (pet.ether/AcOEt=9:1, R$_f$=0.4). The title compound was determined as colourless oil (86%). $^1$H NMR (400 MHz, CDCl$_3$): δ 0.81 (t, J=7.3 Hz, 3H), 1.12-1.22 (m, 2H), 1.27 (d, J=6.9 Hz, 3H), 1.36-1.43 (m, 2H), 3.03 (hexatet, J=7.3 Hz, 1H), 3.31 (dd, J=6.9, 13.3 Hz, 1H), 3.41 (dd, J=8.2, 13.3 Hz, 1H), 3.86-3.97 (m, 2H), 7.31-7.35 (m, 1H), 7.45-7.54 (m, 4H), 7.61 (tt, J=1.4, 7.3 Hz, 1H), 7.75 (d, J=7.8 Hz, 1H), 8.09-8.12 (m, 2H); $^{13}$C NMR (100 MHz, CDCl$_3$): δ 13.6 (q), 17.5 (q), 18.9 (t), 28.5 (t), 30.4 (t), 40.0 (d), 64.3 (t), 112.2 (d), 122.0 (d), 123.5 (d), 128.2 (d), 128.3 (d, 2C), 128.6 (s), 129.0 (s), 129.8 (d, 2C), 132.7 (d), 137.6 (s), 148.6 (s), 154.2 (s), 176.2 (s), 185.5 (s) ppm, IR (neat): ν 3061, 2960, 1908, 1731, 1644, 1557, 1448, 1373, 1291, 1173, 976, 875, 750, 693 cm$^{-1}$; HRMS (ESI) calcd for C$_{23}$H$_{24}$O$_4$Na (M$^+$+Na): 387.1567; found: 387.1563.

Example: 48

Methyl 2-(2-(4-fluorobenzoyl)benzofuran-3-yl)propanoate (3ba)

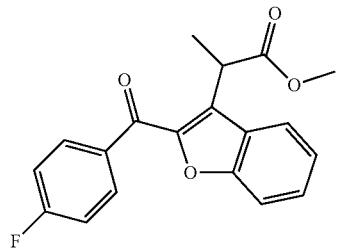 [SMILES: COC(=O)C(C)c1c(C(=O)c2ccc(F)cc2)oc2ccccc12]

Isolated by column chromatography (pet.ether/AcOEt=9:1, R$_f$=0.5). The title compound was determined as colourless oil (87%), and the ratio of branch to linear product (88:12). $^1$H NMR (200 MHz, CDCl$_3$): δ 1.67 (d, J=7.2 Hz, 3H), 3.68 (s, 3H), 4.95 (q, J=7.2 Hz, 1H), 7.15-7.26 (m, 2H), 7.29-7.37 (m, 1H), 7.46-7.54 (m, 1H), 7.57 (d, J=8.3 Hz, 1H), 7.76 (d, J=8.0 Hz, 1H), 8.15-8.25 (m, 2H); $^{13}$C NMR (50 MHz, CDCl$_3$): δ 16.8 (q), 35.9 (d), 52.2 (q), 112.4 (d), 115.5 (d, J=21.6 Hz, 2C), 122.3 (d), 123.7 (d), 126.7 (s), 128.2 (d), 129.2 (s), 132.7 (d, J=9.1 Hz, 2C), 133.5 (s, 2.9 Hz), 147.5 (s), 154.3 (s), 165.1 (s, J=255.1 Hz), 173.6 (s), 184.0 (s) ppm; IR (neat): ν 3459, 2989, 1910, 1739, 1646, 1599, 1304, 1232, 1059, 879, 749 cm$^{-1}$; HRMS (ESI) calcd for C$_{19}$H$_{15}$O$_4$FNa (M$^+$+Na): 349.0847; found: 349.0843.

Example: 49

Ethyl 2-(2-(4-fluorobenzoyl)benzofuran-3-yl)propanoate (3bb)

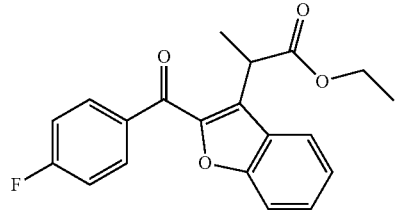 [SMILES: CCOC(=O)C(C)c1c(C(=O)c2ccc(F)cc2)oc2ccccc12]

Isolated by column chromatography (pet.ether/AcOEt=9:1, $R_f$=0.5). The title compound was determined as colourless oil (89%), and the ratio of branch to linear product (87:13). $^1$H NMR (200 MHz, CDCl$_3$): δ 1.15 (t, J=7.1 Hz, 3H), 1.67 (d, J=7.2 Hz, 3H), 4.16 (q, J=7.2 Hz, 2H), 4.91 (q, J=7.2 Hz, 1H), 7.15-7.26 (m, 2H), 7.32 (ddd, J=1.4, 6.8, 8.1 Hz, 1H), 7.50 (ddd, J=1.3, 8.3, 15.2 Hz, 1H), 7.57 (d, J=8.0 Hz, 1H), 7.77 (d, J=8.0 Hz, 1H), 8.14-8.24 (m, 2H), $^{13}$C NMR (50 MHz, CDCl$_3$): δ 14.1 (q), 16.8 (q), 36.1 (d), 61.0 (t), 112.4 (d), 115.5 (d, J=21.6 Hz, 2C), 122.4 (d), 123.6 (d), 126.7 (s), 128.2 (d), 129.3 (s), 132.7 (d, J=9.1 Hz, 2C), 133.7 (s), 147.5 (s), 154.3 (s), 165.1 (s, J=255.1 Hz), 173.1 (s), 184.1 (s) ppm; IR (neat): ν 3444, 3069, 2932, 1909, 1735, 1645, 1598, 1446, 1347, 1234, 1159, 1046, 878, 750 cm$^{-1}$; HRMS (ESI) calcd for C$_{20}$H$_{17}$O$_4$FNa (M$^+$+Na): 363.1003; found: 363.1002.

Example: 50

Methyl 2-(2-(4-fluorobenzoyl)benzofuran-3-yl)butanoate (3be)

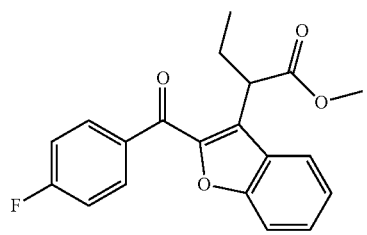 [SMILES: CCC(C(=O)OC)c1c(C(=O)c2ccc(F)cc2)oc2ccccc12]

Isolated by column chromatography (pet.ether/AcOEt=9:1, $R_f$=0.5). The title compound was determined as colourless oil (90%), and the ratio of branch to linear product (87:13). $^1$H NMR (200 MHz, CDCl$_3$): δ 0.94 (t, J=7.5 Hz, 3H), 1.91-2.13 (m, 1H), 2.26-2.48 (m, 1H), 3.67 (s, 3H), 4.84 (dd, J=6.7, 8.7 Hz, 1H), 7.15-7.26 (m, 2H), 7.32 (ddd, J=1.4, 6.7, 8.1 Hz, 1H), 7.50 (dt, J=1.3, 8.3 Hz, 1H), 7.57 (d, J=7.7 Hz, 1H), 7.85 (d, J=7.8 Hz, 1H), 8.13-8.23 (m, 2H); $^{13}$C NMR (50 MHz, CDCl$_3$): δ 12.1 (q), 24.8 (t), 42.9 (d), 52.1 (q), 112.3 (d), 115.5 (d, J=22.0 Hz, 2C), 123.0 (d), 123.7 (d), 126.9 (s), 127.4 (s), 128.2 (d), 132.6 (d, J=9.2 Hz, 2C), 133.7 (s), 148.3 (s), 154.3 (s), 165.1 (s, J=254.7 Hz), 173.2 (s), 184.2 (s) ppm; IR (neat): ν 3073, 2968, 1944, 1737, 1647, 1599, 1560, 1435, 1263, 1231, 1158, 980, 877, 749, 625 cm$^{-1}$; HRMS (ESI) calcd for C$_{20}$H$_{17}$O$_4$FNa (M$^+$+Na): 363.1003; found: 363.1001.

Example: 51

Methyl 4-(2-(4-fluorobenzoyl)benzofuran-3-yl)butanoate (5be)

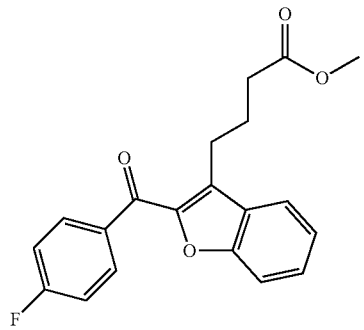

Isolated by column chromatography (pet.ether/AcOEt=9:1, $R_f$=0.4). The title compound was determined as colourless oil. $^1$H NMR (500 MHz, CDCl$_3$): δ 2.10 (qt, J=7.5 Hz, 2H), 2.44 (t, J=7.3 Hz, 2H), 3.20 (t, J=7.3 Hz, 2H), 3.66 (s, 3H), 7.17-7.21 (m, 2H), 7.34 (dt, J=1.1, 7.1 Hz, 1H), 7.49 (dt, J=1.2, 7.0 Hz, 1H), 7.54 (d, J=8.2 Hz, 1H), 7.77 (d, J=7.6 Hz, 1H), 8.15-8.18 (m, 2H); $^{13}$C NMR (125 MHz, CDCl$_3$): δ 23.7 (t), 24.7 (t), 33.5 (t), 51.5 (q), 112.3 (d), 115.5 (d, J=21.0 Hz, 2C), 121.7 (d), 123.6 (d), 128.3 (d), 128.4 (s), 130.7 (s), 132.5 (d, J=9.5 Hz, 2C), 133.9 (s), 148.1 (s), 154.3 (s), 165.1 (s, J=254.6 Hz), 173.8 (s), 183.9 (s) ppm; IR (neat): ν 3067, 2950, 1942, 1736, 1645, 1598, 1437, 1303, 1233, 1158, 880, 748, 624 cm$^{-1}$; HRMS (ESI) calcd for C$_{20}$H$_{17}$O$_4$FNa (M$^+$+Na): 363.1003; found: 363.1001.

Example: 52

Methyl 2-(2-(4-methoxybenzoyl)benzofuran-3-yl)propanoate (3ca)

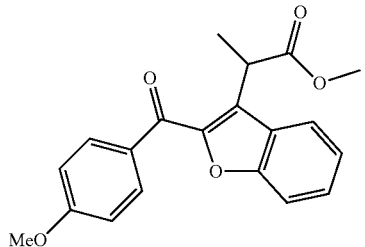 [SMILES: COC(=O)C(C)c1c(C(=O)c2ccc(OC)cc2)oc2ccccc12]

Isolated by column chromatography (pet.ether/AcOEt=9:1, $R_f$=0.5). The title compound was determined as colourless oil (83%), and the ratio of branch to linear product (91:9). $^1$H NMR (400 MHz, CDCl$_3$): δ 1.65 (d, J=7.3 Hz, 3H), 3.66 (s, 3H), 3.91 (s, 3H), 4.93 (q, J=7.2 Hz, 1H), 7.01 (d, J=8.7 Hz, 2H), 7.31 (dt, J=0.9, 7.8 Hz, 1H), 7.47 (dt, J=1.4, 8.7 Hz, 1H), 7.56 (d, J=8.3 Hz, 1H), 7.73 (d, J=8.3 Hz, 1H), 8.17 (d, J=8.7 Hz, 2H); $^{13}$C NMR (100 MHz, CDCl$_3$): δ 16.9 (q), 35.9 (d), 52.2 (q), 55.5 (q), 112.4 (d), 113.7 (d, 2C), 122.2 (d), 123.6 (d), 126.8 (s), 127.8 (d), 128.2 (s), 130.1 (s), 132.5 (d, 2C), 148.1 (s), 154.2 (s), 163.6 (s), 173.9 (s), 184.2 (s) ppm; IR (neat): ν 3453, 2953, 1954, 1736, 1643, 1600, 1437, 1364, 1258, 1170, 1027, 989, 878, 754 cm$^{-1}$; HRMS (ESI) calcd for C$_{20}$H$_{19}$O$_5$ (M$^+$+H): 339.1227; found: 339.1226.

Example: 53

Ethyl 2-(2-(4-methoxybenzoyl)benzofuran-3-yl)propanoate (3cb)

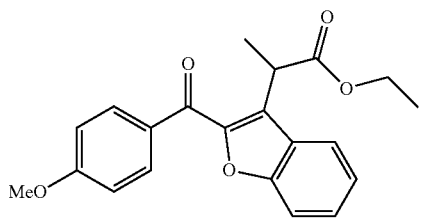 [SMILES: CCOC(=O)C(C)c1c(C(=O)c2ccc(OC)cc2)oc2ccccc12]

Isolated by column chromatography (pet.ether/AcOEt=9:1, R$_f$=0.5). The title compound was determined as colourless oil (80%), and the ratio of branch to linear product (92:8). $^1$H NMR (200 MHz, CDCl$_3$): δ 1.15 (t, J=7.2 Hz, 3H), 1.66 (d, J=7.2 Hz, 3H), 3.92 (s, 3H), 4.15 (q, J=7.1 Hz, 2H), 4.89 (q, J=7.2 Hz, 1H), 7.02 (d, J=8.8 Hz, 2H), 7.33 (d, J=1.3, 6.8 Hz, 1H), 7.47 (dt, J=1.1, 8.3 Hz, 1H), 7.57 (d, J=8.2 Hz, 1H), 7.75 (d, J=8.0 Hz, 1H), 8.18 (d, J=9.0 Hz, 2H); $^{13}$C NMR (125 MHz, CDCl$_3$): δ 14.1 (q), 16.9 (q), 36.1 (d), 55.5 (q), 61.0 (t), 112.4 (d), 113.7 (d, 2C), 122.3 (d), 123.5 (d), 126.8 (s), 127.8 (d), 128.3 (s), 130.2 (s), 132.5 (d, 2C), 148.1 (s), 154.2 (s), 163.5 (s), 173.4 (s), 184.2 (s) ppm; IR (neat): ν 3070, 2981, 1732, 1638, 1600, 1572, 1456, 1298, 1258, 1167, 1029, 878, 749 cm$^{-1}$; HRMS (ESI) calcd for C$_{21}$H$_{21}$O$_5$ (M$^+$+H): 353.1384; found: 353.1382.

Example: 54

Methyl 2-(2-(4-methoxybenzoyl)benzofuran-3-yl)butanoate (3ce)

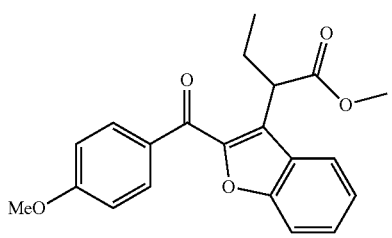 [SMILES: CCC(C(=O)OC)c1c(C(=O)c2ccc(OC)cc2)oc2ccccc12]

Isolated by column chromatography (pet.ether/AcOEt=9:1, R$_f$=0.5). The title compound was determined as colourless oil (86%), and the ratio of branch to linear product (91:9). $^1$H NMR (200 MHz, CDCl$_3$): δ 0.94 (t, J=7.5 Hz, 3H), 1.90-2.13 (m, 1H), 2.25-2.46 (m, 1H), 3.67 (s, 3H), 3.91 (s, 3H), 4.82 (dd, J=6.8, 8.6 Hz, 1H), 7.02 (d, J=8.6 Hz, 2H), 7.26-7.35 (m, 1H), 7.43-7.51 (m, 1H), 7.56 (d, J=8.1 Hz, 1H), 7.84 (d, J=8.0 Hz, 1H), 8.16 (d, J=8.7 Hz, 2H); $^{13}$C NMR (50 MHz, CDCl$_3$): δ 12.1 (q), 24.8 (t), 42.9 (d), 52.0 (q), 55.5 (q), 112.3 (d), 113.7 (d, 2C), 122.9 (d), 123.5 (d), 126.4 (s), 126.9 (s), 127.7 (d), 130.2 (s), 132.5 (d, 2C), 148.9 (s), 154.2 (s), 163.5 (s), 173.4 (s), 184.3 (s) ppm; IR (neat): ν 3017, 2967, 1736, 1639, 1599, 1509, 1460, 1360, 1260, 1113, 1030, 877, 752, 626 cm$^{-1}$; HRMS (ESI) calcd for C$_{21}$H$_{21}$O$_5$ (M$^+$+H): 353.1384; found: 353.1383.

Example: 55

Methyl 2-(2-benzoyl-5-methylbenzofuran-3-yl)propanoate (3da)

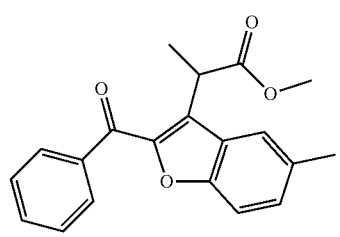 [SMILES: COC(=O)C(C)c1c(C(=O)c2ccccc2)oc2ccc(C)cc12]

Isolated by column chromatography (pet.ether/AcOEt=9:1, R$_f$=0.5). The title compound was determined as colourless solid (82%), and the ratio of branch to linear product (88:12). Mp: 114-115° C.; $^1$H NMR (400 MHz, CDCl$_3$): δ 1.65 (d, J=7.3 Hz, 3H), 2.46 (s, 3H), 3.67 (s, 3H), 4.93 (q, J=7.3 Hz, 1H), 7.29 (dd, J=1.8, 8.7 Hz, 1H), 7.43 (d, J=8.2 Hz, 1H), 7.50-7.54 (m, 3H), 7.61 (tt, J=1.4, 7.3 Hz, 1H), 8.09-8.12 (m, 2H), $^{13}$C NMR (100 MHz, CDCl$_3$): δ 16.8 (q), 21.5 (q), 35.9 (d), 52.2 (q), 112.0 (d), 121.6 (d), 126.8 (s), 128.3 (d, 2C), 128.6 (s), 129.8 (d), 130.0 (d, 2C), 132.8 (d), 133.4 (s), 137.4 (s), 147.9 (s), 152.9 (s), 173.8 (s), 185.9 (s) ppm; IR (neat): ν 2949, 1739, 1645, 1563, 1448, 1300, 1206, 1057, 905, 804, 720 cm$^{-1}$; HRMS (ESI) calcd for C$_{20}$H$_{19}$O$_4$ (M$^+$+H): 323.1278; found: 323.1276.

Example: 56

Ethyl 2-(2-benzoyl-5-methylbenzofuran-3-yl)propanoate (3db)

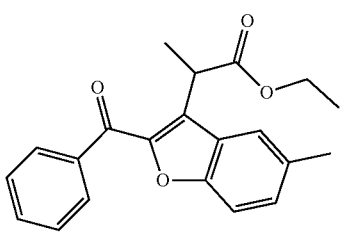 [SMILES: CCOC(=O)C(C)c1c(C(=O)c2ccccc2)oc2ccc(C)cc12]

Isolated by column chromatography (pet.ether/AcOEt=9:1, R$_f$=0.5). The title compound was determined as colourless oil (79%), and the ratio of branch to linear product (86:14). $^1$H NMR (500 MHz, CDCl$_3$): δ 1.15 (t, J=7.3 Hz, 3H), 1.64 (d, J=7.0 Hz, 3H), 2.46 (s, 3H), 4.15 (q, J=7.3 Hz, 2H), 4.88 (q, J=7.0 Hz, 1H), 7.29 (dd, J=1.5, 8.5 Hz, 1H), 7.43 (d, J=8.2 Hz, 1H), 7.50-7.53 (m, 3H), 7.61 (tt, J=1.2, 7.3 Hz, 1H), 8.08-8.11 (m, 2H); $^{13}$C NMR (125 MHz, CDCl$_3$): δ 14.1 (q), 16.8 (q), 21.4 (q), 36.1 (d), 61.0 (t), 112.0 (d), 121.8 (d), 126.8 (s), 128.3 (d, 2C), 128.8 (s), 129.7 (d), 129.9 (d, 2C), 132.8 (d), 133.2 (s), 137.5 (s), 147.9 (s), 152.9 (s), 173.3 (s), 185.9 (s) ppm; IR (neat): ν 2981, 1945, 1743,

Example: 57

Methyl 2-(2-benzoyl-5-methylbenzofuran-3-yl)butanoate (3de)

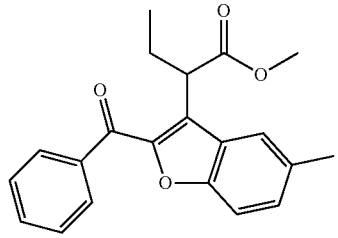 [SMILES: CCC(C(=O)OC)c1c(C(=O)c2ccccc2)oc2ccc(C)cc12]

Isolated by column chromatography (pet.ether/AcOEt=9:1, $R_f$=0.5). The title compound was determined as colourless oil (80%), and the ratio of branch to linear product (85:15). $^1$H NMR (400 MHz, CDCl$_3$): δ 0.92 (t, J=7.3 Hz, 3H), 1.97-2.06 (m, 1H), 2.29-2.38 (m, 1H), 2.46 (s, 3H), 3.67 (s, 3H), 4.81 (dd, J=6.9, 8.7 Hz, 1H), 7.29 (dd, 1.8, 8.7 Hz, 1H), 7.42 (d, J=8.7 Hz, 1H), 7.50-7.53 (m, 2H), 7.58-7.63 (m, 2H), 8.06-8.09 (m, 2H); $^{13}$C NMR (100 MHz, CDCl$_3$): δ 12.1 (q), 21.5 (q), 24.7 (t), 42.9 (d), 52.1 (q), 111.9 (d), 122.3 (d), 126.9 (s), 127.0 (s), 128.3 (d, 2C), 129.7 (d), 129.9 (d, 2C), 132.8 (d), 133.3 (s), 137.6 (s), 148.7 (s), 152.9 (s), 173.4 (s), 186.0 (s) ppm; IR (neat): ν 3350, 2929, 1944, 1736, 1648, 1560, 1436, 1267, 1159, 1042, 907, 803, 694 cm$^{-1}$; HRMS (ESI) calcd for C$_{21}$H$_{21}$O$_4$ (M$^+$+H): 337.1434; found: 337.1432.

Example: 58

Methyl 2-(2-benzoyl-5-chlorobenzofuran-3-yl)propanoate (3ea)

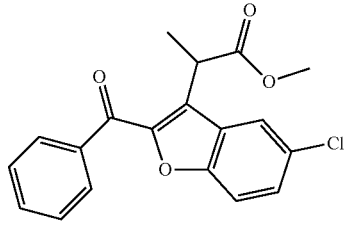

Isolated by column chromatography (pet.ether/AcOEt=9:1, $R_f$=0.5). The title compound was determined as colourless solid (87%), the ratio of branch to linear product (91:9). Mp: 90-91° C.; $^1$H NMR (500 MHz, CDCl$_3$): δ 1.65 (d, J=7.3 Hz, 3H), 3.69 (s, 3H), 4.89 (q, J=7.3 Hz, 1H), 7.43 (dd, J=2.1, 8.9 Hz, 1H), 7.48 (d, J=8.9 Hz, 1H), 7.51-7.54 (m, 2H), 7.63 (t, J=7.3 Hz, 1H), 7.73 (d, J=1.8 Hz, 1H), 8.07-8.08 (m, 2H); $^{13}$C NMR (125 MHz, CDCl$_3$): δ 16.9 (q), 35.8 (d), 52.4 (q), 113.6 (d), 121.8 (d), 128.0 (s, 2C), 128.4 (d, 2C), 128.5 (d), 129.4 (s), 129.9 (d, 2C), 133.2 (d), 137.1 (s), 148.8 (s), 152.7 (s), 173.4 (s), 185.7 (s) ppm; IR (neat): ν 2953, 1956, 1735, 1453, 1437, 1369, 1257, 1199, 1173, 988, 857, 757 cm$^{-1}$; HRMS (ESI) calcd for C$_{19}$H$_{16}$O$_4$Cl (M$^+$+H): 343.0732; found: 343.0733.

Example: 59

Ethyl 2-(2-benzoyl-5-chlorobenzofuran-3-yl)propanoate (3eb)

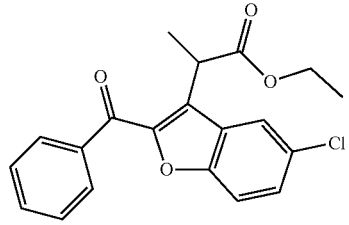

Isolated by column chromatography (pet.ether/AcOEt=9:1, $R_f$=0.5). The title compound was determined as colourless oil (86%), and the ratio of branch to linear product (93:7). $^1$H NMR (200 MHz, CDCl$_3$): δ 1.17 (t, J=7.1 Hz, 3H), 1.64 (d, J=7.3 Hz, 3H), 4.16 (q, J=7.1 Hz, 2H), 4.84 (q, J=7.3 Hz, 1H), 7.43-7.46 (m, 1H), 7.50 (d, J=8.7 Hz, 1H), 7.55 ((t, J=7.8 Hz, 2H),) 7.61-7.65 (m, 1H), 7.74 (d, J=1.8 Hz, 1H), 8.05-8.09 (m, 2H); $^{13}$C NMR (100 MHz, CDCl$_3$): δ 14.1 (q), 16.9 (q), 36.1 (d), 61.2 (t), 113.6 (d), 122.0 (d), 128.0 (s), 128.2 (s), 128.4 (d, 3C), 129.3 (s), 129.9 (d, 2C), 133.1 (d), 137.1 (s), 148.8 (s), 152.7 (s), 172.9 (s), 185.7 (s) ppm; IR (neat): ν 3036, 2928, 1733, 1650, 1598, 1557, 1447, 1295, 1197, 1068, 961, 806, 723, 694 cm$^{-1}$; HRMS (ESI) calcd for C$_{20}$H$_{18}$O$_4$Cl (M$^+$+H): 357.0888; found: 357.0887.

Example: 60

Methyl 2-(2-benzoyl-5-chlorobenzofuran-3-yl)butanoate (3ee)

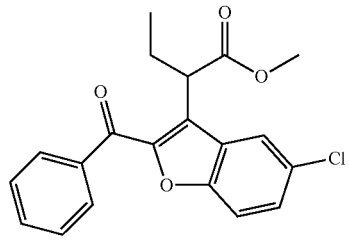 [SMILES: CCC(C(=O)OC)c1c(C(=O)c2ccccc2)oc2ccc(Cl)cc12]

Isolated by column chromatography (pet.ether/AcOEt=9:1, $R_f$=0.5). The title compound was determined as colourless solid (89%), and the ratio of branch to linear product (91:9). Mp: 88-89° C.; $^1$H NMR (500 MHz, CDCl$_3$): δ 0.93 (t, J=7.6 Hz, 3H), 1.95-2.04 (m, 1H), 2.28-2.37 (m, 1H), 3.69 (s, 3H), 4.77 (dd, J=6.4, 8.8 Hz, 1H), 7.43 (dd, J=1.9, 8.5 Hz, 1H), 7.47 (d, J=8.5 Hz, 1H), 7.51-7.54 (m, 2H), 7.63 (tt, J=1.2, 7.3 Hz, 1H), 7.83 (d, J=2.1 Hz, 1H), 8.05-8.06 (m, 2H); $^{13}$C NMR (125 MHz, CDCl$_3$): δ 12.1 (q), 24.9 (t), 42.9 (d), 52.2 (q), 113.5 (d), 122.5 (d), 126.3 (s), 128.1 (s), 128.4 (d, 2C), 128.5 (d), 129.4 (s), 129.9 (d, 2C), 133.1 (d), 137.2 (s), 149.6 (s), 152.7 (s), 173.0 (s), 185.8 (s) ppm; IR (neat): ν 3019,

Example: 61

Methyl 2-(2-acetylbenzofuran-3-yl)propanoate (3ha)

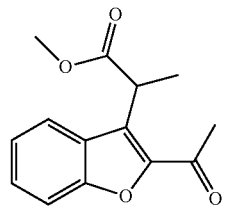 [SMILES: COC(=O)C(C)c1c(C(C)=O)oc2ccccc12]

Isolated by column chromatography (pet.ether/AcOEt=9.5:0.5, $R_f$=0.4). The title compound was determined as colourless oil (71%), and the ratio of branch to linear product (48:52). $^1$H NMR (500 MHz, CDCl$_3$): δ 1.59 (d, J=7.0 Hz, 3H), 2.65 (s, 3H), 3.66 (s, 3H), 5.01 (q, J=7.0 Hz, 1H), 7.29 (td, J=0.9, 8.2 Hz, 1H), 7.48 (ddd, J=1.2, 7.0, 8.2 Hz, 1H), 7.54 (d, J=8.2 Hz, 1H), 7.69 (d, J=8.2 Hz, 1H); $^{13}$C NMR (125 MHz, CDCl$_3$): δ 16.7 (q), 27.9 (q), 35.4 (q), 52.2 (q), 112.4 (d), 122.5 (d), 123.6 (d), 126.3 (s), 126.9 (s), 128.1 (d), 147.3 (s), 154.1 (s), 173.7 (s), 191.7 (s) ppm; IR (neat): ν 2986, 2401, 1733, 1645, 1564, 1260, 1215, 1060, 876, 759, 668 cm$^{-1}$; HRMS (ESI) calcd for C$_{14}$H$_{14}$O$_4$Na (M$^+$+Na): 269.0784; found: 269.0782.

Example: 62

Methyl 3-(2-benzoylbenzofuran-3-yl)propanoate (4ha)

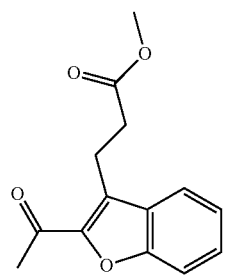 [SMILES: COC(=O)CCc1c(C(C)=O)oc2ccccc12]

Isolated by column chromatography (pet.ether/AcOEt=9:1, $R_f$=0.2). $^1$H NMR (400 MHz, CDCl$_3$): δ 2.64 (s, 3H), 2.73 (t, J=7.5 Hz, 2H), 3.38 (t, J=7.5 Hz, 2H), 3.63 (s, 3H), 7.33 (dd, J=6.8, 7.8 Hz, 1H), 7.47-7.50 (m, 1H), 7.53 (d, J=7.8 Hz, 1H), 7.74 (d, J=8.0 Hz, 1H); $^{13}$C NMR (100 MHz, CDCl$_3$): δ 19.6 (q), 27.7 (q), 33.4 (t), 51.7 (q), 112.2 (d), 121.8 (d), 123.4 (d), 126.9 (s), 128.2 (d), 128.4 (s), 148.2 (s), 154.0 (s), 173.2 (s), 191.2 (s) ppm; IR (neat), ν 2987, 2409, 1735, 1648, 1562, 1260, 1214, 1066, 874, 753, 666 cm$^{-1}$; HRMS (ESI) calcd for C$_{14}$H$_{14}$O$_4$Na (M$^+$+Na): 269.0784; found: 269.0783.

2970, 2400, 1734, 1648, 1559, 1447, 1292, 1215, 986, 808, 756, 669 cm$^{-1}$; HRMS (ESI) calcd for C$_{20}$H$_{18}$O$_4$Cl (M$^+$+H): 357.0888; found: 357.0888.

Example: 63

2-(2-benzoylbenzofuran-3-yl)-N-isopropylpropanamide (3aj)

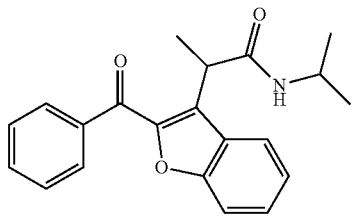 [SMILES: CC(C)NC(=O)C(C)c1c(C(=O)c2ccccc2)oc2ccccc12]

Isolated by column chromatography (pet.ether/AcOEt=7:3, $R_f$ 0.4). The title compound was determined as colourless oil (74%). $^1$H NMR (500 MHz, CDCl$_3$) δ 0.97 (d, J=6.7 Hz, 3H), 1.19 (d, J=6.7 Hz, 3H), 1.69 (d, J=7.3 Hz, 3H), 4.02 (dd, J=14.0, 6.7 Hz, 1H), 4.64 (q, J=7.1 Hz, 1H), 6.57 (d, J=7.3 Hz, 1H), 7.31-7.36 (m, 1H), 7.46-7.51 (m, 1H), 7.53 (d, J=8.2 Hz, 1H), 7.56 (t, J=7.6 Hz, 2H), 7.67 (t, J=7.5 Hz, 1H), 8.09 (d, J=7.9 Hz, 1H), 8.11-8.16 (m, 2H); $^{13}$C NMR (125 MHz, CDCl$_3$) δ 15.8 (q), 22.4 (q), 22.7 (q), 37.3 (d), 41.4 (d), 112.2 (d), 123.7 (d), 124.2 (d), 126.6 (s), 128.3 (d), 128.4 (d, 3C), 130.2 (d, 3C), 131.0 (s), 133.3 (d), 136.92 (s), 147.8 (s), 154.6 (s), 171.2 (s), 186.7 (s) ppm; IR (neat): ν 3333, 3061, 2973, 1644, 1549, 1449, 1360, 1261, 1174, 1023, 966, 826, 752 cm$^{-1}$; HRMS (ESI) calcd for C$_{21}$H$_{21}$O$_3$NNa (M$^+$+Na): 358.1414; found: 358.1411.

Example: 64

(3-phenethylbenzofuran-2-yl)(phenyl)methanone (3al) and (phenyl(3-(1-phenylethyl)benzofuran-2-yl)methanone (4al)

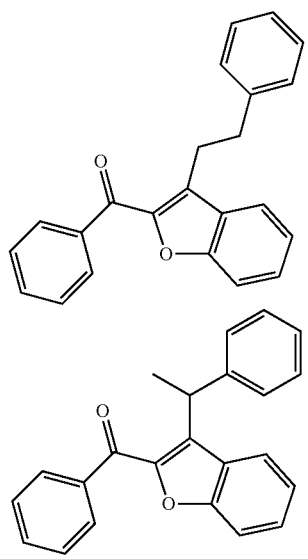

Isolated by column chromatography (pet.ether/AcOEt=9:1, $R_f$=0.5). The title compound was determined as colourless oil (83%), and the ratio of branch to linear product is (1:1). $^1$H NMR (200 MHz, CDCl$_3$): δ 1.88 (d, J=7.3 Hz, 3H), 3.04-3.08 (m, 2H), 3.43-3.47 (m, 2H), 5.43 (q, J=7.3 Hz, 1H), 7.18-7.20 (m, 3H), 7.26-7.28 (m, 5H), 7.30-7.34 (m, 3H), 7.42 (d, J=8.6 Hz, 2H), 7.46-7.49 (m, 3H), 7.54-7.57 (m, 5H), 7.61-7.64 (m, 3H), 8.09 (d, J=7.3 Hz, 2H), 8.12 (d, J=7.3 Hz, 2H) ppm; $^{13}$C NMR (100 MHz, CDCl$_3$) δ 19.2 (q), 26.8 (t), 34.5 (d), 35.9 (t), 112.3 (d), 112.3 (d), 121.4 (d), 123.1 (d), 123.3 (d), 123.4 (d), 126.0 (d), 126.3 (d), 127.0 (s), 127.5 (d, 2C), 127.6 (d), 128.1 (d), 128.2 (d), 128.3 (d, 2C), 128.3 (d, 6C), 128.4 (s), 128.5 (d, 2C), 129.7 (d, 2C), 129.9 (d), 130.5 (s), 132.6 (d), 132.7 (d), 134.3 (s), 137.7 (s), 137.8 (s), 141.4 (s), 143.5 (s), 147.4 (s), 148.2 (s), 154.2 (s), 154.6 (s), 185.7 (s), 186.3 (s) ppm; IR (neat): ν 2993, 2415, 1730, 1646, 1566, 1263, 1219, 1065, 869, 754, 667 cm$^{-1}$; HRMS (ESI) calcd for C$_{23}$H$_{19}$O$_2$ (M$^+$+H): 327.1380; found: 327.1383.

Example 65

Phenyl(3-undecylbenzofuran-2-yl)methanone (4am)

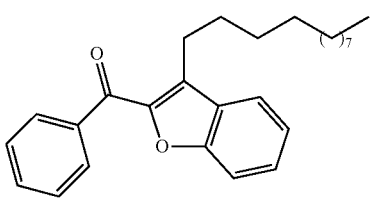

Isolated by column chromatography (pet.ether/AcOEt=9:1, R$_f$=0.6). The title compound was determined as colourless oil (65%). $^1$H NMR (500 MHz, CDCl$_3$): δ 0.89 (t, J=6.9 Hz, 3H), 1.26 (bs, 14H), 1.30-1.37 (m, 2H), 1.39-1.47 (m, 2H), 1.71-1.79 (m, 2H), 3.09-3.17 (m, 2H), 7.34 (t, J=7.48 Hz, 1H), 7.46-7.57 (m, 4H), 7.62 (d, J=7.3 Hz, 1H), 7.74 (d, J=7.93 Hz, 1H), 8.09 (d, J=7.6 Hz, 2H); $^{13}$C NMR (126 MHz, CDCl$_3$) δ 14.1 (q), 22.7 (d), 24.6 (d), 29.4 (d), 29.5 (d), 29.6 (d, 3C), 29.6 (d), 29.8 (d), 29.8 (d), 31.9 (d), 112.3 (d), 121.7 (d), 123.2 (d), 128.0 (d), 128.3 (d, 2C), 128.7 (s), 129.7 (d, 2C), 131.8 (s), 132.5 (d), 137.9 (s), 148.0 (s), 154.3 (s), 185.9 (s) ppm.

General Procedure B: Linear Hydroarylations Using [Ru(p-cymene)Cl$_2$]$_2$ 2-aroylbenzo[b]furan (0.1 mmol) was placed in a screw cap pressure tube and dissolved in anhydrous dioxane (2 mL), which was then evacuated and back filled with argon. To the reaction vessel alkene (acrylate) (0.3 mmol), NaHCO$_3$ (0.5 mmol), [Ru(p-cymene)Cl$_2$]$_2$ (0.01 mmol) and PPh$_3$ (0.03 mmol) were added. The solution was then stirred at 140° C. (bath temperature) for 24 h. The reaction mixture was cooled to room temperature. The solvent were evaporated and the crude products were purified by column chromatography (pet ether/AcOEt) to give analytically pure.

Example: 66

Methyl 3-(2-benzoylbenzofuran-3-yl)propanoate (4aa)

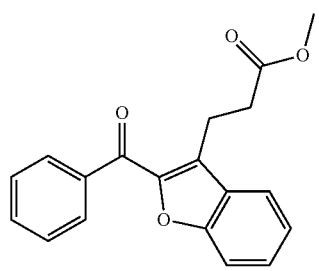 [SMILES: COC(=O)CCc1c(C(=O)c2ccccc2)oc2ccccc12]

Isolated by column chromatography (pet.ether/AcOEt=9:1, R$_f$=0.4). The title compound was determined as colourless oil (73%), and the ratio of linear to branch product (86:14). $^1$H NMR (400 MHz, CDCl$_3$): δ 2.81 (t, J=7.8 Hz, 2H), 3.44 (t, J=7.8 Hz, 2H), 3.63 (s, 3H), 7.35 (ddd, J=1.4, 6.8, 8.2 Hz, 1H), 7.47-7.55 (m, 4H), 7.59-7.64 (m, 1H), 7.78 (d, J=7.8 Hz, 1H), 8.10-8.13 (m, 2H); $^{13}$C NMR (100 MHz, CDCl$_3$): δ 20.1 (t), 33.6 (t), 51.7 (q), 112.3 (d), 121.6 (d), 123.5 (d), 128.1 (s), 128.3 (d, 3C), 129.6 (s), 129.8 (d, 2C), 132.7 (d), 137.5 (s), 148.4 (s), 154.3 (s), 173.3 (s), 185.5 (s) ppm; IR (neat): ν 3020, 2400, 1731, 1644, 1438, 1215, 1045, 850, 758, 669 cm$^{-1}$; HRMS (ESI) calcd for C$_{19}$H$_{16}$O$_4$Na (M$^+$+Na): 331.0941; found: 331.0938.

Example: 67

Ethyl 3-(2-benzoylbenzofuran-3-yl)propanoate (4ab)

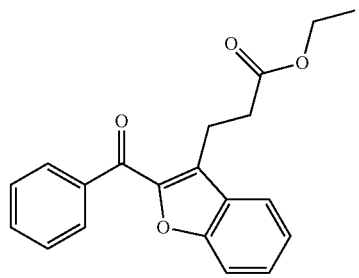 [SMILES: CCOC(=O)CCc1c(C(=O)c2ccccc2)oc2ccccc12]

Isolated by column chromatography (pet.ether/AcOEt=9:1, R$_f$=0.4). The title compound was determined as colourless oil (74%) and the ratio of linear to branch product (88:12); $^1$H NMR (400 MHz, CDCl$_3$): δ 1.18 (t, J=7.1 Hz, 3H), 2.79 (t, J=7.6 Hz, 2H), 3.44 (t, J=7.6 Hz, 2H), 4.09 (q, J=7.1 Hz, 2H), 7.32-7.36 (m, 1H), 7.47-7.54 (m, 4H), 7.59-7.63 (m, 1H), 7.79 (d, J=7.8 Hz, 1H) 8.11 (d, J=7.3 Hz 2H); $^{13}$C NMR (100 MHz, CDCl$_3$): δ 14.1 (q), 20.1 (t), 33.9 (t), 60.5 (t), 112.3 (d), 121.7 (d), 123.5 (d), 128.2 (s), 128.3 (d, 3C), 129.7 (s), 129.8 (d, 2C), 132.7 (d), 137.5 (s), 148.4 (s), 154.3 (s), 172.8 (s), 185.5 (s) ppm; IR (neat): ν 2960, 2934, 2874, 1735, 1654, 1599, 1465, 1261, 1175, 973, 876, 751 cm$^{-1}$; HRMS (ESI) calcd for C$_{20}$H$_{18}$O$_4$Na (M$^+$+Na): 345.1097; found: 345.1095.

Example: 68

Butyl 3-(2-benzoylbenzofuran-3-yl)propanoate (4ac)

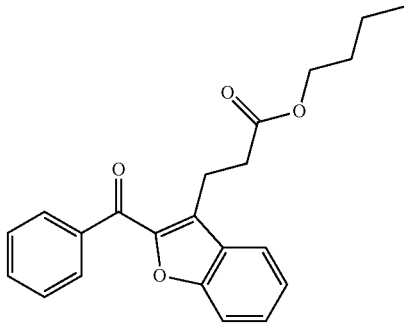 [SMILES: CCCCOC(=O)CCc1c(C(=O)c2ccccc2)oc2ccccc12]

Isolated by column chromatography (pet.ether/AcOEt=9:1, R$_f$=0.4). The title compound was determined as colourless oil (79%) and the ratio of linear to branch product (86:14). $^1$H NMR (400 MHz, CDCl$_3$): δ 0.88 (t, J=7.3 Hz, 3H), 1.26-1.33 (m, 2H), 1.50-1.57 (m, 2H), 2.81 (t, J=7.6 Hz, 2H), 3.45 (t, J=7.6 Hz, 2H), 4.03 (t, J=6.7 Hz, 2H), 7.34-7.37 (m, 1H), 7.49-7.56 (m, 4H), 7.61-7.65 (m, 1H), 7.80 (d, J=7.7 Hz, 1H), 8.12 (d, J=7.7 Hz, 2H); $^{13}$C NMR (100 MHz, CDCl$_3$): δ 13.7 (q), 19.0 (t), 20.1 (t), 30.5 (t), 33.8 (t), 64.5 (t), 112.3 (d), 121.7 (d), 123.5 (d), 128.2 (s), 128.3 (d, 3C), 129.8 (s), 129.8 (d, 2C), 132.8 (d), 137.5 (s), 148.4 (s), 154.3 (s), 173.0 (s), 185.5 (s) ppm; IR (neat): ν 3059, 2960, 2935, 2874, 1735, 1654, 1560, 1449, 1355, 1263, 1175, 876, 751, 725 cm$^{-1}$; HRMS (ESI) calcd for C$_{22}$H$_{22}$O$_4$Na (M$^+$+Na): 373.1410; found: 373.1410.

Example: 69

Methyl 3-(2-(4-fluorobenzoyl)benzofuran-3-yl)propanoate (4ba)

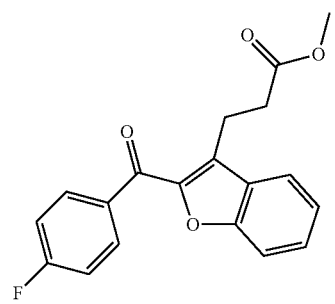 [SMILES: COC(=O)CCc1c(C(=O)c2ccc(F)cc2)oc2ccccc12]

Isolated by column chromatography (pet.ether/AcOEt=9:1, R$_f$=0.4). The title compound was determined as colourless oil (66%), and the ratio of linear to branch product (86:14). $^1$H NMR (400 MHz, CDCl$_3$): δ 2.82 (t, J=7.5 Hz, 2H), 3.45 (t, J=7.5 Hz, 2H), 3.64 (s, 3H), 7.19-7.23 (m, 2H), 7.37 (t, J=7.3 Hz, 1H), 7.49-7.53 (m, 1H), 7.56 (d, J=8.3 Hz, 1H), 7.80 (d, J=8.0 Hz, 1H), 8.19-8.22 (m, 2H); $^{13}$C NMR (100 MHz, CDCl$_3$): δ 20.1 (t), 33.6 (t), 51.7 (q), 112.3 (d), 115.5 (d, J=21.6 Hz, 2C), 121.7 (d), 123.6 (d), 128.1 (s), 128.4 (d), 130.0 (s, 2C), 132.6 (d, J=9.3 Hz, 2C), 148.2 (s), 154.2 (s), 173.2 (s, 2C), 183.7 (s) ppm; IR (neat): ν 2951, 1736, 1642, 1598, 1559, 1437, 1290, 1233, 1158, 1047, 878, 849, 748 cm$^{-1}$; HRMS (ESI) calcd for C$_{19}$H$_{15}$O$_4$FNa (M$^+$+Na): 349.0847; found: 349.0843.

Example: 70

Ethyl 3-(2-(4-fluorobenzoyl)benzofuran-3-yl)propanoate (4bb)

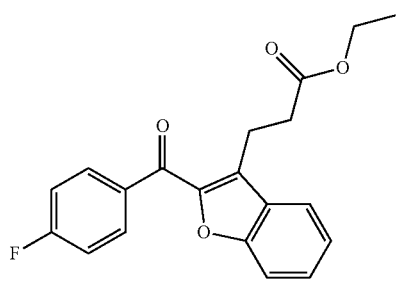 [SMILES: CCOC(=O)CCc1c(C(=O)c2ccc(F)cc2)oc2ccccc12]

Isolated by column chromatography (pet.ether/AcOEt=9:1, R$_f$=0.4). The title compound was determined as colourless oil (74%), and the ratio of linear to branch product (77:23); $^1$H NMR (400 MHz, CDCl$_3$): δ 1.19 (t, J=7.3 Hz, 3H), 2.80 (t, J=7.6 Hz, 2H), 3.45 (t, J=7.6 Hz, 2H), 4.10 (q, J=7.2 Hz, 2H), 7.19-7.23 (m, 2H), 7.36 (t, 7.8 Hz, 1H), 7.51 (ddd, J=1.3, 8.3, 15.2 Hz, 1H), 7.55 (d, J=8.3 Hz, 1H), 7.80 (d, J=8.1 Hz, 1H), 8.18-8.22 (m, 2H); $^{13}$C NMR (100 MHz, CDCl$_3$): δ 14.1 (q), 20.1 (t), 33.8 (t), 60.5 (t), 112.2 (d), 115.5 (d, J=21.6 Hz, 2C), 121.7 (d), 123.6 (d), 128.2 (s), 128.4 (d), 130.1 (s), 132.6 (d, J=9.3 Hz, 2C), 133.7 (s), 148.2 (s), 154.2 (s), 165.5 (s, J=255.1 Hz), 172.8 (s), 183.7 (s) ppm; IR (neat): ν 3069, 2982, 1909, 1735, 1645, 1598, 1506, 1446, 1347, 1266, 1099, 954, 878, 750, 625 cm$^{-1}$; HRMS (ESI) calcd for C$_{20}$H$_{17}$O$_4$FNa (M$^+$+Na): 363.1003; found: 363.1003.

Example: 71

Methyl 3-(2-(4-methoxybenzoyl)benzofuran-3-yl)propanoate (4ca)

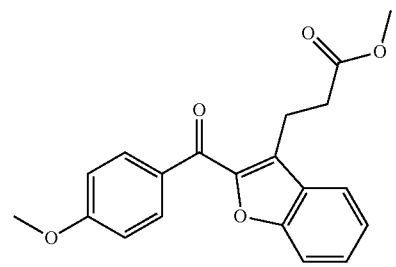

Isolated by column chromatography (pet.ether/AcOEt=9:1, R$_f$=0.4). The title compound was determined as colourless oil (64%) and the ratio of linear to branch product (73:27). Mp: 78-79° C.; $^1$H NMR (400 MHz, CDCl$_3$): δ 2.82 (t, J=7.7 Hz, 2H), 3.45 (t, J=7.7 Hz, 2H), 3.65 (s, 3H), 3.92 (s, 3H), 7.03 (d, J=8.8 Hz, 2H), 7.34-7.38 (m, 1H), 7.48-7.52 (m, 1H), 7.56 (d, J=8.3 Hz, 1H), 7.78 (d, J=7.8 Hz, 1H), 8.20 (d, J=9.0 Hz, 2H); $^{13}$C NMR (100 MHz, CDCl$_3$): δ 20.1 (t), 33.7 (t), 51.6 (q), 55.5 (q), 112.2 (d), 113.7 (d, 2C), 121.5

(d), 123.4 (d), 128.0 (d), 128.2 (s), 128.9 (s), 130.2 (s), 132.3 (d, 2C), 148.8 (s), 154.1 (s), 163.4 (s), 173.3 (s), 183.8 (s) ppm; IR (neat): ν 3019, 2400, 1732, 1635, 1600, 1421, 1259, 1215, 1121, 1032, 928, 845, 757, 669 cm$^{-1}$; HRMS (ESI) calcd for $C_{20}H_{18}O_5Na$ (M$^+$+Na): 361.1046; found: 361.1046.

Example: 72

Ethyl 3-(2-(4-methoxybenzoyl)benzofuran-3-yl)propanoate (4cb)

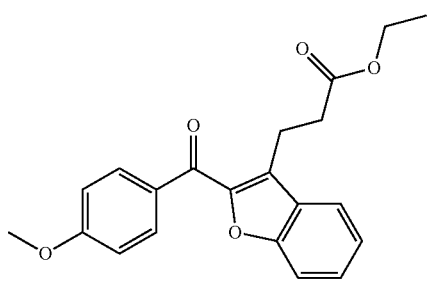 [SMILES: CCOC(=O)CCc1c(C(=O)c2ccc(OC)cc2)oc2ccccc12]

Isolated by column chromatography (pet.ether/AcOEt=9:1, $R_f$=0.4). The title compound was determined as colourless oil (72%), and the ratio of linear to branch product is (60:40). $^1$H NMR (400 MHz, CDCl$_3$): δ 1.18 (t, J=7.2 Hz, 3H), 2.79 (t, J=7.6 Hz, 2H), 3.42 (t, J=7.6 Hz, 2H), 3.90 (s, 3H), 4.08 (q, J=7.2 Hz, 2H), 7.00-7.03 (m, 2H), 7.33 (ddd, J=0.9, 6.8, 7.8 Hz, 1H), 7.48 (ddd, J=1.4, 7.3, 8.7 Hz, 1H), 7.53-7.56 (m, 1H), 7.79 (dd, J=1.1, 7.8 Hz, 1H), 8.17-8.20 (m, 2H); $^{13}$C NMR (100 MHz, CDCl$_3$): δ 14.1 (q), 20.1 (t), 33.9 (t), 55.5 (q), 60.5 (t), 112.2 (d), 113.7 (d, 2C), 121.6 (d), 123.4 (d), 128.0 (d), 128.3 (s), 129.0 (s), 130.3 (s), 132.3 (d, 2C), 148.8 (s), 154.1 (s), 163.4 (s), 172.9 (s), 183.8 (s) ppm; IR (neat): ν 3020, 2982, 2928, 2855, 1731, 1636, 1600, 1510, 1446, 1372, 1295, 1259, 1166, 1030, 878, 755, 667 cm$^{-1}$; HRMS (ESI) calcd for $C_{23}H_{20}O_5Na$ (M$^+$+Na): 375.1203; found: 375.1201.

Example: 73

Methyl 3-(2-benzoyl-5-methylbenzofuran-3-yl)propanoate (4da)

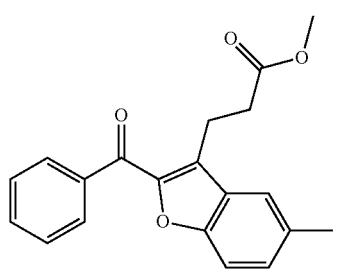 [SMILES: COC(=O)CCc1c(C(=O)c2ccccc2)oc2ccc(C)cc12]

Isolated by column chromatography (pet.ether/AcOEt=9:1, $R_f$=0.4). The title compound was determined as colourless solid (69%), and the ratio of linear to branch product (82:18). Mp: 71-72° C.; $^1$H NMR (400 MHz, CDCl$_3$): δ 2.48 (s, 3H), 2.79 (t, J=7.9 Hz, 2H), 3.41 (t, J=7.9 Hz, 2H), 3.65 (s, 3H), 7.30 (d, J=8.5 Hz, 1H), 7.42 (d, J=8.5 Hz, 1H), 7.50-7.53 (m, 3H), 7.58-7.62 (m, 1H), 8.10 (d, J=7.8 Hz, 2H); $^{13}$C NMR (100 MHz, CDCl$_3$): δ 20.1 (t), 21.4 (q), 33.6 (t), 51.7 (q), 111.9 (d), 121.0 (d), 128.2 (s), 128.3 (d, 2C), 129.4 (s), 129.8 (d, 2C), 129.9 (d), 132.7 (d), 133.2 (s), 137.6 (s), 148.6 (s), 152.8 (s), 173.3 (s), 185.5 (s) ppm; IR (neat): ν 2997, 2954, 2850, 1736, 1659, 1599, 1437, 1319, 1271, 911, 857, 722 cm$^{-1}$; HRMS (ESI) calcd for $C_{20}H_{18}O_4Na$ (M$^+$+Na): 345.1097; found: 345.1094.

Example: 74

Ethyl 3-(2-benzoyl-5-methylbenzofuran-3-yl)propanoate (4db)

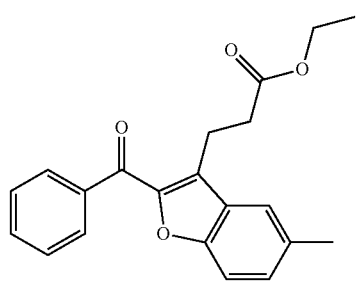 [SMILES: CCOC(=O)CCc1c(C(=O)c2ccccc2)oc2ccc(C)cc12]

Isolated by column chromatography (pet.ether/AcOEt=9:1, $R_f$=0.4). The title compound was determined as colourless oil (65%) and the ratio of linear to branch product (94:6). $^1$H NMR (500 MHz, CDCl$_3$): δ 1.20 (t, J=7.1 Hz, 3H), 2.48 (s, 3H), 2.77 (t, J=7.5 Hz, 2H), 3.41 (t, J=7.5 Hz, 2H), 4.10 (q, J=7.1 Hz, 2H), 7.30 (d, J=8.5 Hz, 1H), 7.41 (d, J=8.5 Hz, 1H), 7.50-7.53 (m, 3H), 7.58-7.62 (m, 1H), 8.10 (d, J=7.6 Hz, 2H); $^{13}$C NMR (125 MHz, CDCl$_3$): δ 14.2 (q), 20.1 (t), 21.4 (q), 33.9 (t), 60.5 (t), 111.9 (d), 121.1 (d), 128.3 (d, 2C), 128.3 (s), 129.5 (s), 129.8 (d, 2C), 129.9 (d), 132.6 (d), 133.2 (s), 137.7 (s), 148.6 (s), 152.9 (s), 172.9 (s), 185.5 (s). ppm; IR (neat): ν 2982, 2936, 2874, 1945, 1732, 1655, 1563, 1447, 1370, 1263, 1182, 1035, 977, 861, 757 cm$^{-1}$; HRMS (ESI) calcd for $C_{21}H_{20}O_4Na$ (M$^+$+Na): 359.1254; found: 359.1251.

Example: 75

Methyl 3-(2-benzoyl-5-chlorobenzofuran-3-yl)propanoate (4ea)

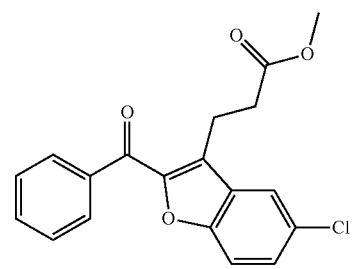 [SMILES: COC(=O)CCc1c(C(=O)c2ccccc2)oc2ccc(Cl)cc12]

Isolated by column chromatography (pet.ether/AcOEt=9:1, $R_f$=0.4). The title compound was determined as colourless solid (76%) and the ratio of linear to branch product (92:8); Mp: 82-83° C.; $^1$H NMR (400 MHz, CDCl$_3$): δ 2.79 (t, J=7.6 Hz, 2H), 3.38 (t, J=7.6 Hz, 2H), 3.64 (s, 3H), 7.42-7.54 (m, 4H), 7.59-7.66 (tt, J=1.4, 3.7 Hz, 1H), 7.75 (d, J=2.3 Hz, 1H), 8.07-8.10 (m, 2H); $^{13}$C NMR (100 MHz, CDCl$_3$): δ 20.0 (t), 33.5 (t), 51.7 (q), 113.4 (d), 121.1 (d), 128.4 (d, 2C), 128.6 (d), 128.8 (s), 129.3 (s), 129.5 (s), 129.8 (d, 2C), 133.0 (d), 137.1 (s), 149.4 (s), 152.5 (s), 173.0 (s), 185.3 (s) ppm; IR (neat): ν 3022, 2953, 2926, 2854, 1735, 1647, 1557, 1448, 1282, 1216, 1062, 808, 758, 694 cm$^{-1}$; HRMS (ESI) calcd for C$_{19}$H$_{15}$ClO$_4$Na (M$^+$+Na): 365.0551; found: 365.0551.

Example: 76

Ethyl 3-(2-benzoyl-5-chlorobenzofuran-3-yl)propanoate (4eb)

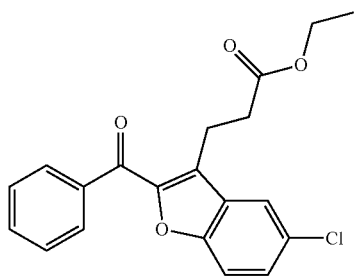 [SMILES: CCOC(=O)CCc1c(C(=O)c2ccccc2)oc2ccc(Cl)cc12]

Isolated by column chromatography (pet.ether/AcOEt=9:1, R$_f$=0.4). The title compound was determined as colourless oil (71%), and the ratio of linear to branch product (93:7); $^1$H NMR (400 MHz, CDCl$_3$): δ 1.22 (t, J=7.2 Hz, 3H), 2.80 (t, J=7.5 Hz, 2H), 3.40 (t, J=7.5 Hz 2H), 4.12 (q, J=7.1 Hz, 2H), 7.44-7.56 (m, 4H), 7.62-7.66 (m, 1H), 7.77 (d, J=1.7 Hz, 1H), 8.09-8.11 (m, 2H); $^{13}$C NMR (100 MHz, CDCl$_3$): δ 14.1 (q), 20.0 (t), 33.8 (t), 60.6 (t), 113.4 (d), 121.2 (d), 128.4 (d, 2C), 128.6 (d), 128.9 (s), 129.3 (s), 129.6 (s), 129.8 (d, 2C), 133.0 (d), 137.2 (s), 149.5 (s), 152.5 (s), 172.6 (s), 185.3 (s) ppm; IR (neat): ν 2983, 2938, 2908, 1732, 1655, 1598, 1560, 1447, 1370, 1263, 1181, 1035, 977, 860, 727 cm$^{-1}$; HRMS (ESI) calcd for C$_{20}$H$_{17}$ClO$_4$Na (M$^+$+Na): 379.0708; found: 379.0709.

Example: 77

Methyl 3-(3-benzoyl-5-methoxybenzofuran-2-yl)propanoate: 7a

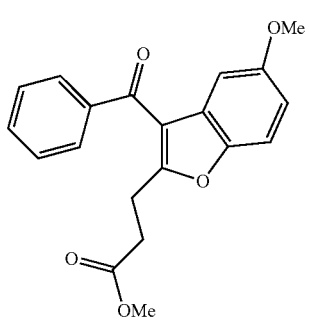 [SMILES: COC(=O)CCc1oc2ccc(OC)cc2c1C(=O)c1ccccc1]

Isolated by column chromatography (pet.ether/AcOEt=9:1, R$_f$=0.4). The title compound was determined as brown oil (71%). $^1$H NMR (400 MHz, CDCl$_3$): δ 2.78 (t, J=7.5 Hz, 2H), 3.19 (t, J=7.4 Hz, 2H), 3.64 (s, 3H), 3.69 (s, 3H), 6.80 (d, J=2.5 Hz, 1H), 6.87 (dd, J=2.6, 8.9 Hz, 1H), 7.35 (d, J=8.9 Hz, 1H), 7.48 (t, J=7.7 Hz, 2H), 7.60 (t, J=7.4 Hz, 1H), 7.82 (d, J=7.5 Hz, 2H); $^{13}$C NMR (100 MHz, CDCl$_3$): δ 23.9 (t), 31.9 (t), 51.9 (q), 55.8 (q), 104.0 (d), 111.5 (d), 113.4 (d), 117.3 (s), 127.3 (s), 128.5 (d, 2C), 129.1 (d, 2C), 132.8 (d), 139.1 (s), 148.7 (s), 156.5 (s), 163.5 (s), 172.3 (s), 191.8 (s).

Example: 78

Ethyl 3-(3-benzoyl-5-methoxybenzofuran-2-yl)propanoate: 7b

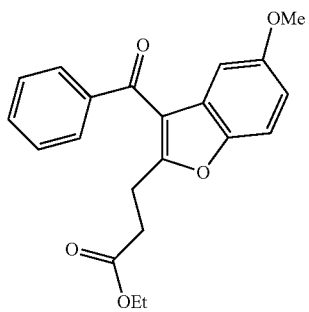 [SMILES: CCOC(=O)CCc1oc2ccc(OC)cc2c1C(=O)c1ccccc1]

Isolated by column chromatography (pet.ether/AcOEt=9:1, R$_f$=0.4). The title compound was determined as light yellow oil (86%). $^1$H NMR (200 MHz, CDCl$_3$): δ 1.20 (t, J=7.1 Hz, 3H), 2.75 (t, J=7.5 Hz, 2H), 3.19 (t, J=7.3 Hz, 2H), 3.69 (s, 3H), 4.10 (q, J=7.1 Hz, 2H), 6.80 (d, J=2.5 Hz, 1H), 6.87 (dd, J=2.6, 8.9 Hz, 1H), 7.34 (d, J=8.9 Hz, 1H), 7.44-7.52 (m, 2H), 7.56-7.64 (m, 1H), 7.79-7.84 (m, 2H); $^{13}$C NMR (50 MHz, CDCl$_3$): δ 14.1 (q), 24.0 (t), 32.1 (t), 55.7 (q), 60.7 (t), 103.9 (d), 111.5 (d), 113.3 (d), 117.3 (s), 127.3 (s), 128.5 (d, 2C), 129.1 (d, 2C), 132.8 (d), 139.1 (s), 148.6 (s), 156.5 (s), 163.7 (s), 171.9 (s), 191.8 (s).

Example: 79

Tert-butyl 3-(3-benzoyl-5-methoxybenzofuran-2-yl)propanoate: 7c

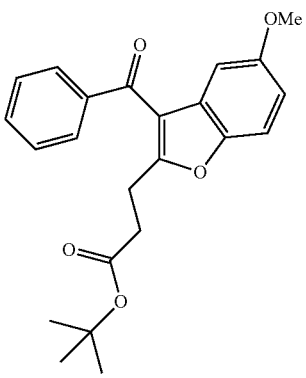 [SMILES: COc1ccc2oc(CCC(=O)OC(C)(C)C)c(C(=O)c3ccccc3)c2c1]

Isolated by column chromatography (pet.ether/AcOEt=9:1, $R_f$=0.4). The title compound was determined as white solid (88%). $^1$H NMR (500 MHz, CDCl$_3$): δ 1.39 (s, 9H), 2.66 (t, J=7.5 Hz, 2H), 3.13 (t, J=7.5 Hz, 2H), 3.69 (s, 3H), 6.83 (d, J=2.3 Hz, 1H), 6.87 (dd, J=2.3, 8.9 Hz, 1H), 7.33 (d, J=8.9 Hz, 1H), 7.48 (t, J=7.6 Hz, 2H), 7.59 (t, J=7.3 Hz, 1H), 7.81 (d, J=7.6 Hz, 2H); $^{13}$C NMR (125 MHz, CDCl$_3$): δ 24.2 (t), 28.0 (q, 3C), 33.3 (t), 55.7 (q), 80.7 (s), 103.9 (d), 111.5 (d), 113.3 (d), 117.1 (s), 127.3 (s), 128.5 (d, 2C), 129.1 (d, 2C), 132.7 (d), 139.2 (s), 148.6 (s), 156.4 (s), 164.1 (s), 171.1 (s), 191.8 (s).

Example: 80

Methyl 3-(3-benzoyl-5-methoxybenzofuran-2-yl)-2-methylpropanoate: 7d

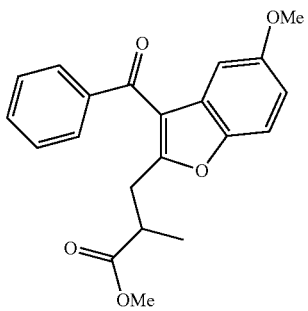 [SMILES: COC(=O)C(C)Cc1oc2ccc(OC)cc2c1C(=O)c1ccccc1]

Isolated by column chromatography (pet.ether/AcOEt=9:1, $R_f$=0.4). The title compound was determined as Light Yellow oil (72%). $^1$H NMR (500 MHz, CDCl$_3$): δ 1.17 (d, J=6.7 Hz, 3H), 2.99-3.05 (m, 2H), 3.25-3.30 (m, 1H), 3.62 (s, 3H), 3.68 (s, 3H), 6.74 (d, J=2.4 Hz, 1H), 6.87 (dd, J=8.8, 2.5 Hz, 1H), 7.34 (d, J=8.9 Hz, 1H), 7.48 (t, J=7.6 Hz, 2H), 7.60 (t, J=7.4 Hz, 1H), 7.81 (d, J=7.3 Hz, 2H); $^{13}$C NMR (125 MHz, CDCl$_3$): δ 16.9 (q), 31.8 (t), 38.5 (d), 51.9 (q), 55.8 (q), 104.0 (d), 111.6 (d), 113.4 (d), 118.0 (s), 127.3 (s), 128.5 (d, 2C), 129.2 (d, 2C), 132.8 (d), 139.0 (s), 148.7 (s), 156.4 (s), 162.9 (s), 175.4 (s), 191.8 (s).

Example: 81

Cyclohexyl 3-(3-benzoyl-5-methoxybenzofuran-2-yl)propanoate: 7e

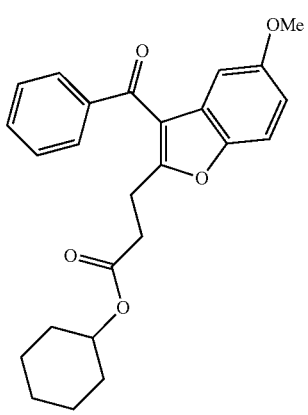 [SMILES: COc1ccc2oc(CCC(=O)OC3CCCCC3)c(C(=O)c3ccccc3)c2c1]

Isolated by column chromatography (pet.ether/AcOEt=9:1, $R_f$=0.4). The title compound was determined as Yellow oil (91%). $^1$H NMR (400 MHz, CDCl$_3$): δ 1.32-1.37 (m, 4H), 1.48-1.52 (m, 2H), 1.64-1.67 (m, 3H), 1.76-1.79 (m, 2H), 2.74 (t, J=7.4 Hz, 2H), 3.17 (t, J=7.4 Hz, 2H), 3.69 (s, 3H), 4.70-4.75 (m, 1H), 6.82 (d, J=2.2 Hz, 3H), 6.86 (dd, J=8.9, 2.6 Hz, 1H), 7.33 (d, J=8.9 Hz, 1H), 7.48 (t, J=7.6 Hz, 2H), 7.59 (t, J=7.3 Hz, 1H), 7.80-7.82 (m, 2H); $^{13}$C NMR (100 MHz, CDCl$_3$): δ 23.6 (t, 2C), 24.1 (t), 25.3 (t), 31.5 (t, 2C), 32.4 (t), 55.7 (q), 72.9 (d), 104.0 (d), 111.5 (d), 113.3 (d), 117.2 (s), 127.3 (s), 128.5 (d, 2C), 129.1 (d, 2C), 132.7 (d), 139.2 (s), 148.6 (s), 156.5 (s), 163.9 (s), 171.3 (s), 391.8 (s).

Example: 82

Methyl 2-(3-benzoyl-5-methoxybenzofuran-2-yl)butanoate: 7f

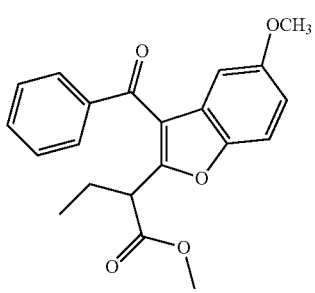 [SMILES: CCC(C(=O)OC)c1oc2ccc(OC)cc2c1C(=O)c1ccccc1]

Isolated by column chromatography (pet.ether/AcOEt=9:1, $R_f$=0.5). The title compound was determined as light brown oil (80%). $^1$H NMR (500 MHz, CDCl$_3$): δ 0.89 (t, J=7.5 Hz, 3H), 2.02-2.11 (m, 1H), 2.14-2.22 (m, 1H), 3.68 (s, 3H), 3.68 (s, 3H), 4.11 (dd, J=8.8, 6.4 Hz, 1H), 6.75 (d, J=2.1 Hz, 1H), 6.90 (dd, J=9.2, 2.4 Hz, 1H), 7.40 (d, J=8.9 Hz, 1H), 7.48 (t, J=7.6 Hz, 2H), 7.61 (t, J=7.3 Hz, 1H), 7.83 (d, J=7.3 Hz, 2H); $^{13}$C NMR (125 MHz, CDCl$_3$): δ 11.9 (q), 23.7 (t), 46.0 (d), 52.4 (q), 55.8 (q), 104.0 (d), 112.0 (d), 113.8 (d), 118.9 (s), 126.9 (s), 128.5 (d, 2C), 129.2 (d, 2C), 132.9 (d), 138.9 (s), 148.9 (s), 156.5 (s), 160.6 (s), 171.0 (s), 191.6 (s).

Example: 83

Methyl 4-(3-benzoyl-5-methoxybenzofuran-2-yl)butanoate: 7g

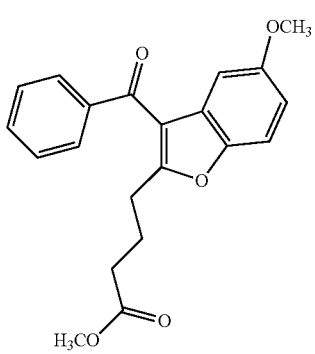 [SMILES: COC(=O)CCCc1oc2ccc(OC)cc2c1C(=O)c1ccccc1]

Isolated by column chromatography (pet.ether/AcOEt=9: 1, $R_f$=0.4). The title compound was determined as light yellow oil. $^1$H NMR (500 MHz, CDCl$_3$): δ 2.08 (quin, J=7.5 Hz, 2H), 2.34 (t, J=7.5 Hz, 2H), 2.91 (t, J=7.3 Hz, 2H), 3.61 (s, 3H), 3.69 (s, 3H), 6.80 (d, J=2.2 Hz, 1H), 6.87 (dd, J=2.4, 8.9 Hz, 1H), 7.35 (d, J=8.9 Hz, 1H), 7.48 (t, J=7.5 Hz, 2H), 7.59 (t, J=7.5 Hz, 1H), 7.80 (d, J=7.3 Hz, 2H); $^{13}$C NMR (125 MHz, CDCl$_3$): δ 23.2 (t), 27.6 (t), 33.2 (t), 51.6 (q), 55.8 (q), 104.0 (d), 111.5 (d), 113.3 (d), 117.4 (s), 127.3 (s), 128.5 (d, 2C), 129.1 (d, 2C), 132.7 (d), 139.2 (s), 148.7 (s), 156.5 (s), 164.9 (s), 173.3 (s), 191.9 (s).

Example: 84

2-(3-benzoyl-5-methoxybenzofuran-2-yl)-N-isopropylpropanamide: 7h

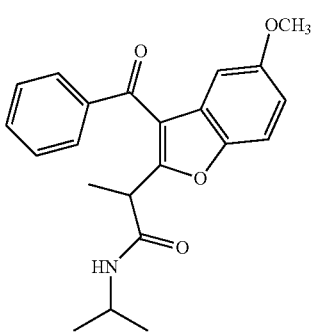 [SMILES: COc1ccc2oc(C(C)C(=O)NC(C)C)c(C(=O)c3ccccc3)c2c1]

Isolated by column chromatography (pet.ether/AcOEt=8: 2, $R_f$=0.5). The title compound was determined as White solid (82%). $^1$H NMR (500 MHz, CDCl$_3$): δ 1.01 (d, J=6.7 Hz, 3H), 1.20 (d, J=6.7 Hz, 3H), 1.60 (d, J=7.0 Hz, 3H), 3.61 (s, 3H), 3.99 (dq, J=6.7, 13.4 Hz, 1H), 4.16 (d, J=7.0 Hz, 1H), 6.45 (d, J=2.4 Hz, 1H), 6.88 (dd, J=2.4, 8.9 Hz, 1H), 7.41 (d, J=9.2 Hz, 1H), 7.44 (d, J=7.3 Hz, 1H), 7.51 (t, J=7.6 Hz, 2H), 7.65 (t, J=7.5 Hz, 1H), 7.89 (d, J=7.3 Hz, 2H); $^{13}$C NMR (125 MHz, CDCl$_3$): δ 13.5 (q), 22.4 (q), 22.7 (q), 39.6 (d), 41.7 (d), 55.7 (q), 104.2 (d), 112.3 (d), 113.3 (d), 117.0 (s), 126.5 (s), 128.6 (d, 2C), 129.7 (d, 2C), 133.6 (d), 138.1 (s), 148.7 (s), 156.3 (s), 164.6 (s), 168.6 (s), 192.6 (s).

Example: 85

3-(3-benzoyl-5-methoxybenzofuran-2-yl)-N-isopropylpropanamide: 7i

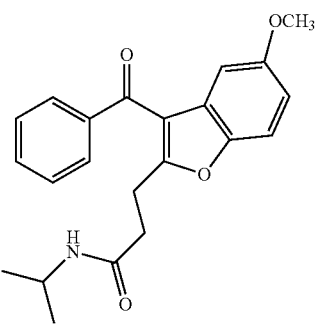 [SMILES: COc1ccc2oc(CCC(=O)NC(C)C)c(C(=O)c3ccccc3)c2c1]

Isolated by column chromatography (pet.ether/AcOEt=7: 3, $R_f$=0.2). The title compound was determined as yellow oil, $^1$H NMR (500 MHz, CDCl$_3$): δ 1.07 (d, J=6.6 Hz, 6H), 2.63 (t, J=7.5 Hz, 2H), 3.21 (t, J=7.4 Hz, 2H), 3.67 (s, 3H), 3.97-4.09 (m, 1H), 6.71 (d, J=2.5 Hz, 1H), 6.86 (dd, J=9.0, 2.5 Hz, 1H), 7.34 (d, J=9.0 Hz, 1H), 7.41-7.53 (m, 2H), 7.57-7.65 (m, 1H), 7.79-7.84 (m, 2H).

Example: 86

Tert-butyl 3-(5-methoxy-3-(4-methoxybenzoyl)benzofuran-2-yl)propanoate: 7j

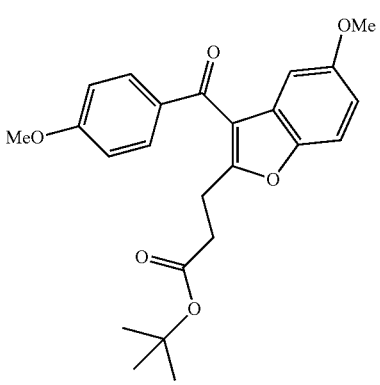 [SMILES: COc1ccc(C(=O)c2c(CCC(=O)OC(C)(C)C)oc3ccc(OC)cc23)cc1]

Isolated by column chromatography (pet.ether/AcOEt=9: 1, $R_f$=0.5). The title compound was determined as brown solid (87%). $^1$H NMR (400 MHz, CDCl$_3$): δ 1.39 (s, 9H), 2.67 (t, J=7.5 Hz, 2H), 3.14 (t, J=7.5 Hz, 2H), 3.72 (s, 3H), 3.88 (s, 3H), 6.85-6.87 (m, 2H), 6.95 (d, J=8.8 Hz, 2H), 7.33 (d, J=9.5 Hz, 1H), 7.84 (d, J=8.6 Hz, 2H); $^{13}$C NMR (100 MHz, CDCl$_3$): δ 24.1 (t), 28.0 (q, 3C), 33.4 (t), 55.5 (q), 55.8 (q), 80.7 (s), 103.9 (d), 111.4 (d), 113.1 (d), 113.7 (d, 2C), 117.3 (s), 127.6 (s), 131.6 (s), 131.7 (d, 2C), 148.6 (s), 156.4 (s), 163.0 (s), 163.5 (s), 171.2 (s), 190.3 (s).

Example: 87

Methyl 3-(5-methoxy-3-(4-methoxybenzoyl)benzofuran-2-yl)-2-methylpropanoate: 7k

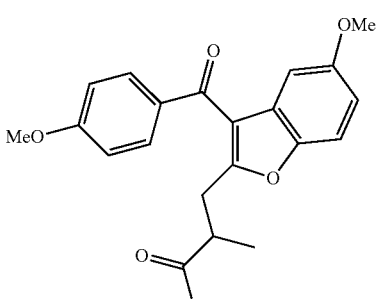

Isolated by column chromatography (pet.ether/AcOEt=9: 1. $R_f$=0.4). The title compound was determined as colourless oil (62%). $^1$H NMR (500 MHz, CDCl$_3$): δ 1.17 (d, J=6.7 Hz, 3H), 2.99-3.05 (m, 2H), 3.25-3.32 (m, 1H), 3.61 (s, 3H), 3.71 (8, 3H), 3.89 (s, 3H), 6.80 (d, J=2.1 Hz 1H), 6.87 (dd, J=2.4, 8.9 Hz, 1H), 6.96 (d, J=8.9 Hz, 2H), 7.34 (d, J=8.9

Hz, 1H), 7.84 (d, J=8.5 Hz, 2H); $^{13}$C NMR (125 MHz, CDCl$_3$): δ 16.9 (q), 31.7 (t), 38.5 (d), 51.9 (q), 55.5 (q), 55.9 (q), 104.0 (d), 111.5 (d), 113.2 (d), 113.7 (d, 2C), 118.2 (s), 127.5 (s), 131.5 (s), 131.8 (d, 2C), 148.7 (s), 156.4 (s), 161.8 (s), 163.6 (s), 175.5 (s), 190.2 (s).

Example: 88

Methyl 2-(5-methoxy-3-(4-methoxybenzoyl)benzofuran-2-yl)butanoate: 8a

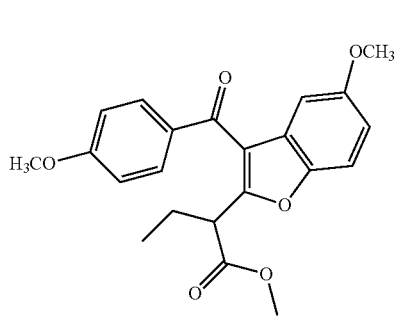 [SMILES: CCC(C(=O)OC)c1oc2ccc(OC)cc2c1C(=O)c1ccc(OC)cc1]

Isolated by column chromatography (pet.ether/AcOEt=9:1, R$_f$=0.6). The title compound was determined as colourless oil (77%). $^1$H NMR (500 MHz, CDCl$_3$): δ 0.89 (t, J=7.5 Hz, 3H), 2.00-2.11 (m, 1H), 2.12-2.23 (m, 1H), 3.68 (s, 3H), 3.71 (s, 3H), 3.89 (s, 3H), 4.10 (dd, J=6.4, 8.9 Hz, 1H), 6.81 (d, J=2.8 Hz, 1H), 6.90 (dd, J=9.0, 2.8 Hz, 1H), 6.94-6.96 (m, 2H), 7.40 (d, J=8.8 Hz, 1H), 7.85-7.88 (m, 2H); $^{13}$C NMR (125 MHz, CDCl$_3$): δ 11.9 (q), 23.8 (t), 45.9 (d), 52.4 (q), 55.5 (q), 55.9 (q), 104.0 (d), 111.9 (d), 113.6 (d), 113.7 (d, 2C), 119.1 (s), 127.2 (s), 131.4 (s), 131.8 (d, 2C), 148.9 (s), 156.4 (s), 159.6 (s), 163.7 (s), 171.2 (s), 190.0 (s).

Example: 90

Methyl 4-(5-methoxy-3-(4-methoxybenzoyl)benzofuran-2-yl)butanoate: 7l

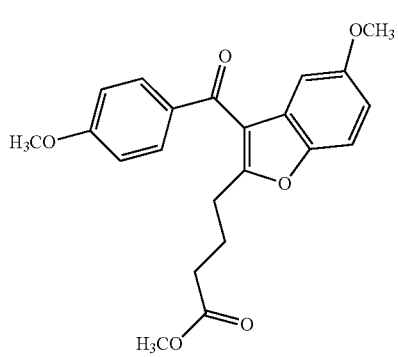 [SMILES: COC(=O)CCCc1oc2ccc(OC)cc2c1C(=O)c1ccc(OC)cc1]

Isolated by column chromatography (pet.ether/AcOEt=9:1, R$_f$=0.5). The title compound was determined as colourless oil. $^1$H NMR (500 MHz, CDCl$_3$): δ 2.09 (quin, J=7.5 Hz, 2H), 2.35 (t, J=7.4 Hz, 2H), 2.92 (t, J=7.3 Hz, 2H), 3.60 (s, 3H), 3.72 (s, 3H), 3.89 (s, 3H), 6.84 (d, J=2.1 Hz, 1H), 6.87 (dd, J=8.9, 2.4 Hz, 1H), 6.95 (d, J=8.9 Hz, 2H), 7.35 (d, J=8.9 Hz, 1H), 7.83 (d, J=8.9 Hz, 2H); $^{13}$C NMR (125 MHz, CDCl$_3$): δ 23.2 (t), 27.4 (t), 33.2 (t), 51.6 (q), 55.5 (q), 55.9 (q), 104.0 (d), 111.5 (d), 113.0 (d), 113.7 (d, 2C), 117.5 (s), 127.6 (s), 131.6 (s), 131.7 (d, 2C), 148.7 (s), 156.4 (s), 163.5 (s), 163.8 (s), 173.4 (s), 190.3 (s).

Example: 91

N-isopropyl-2-(5-methoxy-3-(4-methoxybenzoyl)benzofuran-2-yl)propanamide: 8e

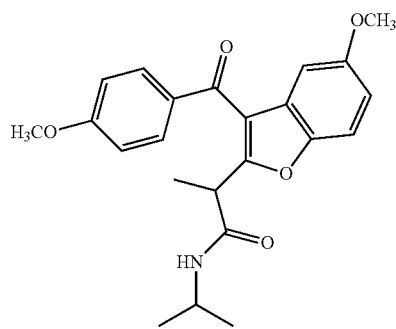 [SMILES: COc1ccc(C(=O)c2c(C(C)C(=O)NC(C)C)oc3ccc(OC)cc23)cc1]

Isolated by column chromatography (pet.ether/AcOEt=8:2, R$_f$=0.5). The title compound was determined as colourless oil (85%). $^1$H NMR (100 MHz, CDCl$_3$): δ 0.99 (d, J=6.9 Hz, 3H), 1.19 (d, J=6.4 Hz, 3H), 1.58 (d, J=7.3 Hz, 3H), 3.66 (s, 3H), 3.90 (s, 3H), 3.97 (dq, J=6.7, 13.8 Hz, 1H), 4.10 (q, J=7.3 Hz, 1H), 6.58 (d, J=2.7 Hz, 1H), 6.88 (dd, J=2.5, 8.9 Hz, 1H), 6.98 (d, J=9.2 Hz, 2H), 7.40 (d, J=8.7 Hz, 1H), 7.62 (d, J=7.8 Hz, 1H), 7.91 (d, J=8.7 Hz, 2H); $^{13}$C NMR (100 MHz, CDCl$_3$): δ 13.4 (q), 22.4 (q), 22.7 (q), 39.4 (d), 41.7 (d), 55.6 (q), 55.8 (q), 104.3 (d), 112.2 (d), 113.0 (d), 113.8 (d, 2C), 117.2 (s), 126.7 (s), 130.6 (s), 132.4 (d, 2C), 148.7 (s), 156.2 (s), 163.9 (s), 164.1 (s), 168.7 (s), 190.8 (s).

Example: 92

N-isopropyl-3-(5-methoxy-3-(4-methoxybenzoyl)benzofuran-2-yl)propanamide: 8f

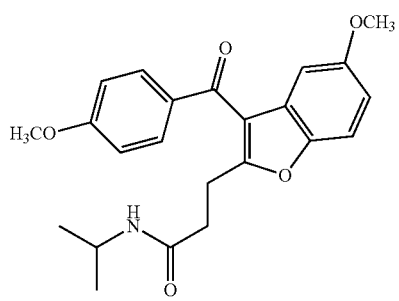 [SMILES: COc1ccc(C(=O)c2c(CCC(=O)NC(C)C)oc3ccc(OC)cc23)cc1]

Isolated by column chromatography (pet.ether/AcOEt=7:3, R$_f$=0.2). The title compound was determined as Light brown solid. $^1$H NMR (500 MHz, CDCl$_3$): δ 1.07 (d, J=6.7 Hz, 6H), 2.67 (t, J=7.2 Hz, 2H), 3.21 (t, J=7.2 Hz, 2H), 3.69 (s, 3H), 3.88 (s, 3H), 3.96-4.06 (m, 1H), 6.19 (d, J=5.6 Hz, 1H), 6.76 (d, J=2.4 Hz, 1H), 6.86 (dd, J=8.9, 2.4 Hz, 1H), 6.96 (d, J=8.9 Hz, 2H), 7.33 (d, J=9.2 Hz, 1H), 7.85 (d, J=8.9 Hz, 2H); $^{13}$C NMR (125 MHz, CDCl$_3$): δ 22.5 (q, 2C), 24.1 (t), 34.5 (t), 41.5 (d), 55.5 (q), 55.8 (q), 104.0 (d), 111.6 (d), 113.0 (d), 113.7 (d, 2C), 117.3 (s), 127.3 (s), 131.2 (s), 131.9 (d, 2C), 148.6 (s), 156.3 (s), 163.3 (s), 163.8 (s), 170.1 (s), 190.5 (s).

Example: 93

Tert-butyl 3-(3-(4-bromobenzoyl)-5-methoxybenzofuran-2-yl)propanoate: 7m

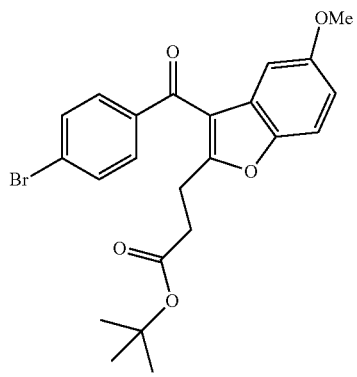 [SMILES: COc1ccc2oc(CCC(=O)OC(C)(C)C)c(C(=O)c3ccc(Br)cc3)c2c1]

Isolated by column chromatography (pet.ether/AcOEt=9:1, R$_f$=0.4). The title compound was determined as white solid (77%). $^1$H NMR (500 MHz, CDCl$_3$): δ 1.39 (s, 9H), 2.67 (t, J=7.5 Hz, 2H), 3.13 (t, J=7.5 Hz, 2H), 3.72 (s, 3H), 6.81 (d, J=2.4 Hz, 1H), 6.87 (dd, J=2.4, 8.9 Hz, 1H), 7.34 (d, J=8.9 Hz, 1H), 7.62 (d, J=8.5 Hz, 2H), 7.69 (d, J=8.5 Hz, 2H); $^{13}$C NMR (125 MHz, CDCl3): δ 24.2 (t), 28.0 (q, 3C), 33.2 (t), 55.8 (q), 80.8 (s), 104.0 (d), 111.6 (d), 113.2 (d), 116.8 (s), 127.1 (s), 127.8 (s), 130.7 (d, 2C), 131.8 (d, 2C), 137.8 (s), 148.6 (s), 156.6 (s), 164.3 (s), 171.0 (s), 190.5 (s).

Example: 94

Methyl 3-(3-(4-bromobenzoyl)-5-methoxybenzofuran-2-yl)-2-methylpropanoate: 7n

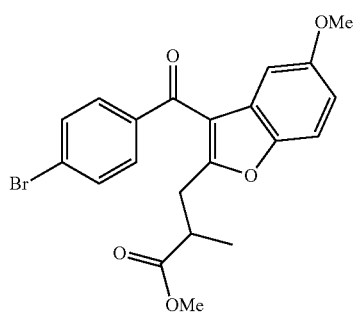 [SMILES: COC(=O)C(C)Cc1oc2ccc(OC)cc2c1C(=O)c1ccc(Br)cc1]

Isolated by column chromatography (pet.ether/AcOEt=9:1, R$_f$=0.4). The title compound was determined as yellow oil (65%). $^1$H NMR (500 MHz, CDCl$_3$): δ 1.18 (d, J=6.7 Hz, 3H), 2.99-3.05 (m, 2H), 3.25-3.30 (m, 1H), 3.61 (s, 3H), 3.70 (s, 3H), 6.73 (d, J=2.4 Hz, 1H), 6.88 (dd, J=2.3, 9.0 Hz, 1H), 7.35 (d, J=8.9 Hz, 1H), 7.62 (d, J=8.3 Hz, 2H), 7.70 (d, J=8.4 Hz, 2H), $^{13}$C NMR (125 MHz, CDCl3): δ 16.9 (q), 31.8 (t), 38.4 (d), 51.9 (q), 55.8 (q), 103.9 (d), 111.7 (d), 113.3 (d), 117.6 (s), 127.0 (s), 127.9 (s), 130.8 (d, 2C), 131.8 (d, 2C), 137.6 (s), 148.7 (s), 156.5 (s), 163.1 (s), 175.3 (s), 190.4 (s).

Example: 95

Methyl 2-(3-benzoyl-5-methoxybenzofuran-2-yl)butanoate: 8b

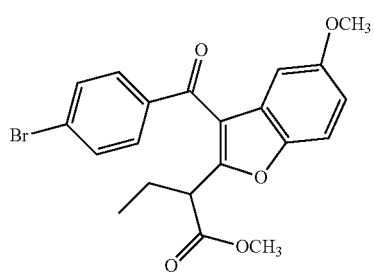 [SMILES: CCC(C(=O)OC)c1oc2ccc(OC)cc2c1C(=O)c1ccc(Br)cc1]

Isolated by column chromatography (pet.ether/AcOEt=9:1, R$_f$=0.5). The title compound was determined as colourless oil (63%). $^1$H NMR (500 MHz, CDCl$_3$): δ 0.89 (t, J=7.5 Hz, 3H), 2.01-2.12 (m, 1H), 2.14-2.24 (m, 1H), 3.68 (s, 3H), 3.71 (s, 3H), 4.10 (dd, J=6.2, 8.9 Hz, 1H), 6.73 (d, J=2.4 Hz, 1H), 6.91 (dd, J=2.7, 9.0 Hz, 1H), 7.41 (d, J=9.0 Hz, 1H), 7.63 (d, J=8.5 Hz, 2H), 7.72 (d, J=8.5 Hz, 2H); $^{13}$C NMR (125 MHz, CDCl3): δ 11.9 (q), 23.7 (t), 46.0 (d), 52.5 (q), 55.9 (q), 104.0 (d), 112.1 (d), 113.7 (d), 118.6 (s), 126.7 (s), 128.1 (s), 130.8 (d, 2C), 131.9 (d, 2C), 137.5 (s), 148.9 (s), 156.6 (s), 160.8 (s), 170.9 (s), 190.4 (s).

Example: 96

Methyl 4-(3-(4-bromobenzoyl)-5-methoxybenzofuran-2-yl)butanoate: 7o

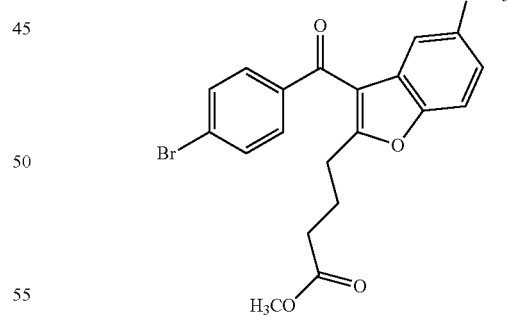

Isolated by column chromatography (pet.ether/AcOEt=9:1, R$_f$=0.4). The title compound was determined as colourless oil. $^1$H NMR (500 MHz, CDCl$_3$): δ 2.09 (quin, J=7.3 Hz, 2H), 2.35 (t, J=7.3 Hz, 2H), 2.92 (t, J=7.3 Hz, 2H), 3.61 (s, 3H), 3.72 (s, 3H), 6.77 (d, J=2.7 Hz, 1H), 6.88 (dd, J=2.5, 8.9 Hz, 1H), 7.36 (d, J=9.2 Hz, 1H), 7.62-7.64 (m, 2H), 7.67-7.70 (m, 2H); $^{13}$C NMR (125 MHz, CDCl3): δ 23.2 (t), 27.6 (t), 29.7 (t), 51.6 (q), 55.9 (q), 104.0 (d), 111.6 (d), 113.2 (d), 127.1 (s), 130.7 (d, 2C), 131.9 (d, 2C), 148.7 (s), 156.6 (s), 165.1 (s), 173.3 (s), 190.6 (s).

Example: 97

2-(3-(4-bromobenzoyl)-5-methoxybenzofuran-2-yl)-N-isopropylpropanamide: 8g

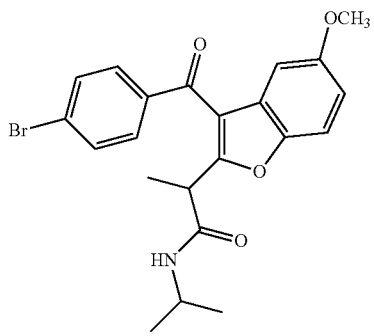 [SMILES: COc1ccc2oc(C(C)C(=O)NC(C)C)c(C(=O)c3ccc(Br)cc3)c2c1]

Isolated by column chromatography (pet.ether/AcOEt=8:2, $R_f$=0.5). The title compound was determined as grey solid (73%). $^1$H NMR (400 MHz, CDCl$_3$): δ 1.02 (d, J=6.4 Hz, 3H), 1.21 (d, J=6.4 Hz, 3H), 1.61 (d, J=7.1 Hz, 3H), 3.68 (s, 3H), 4.00 (dq, J=6.7, 13.8 Hz, 1H), 4.14 (q, J=6.9 Hz, 1H), 6.49 (d, J=2.7 Hz, 1H), 6.92 (dd, J=2.5, 8.9 Hz, 1H), 7.38 (d, J=7.3 Hz, 1H), 7.44 (d, J=9.2 Hz, 1H), 7.66-7.69 (m, 2H), 7.78-7.81 (m, 2H); $^{13}$C NMR (100 MHz, CDCl3): δ 13.6 (q), 22.4 (q), 22.7 (q), 39.6 (d), 41.7 (d), 55.8 (q), 104.2 (d), 112.4 (d), 113.1 (d), 116.6 (s), 126.2 (s), 128.8 (s), 131.3 (d, 2C), 131.9 (d, 2C), 136.7 (s), 148.7 (s), 156.4 (s), 164.8 (s), 168.5 (s), 191.3 (s).

Example: 98

3-(3-(4-bromobenzoyl)-5-methoxybenzofuran-2-yl)-N-isopropylpropanamide: 8h

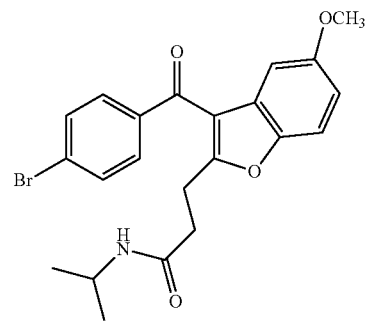 [SMILES: COc1ccc2oc(CCC(=O)NC(C)C)c(C(=O)c3ccc(Br)cc3)c2c1]

Isolated by column chromatography (pet.ether/AcOEt=7:3, $R_f$=0.2). The title compound was determined as colourless solid. $^1$H NMR (500 MHz, CDCl$_3$): δ 1.08 (d, J=6.4 Hz, 6H), 2.64 (t, J=7.1 Hz, 2H), 3.21 (t, J=6.9 Hz, 2H), 3.70 (s, 3H), 3.99-4.08 (m, 1H), 5.82 (d, J=6.5 Hz, 1H), 6.71 (d, J=2.7 Hz, 1H), 6.88 (dd, J=8.9, 2.5 Hz, 1H), 7.35 (d, J=8.7 Hz, 1H), 7.62-7.65 (m, 2H), 7.69-7.72 (m, 2H); $^{13}$C NMR (125 MHz, CDCl3): δ 22.6 (q, 2C), 24.4 (t), 34.4 (t), 41.5 (d), 55.8 (q), 104.0 (d), 111.7 (d), 113.2 (d), 116.8 (s), 126.9 (s), 128.1 (s), 130.8 (d, 2C), 131.9 (d, 2C), 137.4 (s), 148.6 (s), 156.5 (s), 164.6 (s), 169.8 (s), 190.8 (s).

Example: 99

Tert-butyl 3-(3-benzoyl-5-methoxynaphtho[1,2-b]furan-2-yl)propanoate: 7p

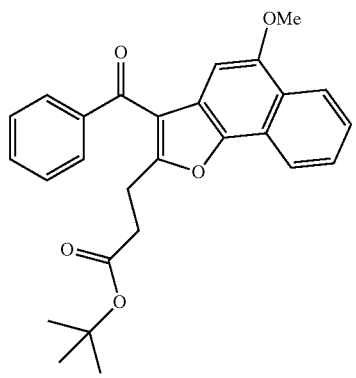 [SMILES: COc1cc2c(C(=O)c3ccccc3)c(CCC(=O)OC(C)(C)C)oc2c2ccccc12]

Isolated by column chromatography (pet.ether/AcOEt=9:1, $R_f$=0.6). The title compound was determined as yellow solid (72%). $^1$H NMR (500 MHz, CDCl$_3$): δ 1.40 (s, 9H), 2.75 (t, J=7.6 Hz, 2H), 3.22 (t, J=7.6 Hz, 2H), 3.84 (s, 3H), 6.74 (s, 1H), 7.48-7.52 (m, 3H), 7.61 (t, J=7.6 Hz, 2H), 7.84-7.87 (m, 2H), 8.20 (d, J=8.1 Hz, 1H), 8.28 (d, J=8.3 Hz, 1H); $^{13}$C NMR (125 MHz, CDCl3): δ 24.3 (t), 28.0 (q, 3C), 33.6 (t), 55.7 (q), 80.7 (s), 96.9 (d), 118.3 (s), 119.6 (d), 121.1 (s), 122.0 (s), 123.1 (d), 123.9 (s), 124.9 (d), 127.2 (d), 128.5 (d, 2C), 129.2 (d, 2C), 132.8 (d), 139.3 (s), 144.1 (s), 152.6 (s), 162.0 (s), 171.2 (s), 192.1 (s).

Example: 100

Methyl 3-(3-benzoyl-5-methoxynaphtho[1,2-b]furan-2-yl)-2-methylpropanoate: 7q

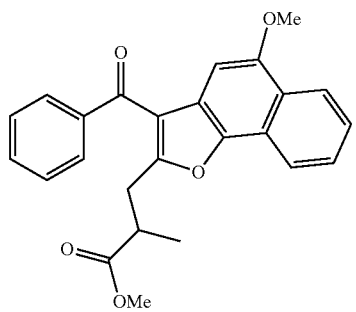 [SMILES: COC(=O)C(C)Cc1oc2c(cc(OC)c3ccccc32)c1C(=O)c1ccccc1]

Isolated by column chromatography (pet.ether/AcOEt=9:1, $R_f$=0.6). The title compound was determined as Brown oil (81%). $^1$H NMR (500 MHz, CDCl$_3$): δ 1.21 (d, J=7.0 Hz, 3H), 3.05-3.15 (m, 2H), 3.36 (dd, J=6.9, 14.5 Hz, 1H), 3.64 (s, 3H), 3.81 (s, 3H), 6.66 (s, 1H), 7.50 (t, J=7.6 Hz, 3H), 7.62 (t, J=7.3 Hz, 2H), 7.86 (d, J=7.3 Hz, 2H), 8.18 (d, J=8.2 Hz, 1H), 8.28 (d, J=8.5 Hz, 1H); $^{13}$C NMR (125 MHz, CDCl3): δ 16.9 (q), 32.0 (t), 38.8 (d), 51.9 (q), 55.7 (q), 96.8 (d), 119.2 (s), 119.6 (d), 121.2 (s), 121.8 (s), 123.1 (d), 124.0 (s), 125.0 (d), 127.3 (d), 128.5 (d, 2C), 129.3 (d, 2C), 132.8 (d), 139.1 (s), 144.2 (s), 152.6 (s), 160.7 (s), 175.5 (s), 192.0 (s).

Example: 101

Methyl 2-(3-benzoyl-5-methoxynaphtho[1,2-b]furan-2-yl)butanoate: 8c

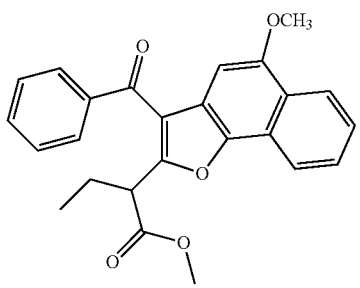 [SMILES: CCC(C(=O)OC)c1oc2c(cc(OC)c3ccccc32)c1C(=O)c1ccccc1]

Isolated by column chromatography (pet.ether/AcOEt=9:1, R$_f$=0.6). The title compound was determined as brown liquid (71%). $^1$H NMR (400 MHz, CDCl$_3$): δ 0.93 (t, J=7.6 Hz, 3H), 2.14-2.20 (m, 1H), 2.22-2.29 (m, 1H), 3.69 (s, 3H), 3.81 (s, 3H), 4.15 (dd, J=6.4, 8.7 Hz, 1H), 6.64 (s, 1H), 7.48-7.53 (m, 3H), 7.63 (t, J=7.3 Hz, 2H), 7.87-7.90 (m, 2H), 8.25 (d, J=8.2 Hz, 1H), 8.28 (d, J=8.2 Hz, 1H); $^{13}$C NMR (125 MHz, CDCl3): δ 12.0 (s), 23.9 (s), 29.7 (s), 46.0 (s), 52.4 (s), 55.7 (s), 77.0 (s), 96.7 (s), 119b.9 (s), 120.1 (s), 121.2 (s), 121.6 (s), 123.0 (s), 124.2 (s), 125.2 (s), 127.3 (s), 128.5 (s), 129.3 (s), 133.0 (s), 139.0 (s), 144.6 (s), 152.6 (s), 158.5 (s), 171.2 (s), 191.9 (s).

Example: 102

2-(3-benzoyl-5-methoxynaphtho[1,2-b]furan-2-yl)-N-isopropylpropanamide: 8i

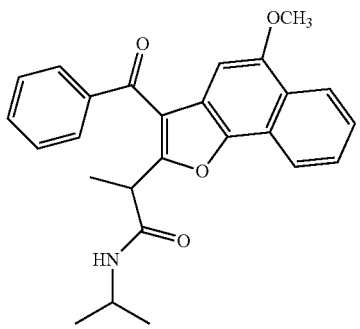 [SMILES: COc1cc2c(C(=O)c3ccccc3)c(C(C)C(=O)NC(C)C)oc2c2ccccc12]

Isolated by column chromatography (pet.ether/AcOEt=8:2, R$_f$=0.5). The title compound was determined as brown solid (82%). $^1$H NMR (200 MHz, CDCl$_3$): δ 1.01 (d, J=6.6 Hz, 3H), 1.21 (d, J=6.6 Hz, 3H), 1.69 (d, J=7.1 Hz, 3H), 3.70 (s, 3H), 3.92-4.09 (m, 1H), 4.21 (q, J=7.1 Hz, 1H), 6.31 (s, 1H), 7.46-7.71 (m, 6H), 7.92-7.96 (m, 2H), 8.27 (t, J=7.3 Hz, 2H); $^{13}$C NMR (125 MHz, CDCl3): δ 13.7 (q), 22.4 (q), 22.7 (q), 39.7 (d), 41.7 (d), 55.5 (q), 96.5 (d), 118.3 (s), 120.1 (d), 120.9 (s), 121.2 (s), 122.9 (d), 124.0 (s), 125.3 (d), 127.4 (d), 128.5 (d, 2C), 129.9 (d, 2C), 133.5 (d), 138.2 (s), 144.3 (s), 152.5 (s), 162.3 (s), 168.9 (s), 192.7 (s).

Example: 103

3-(3-benzoyl-5-methoxynaphtho[1,2-b]furan-2-yl)-N-isopropylpropanamide: 8j

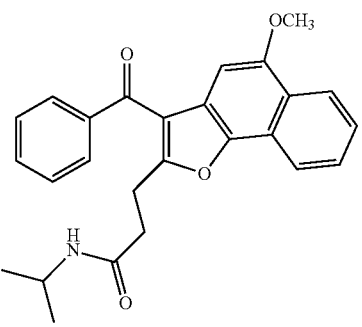 [SMILES: COc1cc2c(C(=O)c3ccccc3)c(CCC(=O)NC(C)C)oc2c2ccccc12]

Isolated by column chromatography (pet.ether/AcOEt=7:3, R$_f$=0.2). The title compound was determined as yellow solid. $^1$H NMR (500 MHz, CDCl$_3$): δ 1.08 (d, J=6.4 Hz, 6H), 2.72 (t, J=6.9 Hz, 2H), 3.31 (t, J=6.7 Hz, 2H), 3.80 (s, 3H), 3.99-4.06 (m, 1H), 5.91 (br. s., 1H), 6.60 (s, 1H), 7.51 (t, J=7.6 Hz, 3H), 7.62 (q, J=7.5 Hz, 2H), 7.88 (d, J=7.3 Hz, 2H), 8.19 (d, J=8.2 Hz, 1H), 8.27 (d, J=8.5 Hz, 1H); $^{13}$C NMR (125 MHz, CDCl3): δ 22.7 (q, 2C), 24.5 (t), 35.0 (t), 41.5 (d), 55.6 (q), 96.7 (d), 118.4 (s), 119.7 (d), 121.1 (s), 121.6 (s), 123.1 (d), 124.0 (s), 125.1 (d), 127.3 (d), 128.6 (d, 2C), 129.4 (d, 2C), 133.0 (d), 139.0 (s), 144.2 (s), 152.6 (s), 162.3 (s), 170.1 (s), 192.3 (s).

Example: 104

Tert-butyl 3-(3-benzoyl-4,6-dibromo-5-methoxybenzofuran-2-yl)propanoate: 7r

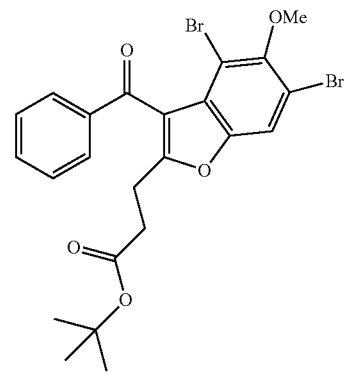 [SMILES: COc1c(Br)cc2oc(CCC(=O)OC(C)(C)C)c(C(=O)c3ccccc3)c2c1Br]

Isolated by column chromatography (pet.ether/AcOEt=9:1, R$_f$=0.5). The title compound was determined as colourless oil (81%). $^1$H NMR (500 MHz, CDCl$_3$): δ 13.9 (s, 9H), 2.60 (t, J=7.5 Hz, 2H), 2.95 (t, J=7.6 Hz, 2H), 3.82 (s, 3H), 7.45 (t, J=7.8 Hz, 2H), 7.59 (t, J=7.3 Hz, 1H), 7.66 (s, 1H), 7.84 (d. J=7.3 Hz, 2H); $^{13}$C NMR (125 MHz, CDCl3): δ 23.1 (t), 28.0 (q, 3C), 33.1 (t), 60.9 (q), 81.0 (s), 108.7 (s), 114.1 (s), 114.8 (d), 117.9 (s), 128.3 (s), 128.7 (d, 2C), 129.7 (d, 2C), 133.8 (d), 138.7 (s), 150.0 (s), 150.8 (s), 159.8 (s), 170.8 (s), 191.2 (s).

Example: 105

Methyl 3-(3-benzoyl-4,6-dibromo-5-methoxybenzofuran-2-yl)-2-methylpropanoate: 7s

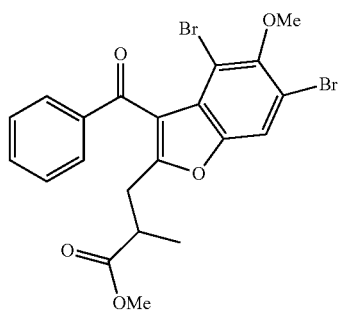 [SMILES: COC(=O)C(C)Cc1oc2cc(Br)c(OC)c(Br)c2c1C(=O)c1ccccc1]

Isolated by column chromatography (pet.ether/AcOEt=9:1, R$_f$=0.5). The title compound was determined as Light yellow oil (68%). ¹H NMR (400 MHz, CDCl₃): δ 1.15 (d, J=6.9 Hz, 3H), 2.77-2.83 (m, 1H), 2.92-2.97 (m, 1H), 3.06-3.12 (m, 1H), 3.58 (s, 3H), 3.82 (s, 3H), 7.45 (t, J=7.7 Hz, 2H), 7.59 (tt, J=1.3, 7.2 Hz, 6H), 7.68 (s, 1H), 7.83 (dd, J=8.2, 1.4 Hz, 2H); ¹³C NMR (100 MHz, CDCl3): δ 16.9 (q), 31.0 (t), 38.2 (d), 51.9 (q), 60.9 (q), 108.7 (s), 114.2 (s), 114.9 (d), 119.0 (s), 128.2 (s), 128.7 (d, 2C), 129.6 (d, 2C), 133.8 (d), 138.7 (s), 150.1 (s), 150.8 (s), 158.8 (s), 175.0 (s), 191.0 (s).

Example: 106

Methyl 2-(3-benzoyl-4,6-dibromo-5-methoxybenzofuran-2-yl)butanoate: 8d

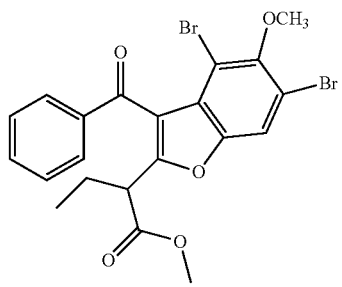 [SMILES: CCC(C(=O)OC)c1oc2cc(Br)c(OC)c(Br)c2c1C(=O)c1ccccc1]

Isolated by column chromatography (pet.ether/AcOEt=9:1, R$_f$=0.5). The title compound was determined as colourless oil (62%). ¹H NMR (500 MHz, CDCl₃): δ 0.88 (t, J=7.3 Hz, 3H), 2.01-2.05 (m, 1H), 2.10-2.15 (m, 1H), 3.58 (s, 3H), 3.67-3.70 (m, 1H), 3.82 (s, 3H), 7.45 (t, J=7.6 Hz, 2H), 7.60 (t, J=7.3 Hz, 1H), 7.74 (s, 1H), 7.85 (d, J=7.9 Hz, 2H); ¹³C NMR (125 MHz, CDCl3) δ 11.9 (q), 23.3 (t), 45.8 (d), 52.4 (q), 61.0 (q), 108.9 (s), 114.7 (s), 115.3 (d), 120.0 (s), 128.0 (s), 128.7 (d, 2C), 129.7 (d, 2C), 133.9 (d), 138.6 (s), 150.2 (s), 151.0 (s), 156.4 (s), 170.4 (s), 191.0 (s).

Example: 107

2-(3-benzoyl-5-methoxybenzofuran-2-yl)-N-isopropylpropanamide: 8k

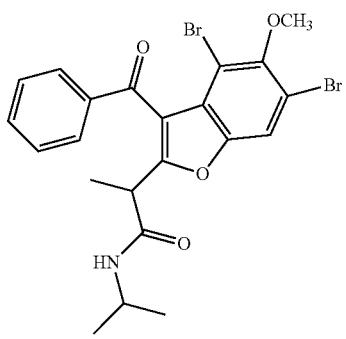 [SMILES: COc1c(Br)cc2oc(C(C)C(=O)NC(C)C)c(C(=O)c3ccccc3)c2c1Br]

Isolated by column chromatography (pet.ether/AcOEt=8:2, R$_f$=0.4). The title compound was determined as colourless oil (65%). ¹H NMR (500 MHz, CDCl₃): δ 1.03 (d, J=6.7 Hz, 3H), 1.17 (d, J=6.4 Hz, 3H), 1.52 (d, J=7.0 Hz, 3H), 3.70 (q, J=7.0 Hz, 1H), 3.82 (s, 3H), 3.96 (dq, J=13.4, 6.6 Hz, 1H), 6.79 (d, J=6.1 Hz, 1H), 7.46 (t, J=7.6 Hz, 2H), 7.62 (t, J=7.5 Hz, 1H), 7.74 (s, 1H), 7.83 (d, J=7.6 Hz, 2H); ¹³C NMR (125 MHz, CDCl3) δ 13.8 (q), 22.4 (q), 22.6 (q), 39.5 (d), 42.0 (d), 61.0 (q), 108.8 (s), 114.8 (s), 115.5 (d), 118.3 (s), 127.6 (s), 128.8 (d, 2C), 129.7 (d, 2C), 134.2 (d), 138.8 (s), 150.0 (s), 151.1 (s), 160.9 (s), 167.8 (s), 192.4 (s).

Example: 108

3-(3-benzoyl-4,6-dibromo-5-methoxybenzofuran-2-yl)-N-isopropylpropanamide: 8l

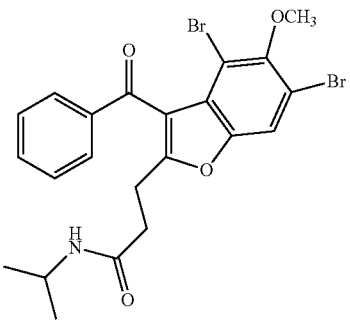 [SMILES: COc1c(Br)cc2oc(CCC(=O)NC(C)C)c(C(=O)c3ccccc3)c2c1Br]

Isolated by column chromatography (pet.ether/AcOEt=7:3, R$_f$=0.2). The title compound was determined as colourless oil. ¹H NMR (400 MHz, CDCl₃): δ 1.08 (d, J=6.6 Hz, 6H), 2.52 (t, J=7.5 Hz, 2H), 3.02 (t, J=7.6 Hz, 2H), 3.82 (s, 3H), 4.01 (dq, J=6.6, 13.1 Hz, 1H), 5.48 (br. s., 1H), 7.45 (t, J=7.7 Hz, 2H), 7.58-7.62 (m, 1H), 7.67 (s, 1H), 7.84 (m, J=7.6 Hz, 2H); ¹³C NMR (100 MHz, CDCl3) δ 22.7 (q, 2C), 23.6 (t), 34.4 (t), 41.5 (d), 61.0 (q), 108.6 (s), 114.2 (s), 114.9 (d), 118.0 (s), 128.3 (s), 128.8 (d, 2C), 129.7 (d, 2C), 134.0 (d), 138.6 (s), 150.0 (s), 150.9 (s), 160.2 (s), 169.4 (s), 191.6 (s).

We claim:

1. A process for synthesis of an alkylated aroyl benzofuran having anti-inflammatory activity which comprises, catalyzing an aroylbenzofuran of formula-I with an alpha, beta unsaturated ester of formula-II in the presence of a ruthenium catalyst, a base, an additive and an organic solvent to produce a compound of formula-III or a compound of formula-IV or mixture thereof;

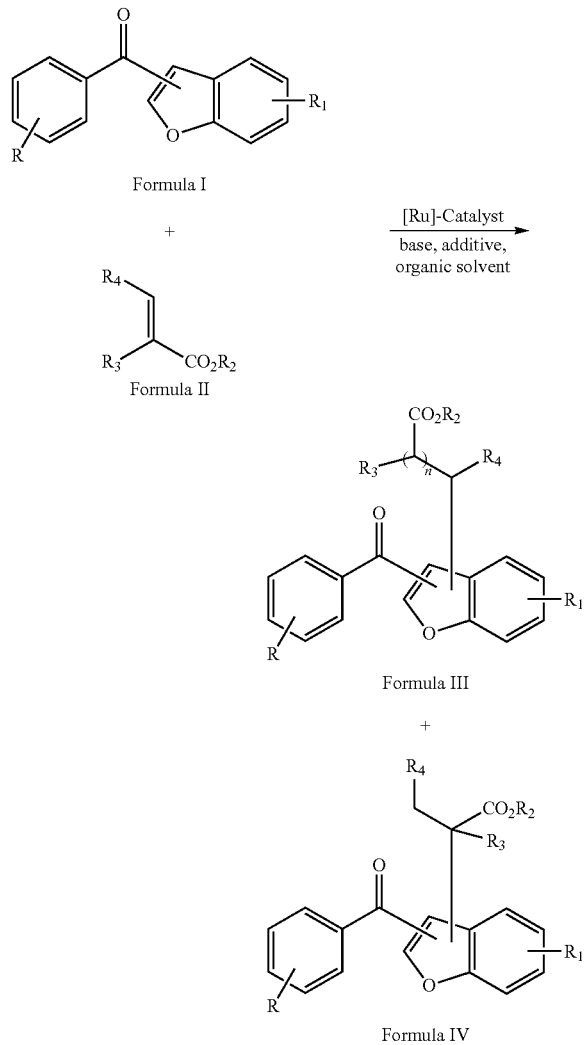

wherein n is an integer ranging from 1 to 6;

R and $R_1$ are independently selected from the group consisting of hydrogen, halogen, $(C_1-C_6)$ alkyl, $(C_1-C_5)$ alkoxy, $COR_5$, wherein $R_5$ is $(C_1-C_6)$ alkyl, aryl or alkylaryl;

$R_2$ is hydrogen, halogen, linear or branched $(C_1-C_6)$ alkyl, $(C_1-C_5)$ alkoxy, or cyclo $(C_4-C_8)$ alkyl $R_3$ is hydrogen, $(C_1-C_6)$ alkyl; and $R_4$ is hydrogen, $(C_1-C_6)$ alkyl, halogen, cycloalkyl, aryl, or alkylaryl.

2. The process according to claim 1, wherein the ruthenium catalyst is selected from the group consisting of $Ru_3(CO)_{12}$, $RuH_2(CO)(PPh_3)_3$, $Ru(PPh_3)_3Cl_2$, and $[Ru(p\text{-}cymene)Cl_2]_2(PPh_3)$.

3. The process according to claim 1, wherein the ruthenium catalyst is $Ru(PPh_3)_3Cl_2$ or $[Ru(p\text{-}cymene)Cl_2]_2$.

4. The process according to claim 1, wherein the base is $K_2CO_3$ or $NaHCO_3$.

5. The process according to claim 1, wherein the additive is selected from the group consisting of adamantane-1-carboxylic acid ($AdCO_2H$), $PivCO_2H$, $CCl_3CO_2H$, $Cu(OAc)_2$, $MesCO_2H$, and silver acetate $Ag(OAc)$.

6. The process according to claim 1, wherein the additive is silver acetate.

7. The process according to claim 1, comprising carrying out said process at a temperature from 130°-150° C.

8. The process according to claim 1, wherein the alpha beta unsaturated ester is an acrylate of formula;

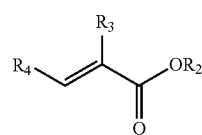

wherein $R_2$ is hydrogen, halogen, linear or branched $(C_1-C_6)$ alkyl, $(C_1-C_5)$ alkoxy or cyclo $(C_4-C_8)$alkyl;

$R_3$ is hydrogen or $(C_1-C_6)$ alkyl; and $R_4$ is hydrogen, $(C_1-C_6)$ alkyl, halogen, cycloalkyl, aryl or alkylaryl.

9. The process according to claim 8, wherein said acrylate is selected from the group consisting of a linear or branched $(C_1-C_6)$alkyl acrylate, a cyclo $(C_4-C_8)$alkyl acrylate, a $(C_1-C_6)$alkyl methacrylate, a $(C_1-C_6)$ alkyl cinnamate, a linear or branched $(C_1-C_6)$ alkyl crotonate, and substituted or unsubstituted acrylamide.

10. The process according to claim 9, wherein said acrylate is selected from the group consisting of methyl acrylate, ethyl acrylate, n-butyl acrylate, terbutyl acrylate, cyclohexyl acrylate, methyl methacrylate, butyl methacrylate, methyl crotonate, ethyl cinnamate, and N-isopropylacrylamide.

11. The process according to claim 1, wherein the aroylbenzofuran of formula-I is selected from the group consisting of 2-aroylbenzofuran and 3-aroylbenzofuran;

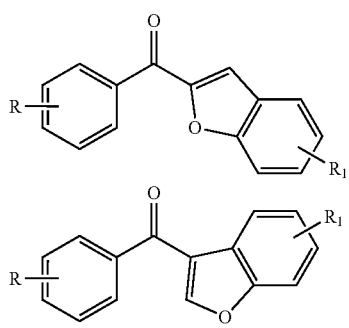

wherein, R and $R_1$ are as above.

12. The process according to claim 1, wherein said process comprises:
 a. adding 2-aroylbenzofuran, acrylate, $K_2CO_3$ and toluene to a reaction vessel containing a mixture of $Ru(PPh_3)_3Cl_2$, $Ag(OAc)$ under argon atmosphere to get a solution mixture;
 b. stirring the solution mixture at a temperature in the range of 130° to 150° C., for a time from 20 to 30 hrs followed by cooling the solution mixture to form a first product, and purifying said first product via column chromatography to obtain a pure benzofuran product of formula IV;

Formula IV

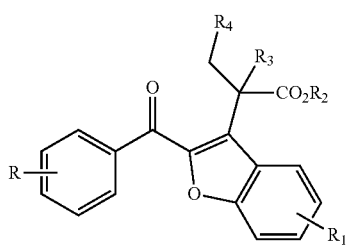

wherein R, $R_1$, $R_2$, $R_3$, and $R_4$ are as above.

13. The process according to claim 12, wherein the branched alkylated benzofuran compound of formula IV is selected from the group consisting of:

methyl 2-(2-benzoylbenzofuran-3-yl)propanoate

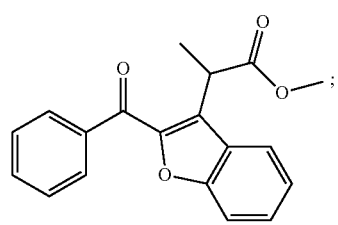 [SMILES: COC(=O)C(C)c1c(C(=O)c2ccccc2)oc2ccccc12]

ethyl 2-(2-benzoylbenzofuran-3-yl)propanoate

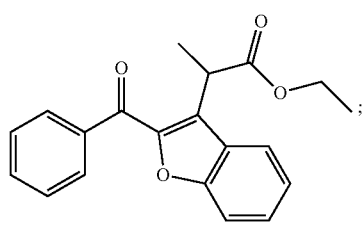 [SMILES: CCOC(=O)C(C)c1c(C(=O)c2ccccc2)oc2ccccc12]

methyl 2-(2-benzoylbenzofuran-3-yl)butanoate

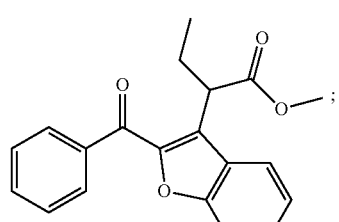

butyl 2-(2-benzoylbenzofuran-3-yl)propanoate

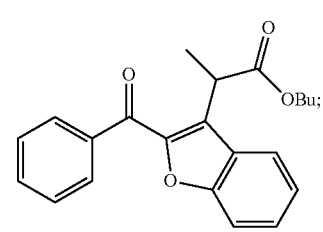

cyclohexyl 2-(2-benzoylbenzofuran-3-yl) propanoate

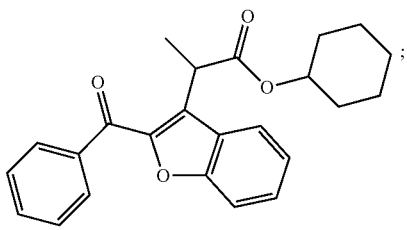 [SMILES: CC(C(=O)OC1CCCCC1)c1c(C(=O)c2ccccc2)oc2ccccc12]

2-(2-benzoylbenzofuran-3-yl)-N isopropylpropanamide

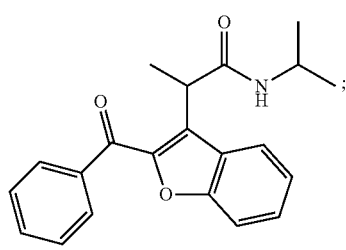 [SMILES: CC(C)NC(=O)C(C)c1c(C(=O)c2ccccc2)oc2ccccc12]

ethyl 2-(2-benzoylbenzofuran-3-yl)-3-phenylpropanoate

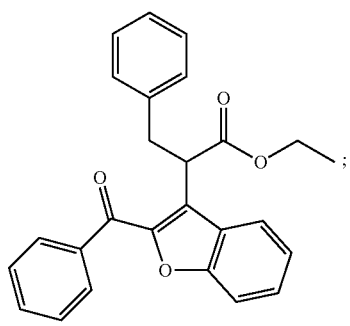 [SMILES: CCOC(=O)C(Cc1ccccc1)c1c(C(=O)c2ccccc2)oc2ccccc12]

methyl 3-(2-benzoylbenzofuran-3-yl)-2-methylpropanoate

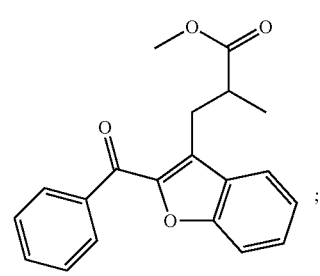 [SMILES: COC(=O)C(C)Cc1c(C(=O)c2ccccc2)oc2ccccc12]

113 butyl 3-(2-benzoylbenzofuran-3-yl)-2-methylpropanoate

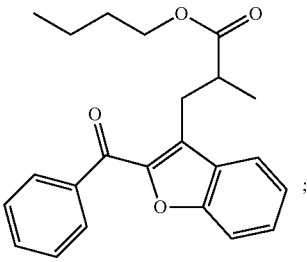 [SMILES: CCCCOC(=O)C(C)Cc1c(C(=O)c2ccccc2)oc2ccccc12]

methyl 2-(2-(4-fluorobenzoyl)benzofuran-3-yl)butanoate (3l)

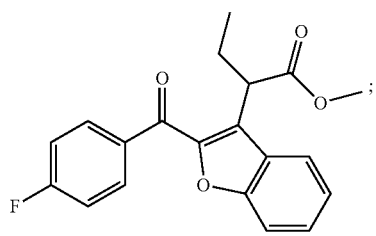 [SMILES: CCC(C(=O)OC)c1c(C(=O)c2ccc(F)cc2)oc2ccccc12]

methyl 2-(2-(4-fluorobenzoyl)benzofuran-3-yl)butanoate

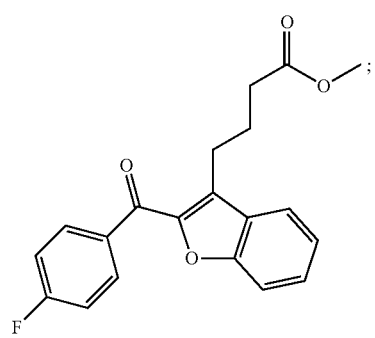 [SMILES: COC(=O)CCCc1c(C(=O)c2ccc(F)cc2)oc2ccccc12]

ethyl 2-(2-(4-fluorobenzoyl)benzofuran-3-yl)propanoate

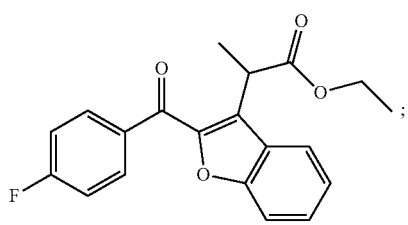 [SMILES: CCOC(=O)C(C)c1c(C(=O)c2ccc(F)cc2)oc2ccccc12]

methyl 2-(2-(4-fluorobenzoyl)benzofuran-3-yl)propanoate

114

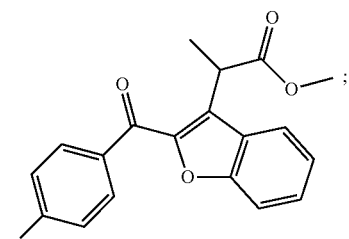

methyl 2-(2-(4-fluorobenzoyl)benzofuran-3-yl)butanoate

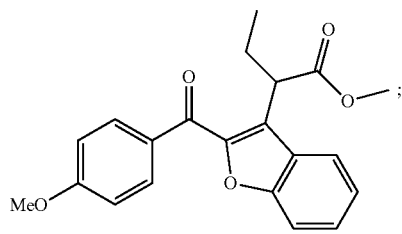 [SMILES: CCC(C(=O)OC)c1c(C(=O)c2ccc(OC)cc2)oc2ccccc12]

methyl 2-(2-(4-fluorobenzoyl)benzofuran-3-yl)butanoate

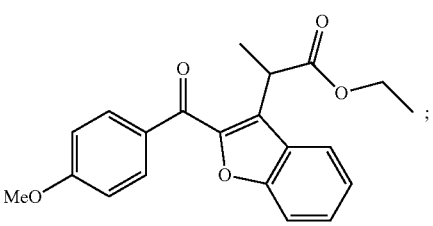 [SMILES: CCOC(=O)C(C)c1c(C(=O)c2ccc(OC)cc2)oc2ccccc12]

methyl 2-(2-(4-methoxybenzoyl)benzofuran-3-yl)propanoate

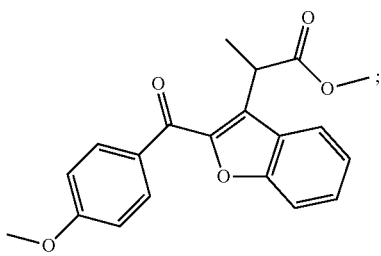

methyl 2-(5-chloro-2-(4-methoxybenzoyl)benzofuran-3-yl)propanoate

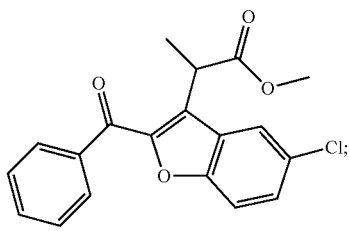 [SMILES: COC(=O)C(C)c1c(C(=O)c2ccccc2)oc2ccc(Cl)cc12]

methyl 2-(5-chloro-2-(4-methoxybenzoyl)benzofuran-3-yl)propanoate

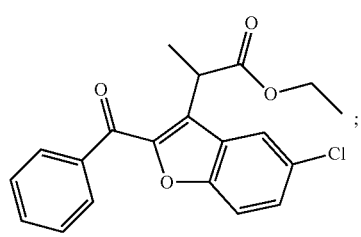 [SMILES: CCOC(=O)C(C)c1c(C(=O)c2ccccc2)oc2ccc(Cl)cc12]

methyl 2-(5-chloro-2-(4-methoxybenzoyl)benzofuran-3-yl)propanoate

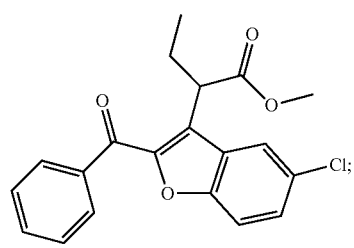 [SMILES: CCC(C(=O)OC)c1c(C(=O)c2ccccc2)oc2ccc(Cl)cc12]

methyl 2-(5-chloro-2-(4-methoxybenzoyl)benzofuran-3-yl)propanoate

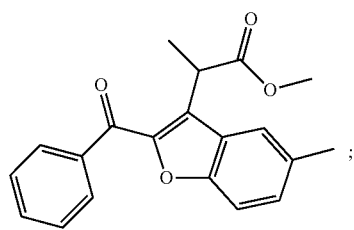 [SMILES: COC(=O)C(C)c1c(C(=O)c2ccccc2)oc2ccc(C)cc12]

methyl 2-(5-chloro-2-(4-methoxybenzoyl)benzofuran-3-yl)propanoate

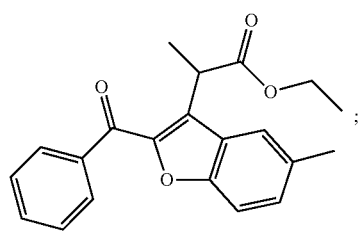

methyl 2-(2-benzoyl-5-methylbenzofuran-3-yl)butanoate

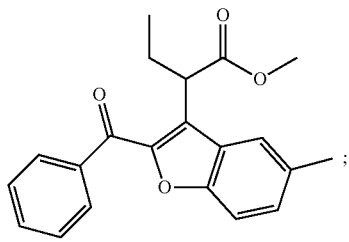 [SMILES: CCC(C(=O)OC)c1c(C(=O)c2ccccc2)oc2ccc(C)cc12]

methyl 2-(2-benzoylbenzofuran-3-yl)propanoate

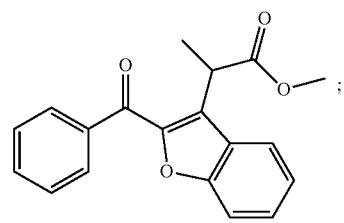 [SMILES: COC(=O)C(C)c1c(C(=O)c2ccccc2)oc2ccccc12]

Ethyl 2-(2-benzoylbenzofuran-3-yl)propanoate

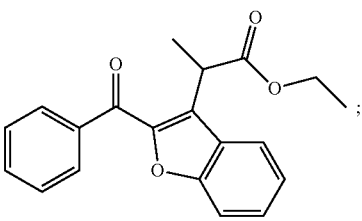 [SMILES: CCOC(=O)C(C)c1c(C(=O)c2ccccc2)oc2ccccc12]

Butyl 2-(2-benzoyl benzofuran-3-yl)propanoate

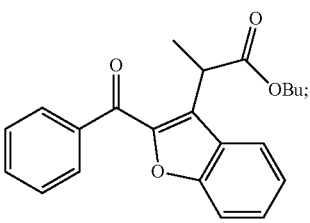

Cyclohexyl 2-(2-benzoylbenzofuran-3-yl)propanoate

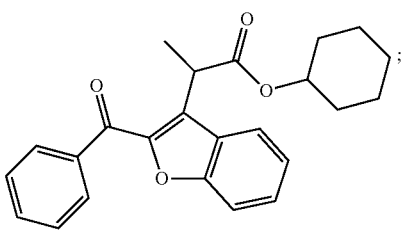 [SMILES: CC(C(=O)OC1CCCCC1)c1c(C(=O)c2ccccc2)oc2ccccc12]

| 117 | 118 |
|---|---|
| Methyl 2-(2-benzoylbenzofuran-3-yl)butanoate | Methyl 2-(2-(4-fluorobenzoyl)benzofuran-3-yl)butanoate |

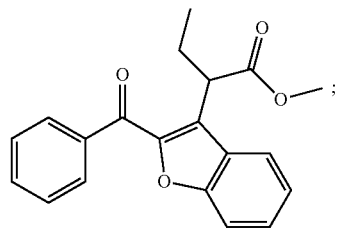 [SMILES: CCC(C(=O)OC)c1c(C(=O)c2ccccc2)oc2ccccc12]

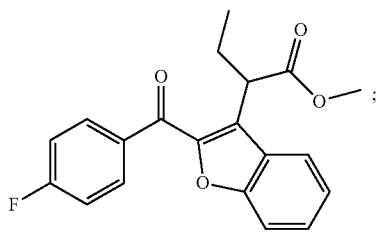

Ethyl 2-(2-benzoylbenzofuran-3-yl)-3-phenylpropanoate

Methyl 2-(2-(4-methoxybenzoyl)benzofuran-3-yl)propanoate

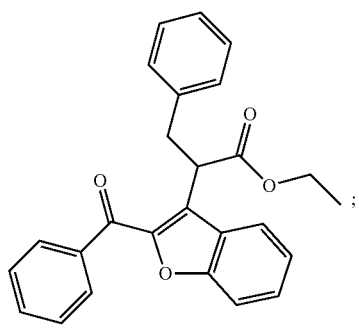 [SMILES: CCOC(=O)C(Cc1ccccc1)c1c(C(=O)c2ccccc2)oc2ccccc12]

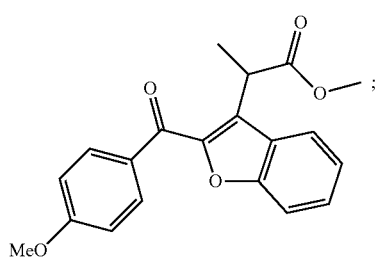 [SMILES: COC(=O)C(C)c1c(C(=O)c2ccc(OC)cc2)oc2ccccc12]

Ethyl 2-(2-(4-methoxybenzoyl)benzofuran-3-yl)propanoate

Methyl 2-(2-(4-fluorobenzoyl)benzofuran-3-yl)propanoate

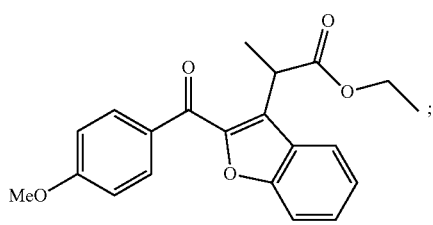 [SMILES: CCOC(=O)C(C)c1c(C(=O)c2ccc(OC)cc2)oc2ccccc12]

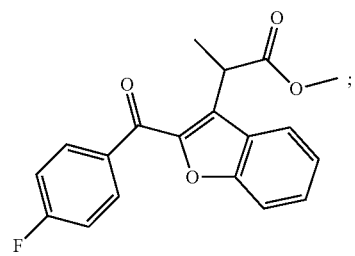

Methyl 2-(2-(4-methoxybenzoyl)benzofuran-3-yl)butanoate

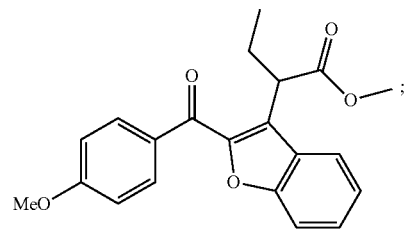 [SMILES: CCC(C(=O)OC)c1c(C(=O)c2ccc(OC)cc2)oc2ccccc12]

Ethyl 2-(2-(4-fluorobenzoyl)benzofuran-3-yl)propanoate

Methyl 2-(2-benzoyl-5-methylbenzofuran-3-yl)propanoate

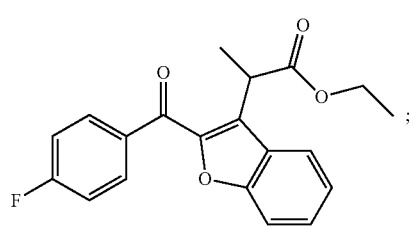

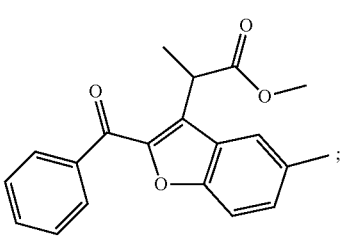 [SMILES: COC(=O)C(C)c1c(C(=O)c2ccccc2)oc2ccc(C)cc12]

Ethyl 2-(2-benzoyl-5-methylbenzofuran-3-yl)propanoate

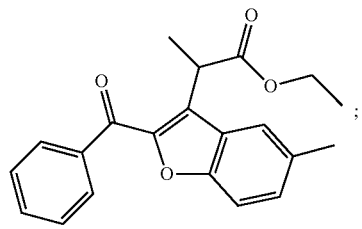 [SMILES: CCOC(=O)C(C)c1c(C(=O)c2ccccc2)oc2ccc(C)cc12]

Methyl 2-(2-benzoyl-5-methylbenzofuran-3-yl)butanoate

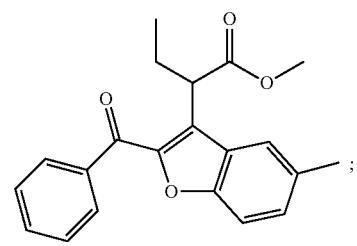 [SMILES: CCC(C(=O)OC)c1c(C(=O)c2ccccc2)oc2ccc(C)cc12]

Methyl 2-(2-benzoyl-5-chlorobenzofuran-3-yl)propanoate

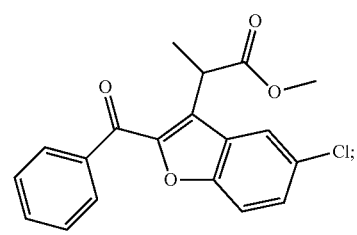 [SMILES: COC(=O)C(C)c1c(C(=O)c2ccccc2)oc2ccc(Cl)cc12]

Ethyl 2-(2-benzoyl-5-chlorobenzofuran-3-yl)propanoate

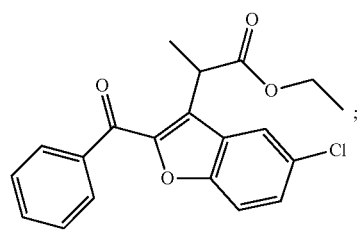 [SMILES: CCOC(=O)C(C)c1c(C(=O)c2ccccc2)oc2ccc(Cl)cc12]

Methyl 2-(2-benzoyl-5-chlorobenzofuran-3-yl)butanoate

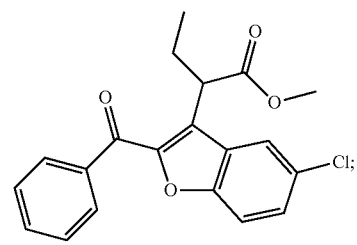 [SMILES: CCC(C(=O)OC)c1c(C(=O)c2ccccc2)oc2ccc(Cl)cc12]

2-(2-benzoylbenzofuran-3-yl)-N-isopropylpropanamide

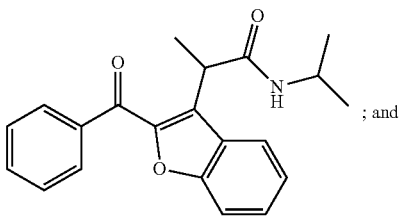 [SMILES: CC(C)NC(=O)C(C)c1c(C(=O)c2ccccc2)oc2ccccc12]; and (3-phenethylbenzofuran-2-yl)(phenyl)methanone

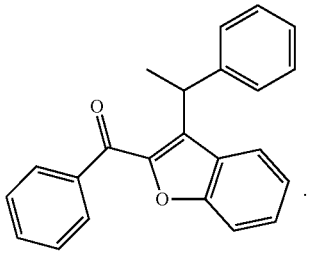 [SMILES: CC(c1ccccc1)c1c(C(=O)c2ccccc2)oc2ccccc12].

14. The process of claim 12, further comprising adding an alkene.

15. The process according to claim 14, wherein the alkene is of formula:

wherein, $R_{2'}$ is selected from group consisting of aryl, $(C_1\text{-}C_6)$ alkyl substituted acetamide, and branched or linear $(C_1\text{-}C_{12})$ alkyl.

16. The process according to claim 1, comprising the steps of:
  a. adding a 2-aroylbenzofuran, an acrylate and dioxane to a reaction vessel containing a mixture of [Ru(p-cymene)Cl$_2$]$_2$, PPh$_3$ and NaHCO$_3$ under argon atmosphere to get a solution mixture;
  b. stirring said solution mixture at a temperature of 130 to 150° C., for a time in the range of 30 to 40 hrs followed by cooling the solution mixture to form a first product, and purifying said first product via column chromatography to obtain a pure linear alkylated aroylbenzofuran compound of formula:

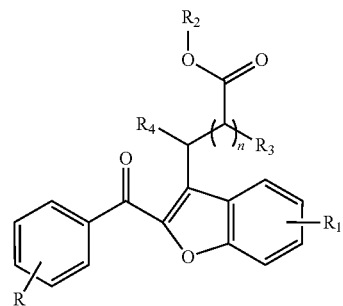

wherein n is an integer ranging from 1 to 6; and R, $R_1$, $R_2$, $R_3$, and $R_4$ are as above.

17. The process according to claim 16, wherein said pure linear alkylated aroylbenzofuran compound is selected from the group consisting of:

ethyl 2-(2-(4-fluorobenzoyl)benzofuran-3-yl)propanoate

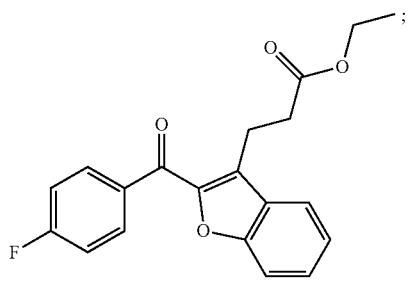 [SMILES: CCOC(=O)CCc1c(C(=O)c2ccc(F)cc2)oc2ccccc12]

methyl 2-(2-(4-fluorobenzoyl)benzofuran-3-yl)propanoate

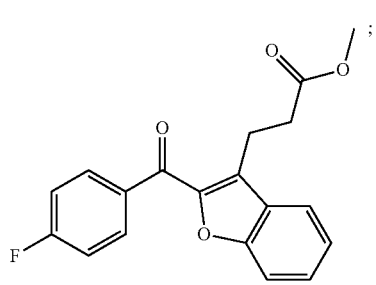 [SMILES: COC(=O)CCc1c(C(=O)c2ccc(F)cc2)oc2ccccc12]

Methyl 3-(2-benzoylbenzofuran-3-yl)propanoate

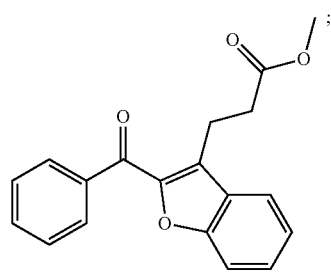 [SMILES: COC(=O)CCc1c(C(=O)c2ccccc2)oc2ccccc12]

Ethyl 3-(2-benzoylbenzofuran-3-yl)propanoate

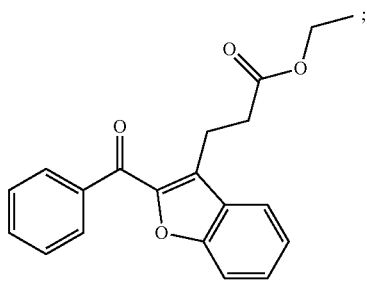 [SMILES: CCOC(=O)CCc1c(C(=O)c2ccccc2)oc2ccccc12]

Butyl 3-(2-benzoylbenzofuran-3-yl)propanoate

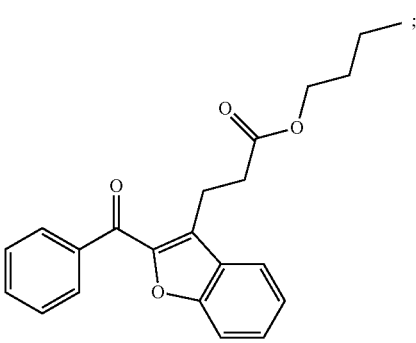 [SMILES: CCCCOC(=O)CCc1c(C(=O)c2ccccc2)oc2ccccc12]

Methyl 3-(2-(4-methoxybenzoyl)benzofuran-3-yl)propanoate

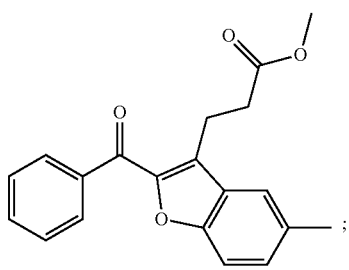 [SMILES: COC(=O)CCc1c(C(=O)c2ccccc2)oc2ccc(C)cc12]

Ethyl 3-(2-(4-methoxybenzoyl)benzofuran-3-yl)propanoate

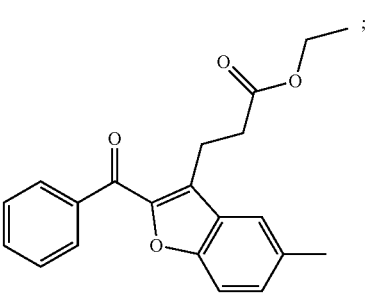 [SMILES: CCOC(=O)CCc1c(C(=O)c2ccccc2)oc2ccc(C)cc12]

Methyl 3-(2-benzoyl-5-chlorobenzofuran-3-yl)propanoate

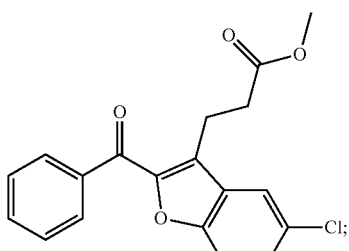

123

Ethyl 3-(2-benzoyl-5-chlorobenzofuran-3-yl)propanoate

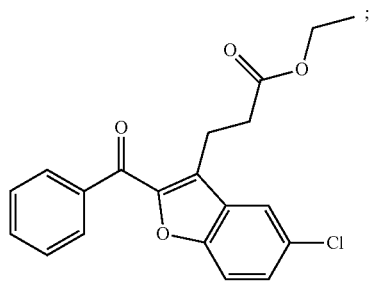 [SMILES: CCOC(=O)CCc1c(C(=O)c2ccccc2)oc2ccc(Cl)cc12]

Methyl 3-(2-(4-methoxybenzoyl)benzofuran-3-yl)propanoate

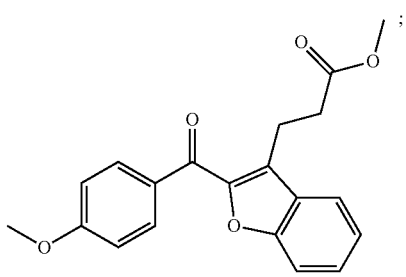

Ethyl 3-(2-(4-methoxybenzoyl)benzofuran-3-yl)propanoate

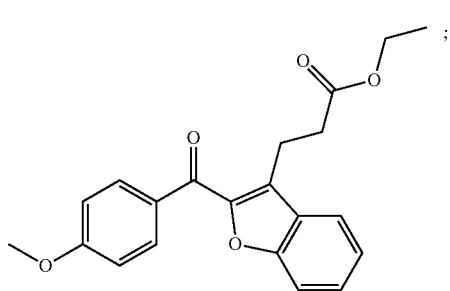 [SMILES: CCOC(=O)CCc1c(C(=O)c2ccc(OC)cc2)oc2ccccc12]

Methyl 3-(2-benzoylbenzofuran-3-yl)-2-methylpropanoate

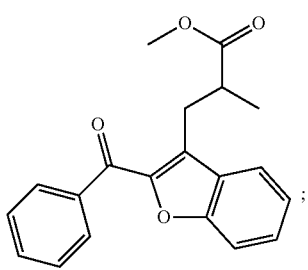 [SMILES: COC(=O)C(C)Cc1c(C(=O)c2ccccc2)oc2ccccc12]

124

Butyl 3-(2-benzoylbenzofuran-3-yl)-2-methylpropanoate

Methyl 3-(2-benzoylbenzofuran-3-yl)propanoate

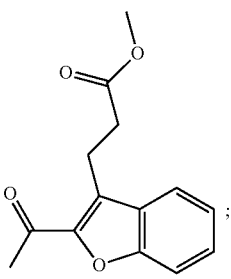 [SMILES: COC(=O)CCc1c(C(C)=O)oc2ccccc12]

(phenyl(3-(1-phenylethyl)benzofuran-2-yl)methanone

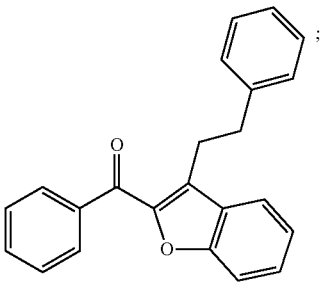 [SMILES: O=C(c1ccccc1)c1oc2ccccc2c1CCc1ccccc1]

Phenyl(3-undecylbenzofuran-2-yl)methanone

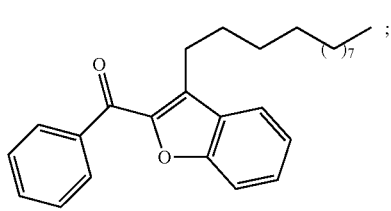

125

Methyl 3-(2-benzoylbenzofuran-3-yl)propanoate

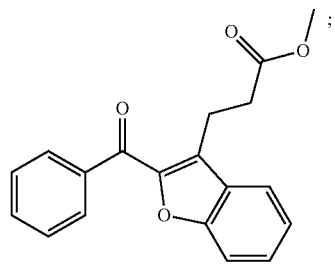 [SMILES: COC(=O)CCc1c(C(=O)c2ccccc2)oc2ccccc12]

Ethyl 3-(2-benzoylbenzofuran-3-yl)propanoate

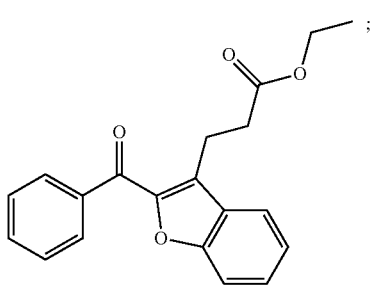 [SMILES: CCOC(=O)CCc1c(C(=O)c2ccccc2)oc2ccccc12]

Butyl 3-(2-benzoylbenzofuran-3-yl)propanoate

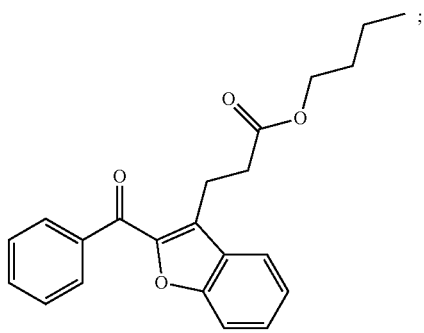 [SMILES: CCCCOC(=O)CCc1c(C(=O)c2ccccc2)oc2ccccc12]

Methyl 3-(2-(4-fluorobenzoyl)benzofuran-3-yl)propanoate

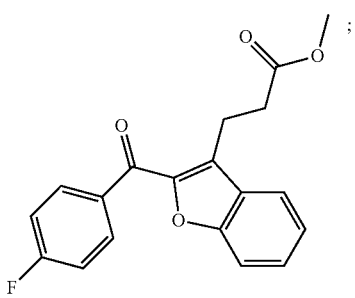 [SMILES: COC(=O)CCc1c(C(=O)c2ccc(F)cc2)oc2ccccc12]

126

Ethyl 3-(2-(4-fluorobenzoyl)benzofuran-3-yl)propanoate

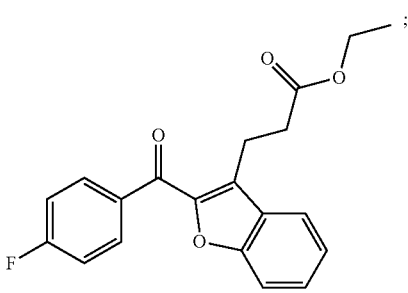 [SMILES: CCOC(=O)CCc1c(C(=O)c2ccc(F)cc2)oc2ccccc12]

Methyl 3-(2-(4-methoxybenzoyl)benzofuran-3-yl)propanoate

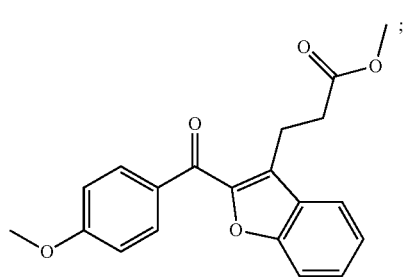

Ethyl 3-(2-(4-methoxybenzoyl)benzofuran-3-yl)propanoate

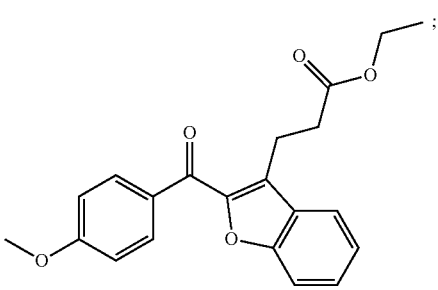 [SMILES: CCOC(=O)CCc1c(C(=O)c2ccc(OC)cc2)oc2ccccc12]

Methyl 3-(2-benzoyl-5-methylbenzofuran-3-yl)propanoate

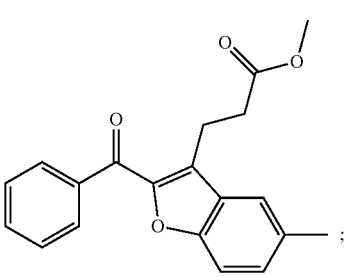 [SMILES: COC(=O)CCc1c(C(=O)c2ccccc2)oc2ccc(C)cc12]

127

Ethyl 3-(2-benzoyl-5-methylbenzofuran-3-yl)propanoate

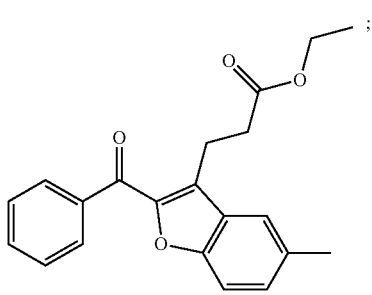 [SMILES: CCOC(=O)CCc1c(C(=O)c2ccccc2)oc2ccc(C)cc12]

Methyl 3-(2-benzoyl-5-chlorobenzofuran-3-yl)propanoate

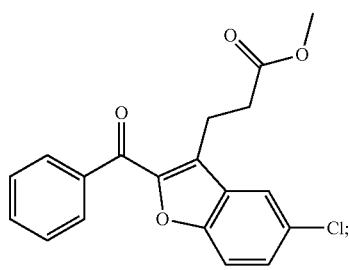 [SMILES: COC(=O)CCc1c(C(=O)c2ccccc2)oc2ccc(Cl)cc12]

Ethyl 3-(2-benzoyl-5-chlorobenzofuran-3-yl)propanoate

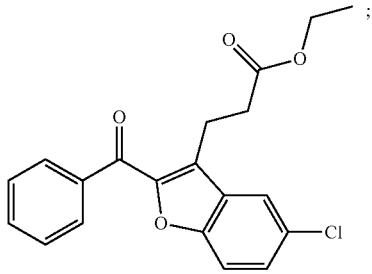 [SMILES: CCOC(=O)CCc1c(C(=O)c2ccccc2)oc2ccc(Cl)cc12]

Methyl 4-(2-benzoylbenzofuran-3-yl)butanoate

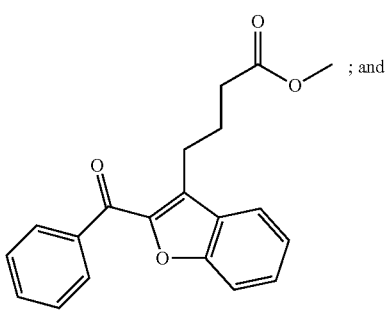 [SMILES: COC(=O)CCCc1c(C(=O)c2ccccc2)oc2ccccc12]

128

Methyl 4-(2-(4-fluorobenzoyl)benzofuran-3-yl)butanoate

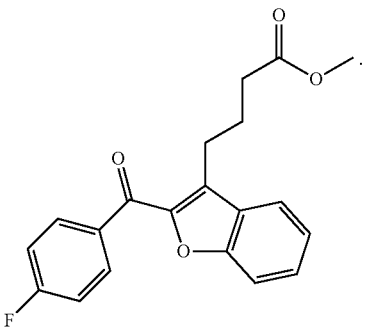 [SMILES: COC(=O)CCCc1c(C(=O)c2ccc(F)cc2)oc2ccccc12]

18. The process according to claim 1, comprising:
a. adding a 3-aroylbenzofuran, said acrylate $K_2CO_3$ and toluene to a reaction vessel containing a mixture of [Ru(PPh$_3$)$_3$Cl$_2$], AgOAc under argon atmosphere to get a solution mixture;
b. stirring the solution mixture at a temperature of from 130 to 150° C., for a time of 20 to 30 hrs followed by cooling the solution mixture to form a first product, purifying said first product via column chromatography to obtain a pure linear and branched alkylated benzofuran compound of formula;

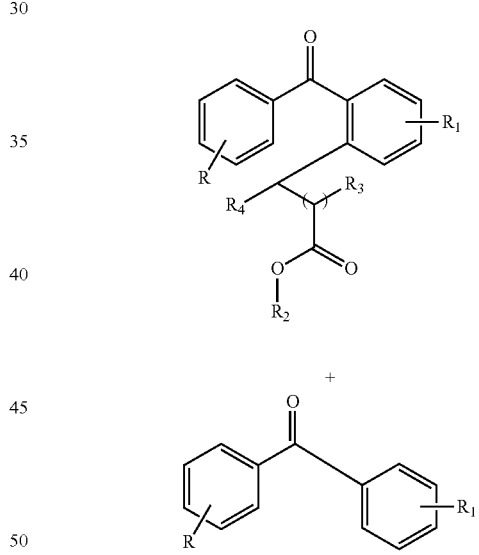

or mixtures thereof,
wherein n is an integer ranging from 1 to 6; and
R, $R_1$, $R_2$, $R_3$, and $R_4$ are as above.

19. The process according to claim 18, wherein said acrylate is selected from the group consisting of linear or branched ($C_1$-$C_6$)alkyl, a cyclo ($C_4$-$C_8$)alkyl, ($C_1$-$C_6$)alkyl methacrylate, a linear or branched ($C_1$-$C_6$) alkyl crotonate, and a substituted or unsubstituted acrylamide.

20. The process according to claim 19, wherein said acrylate is selected from the group consisting of methyl, ethyl, terbutyl, cyclohexyl acrylate, methyl methacrylate, methyl crotonate, and N-isopropylacrylamide.

21. The process according to claim 17, wherein said 3-aroylbenzofuran compound is selected from group consisting of:

Methyl 3-(3-benzoyl-5-methoxybenzofuran-2-yl)propanoate

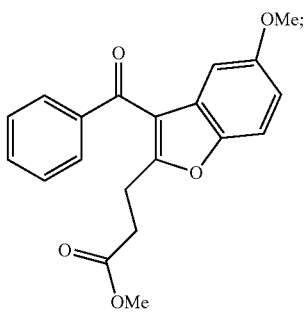 [SMILES: COC(=O)CCc1oc2ccc(OC)cc2c1C(=O)c1ccccc1]

Ethyl 3-(3-benzoyl-5-methoxybenzofuran-2-yl)propanoate

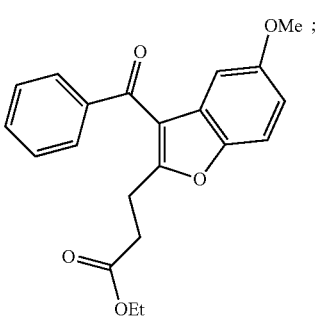 [SMILES: CCOC(=O)CCc1oc2ccc(OC)cc2c1C(=O)c1ccccc1]

Tert-butyl 3-(3-benzoyl-5-methoxybenzofuran-2-yl)propanoate

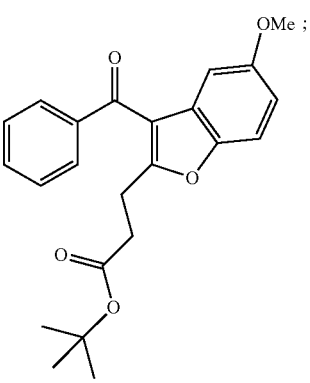 [SMILES: COc1ccc2oc(CCC(=O)OC(C)(C)C)c(C(=O)c3ccccc3)c2c1]

Methyl 3-(3-benzoyl-5-methoxybenzofuran-2-yl)-2-methylpropanoate

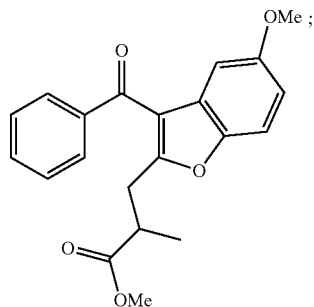 [SMILES: COC(=O)C(C)Cc1oc2ccc(OC)cc2c1C(=O)c1ccccc1]

Cyclohexyl 3-(3-benzoyl-5-methoxybenzofuran-2-yl) propanoate

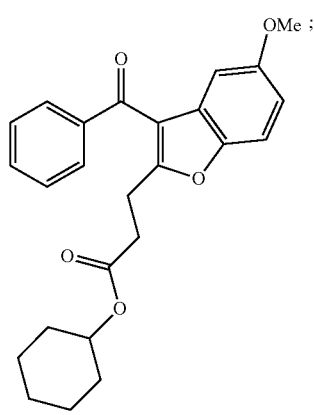 [SMILES: COc1ccc2oc(CCC(=O)OC3CCCCC3)c(C(=O)c3ccccc3)c2c1]

Methyl 2-(3-benzoyl-5-methoxybenzofuran-2-yl)butanoate

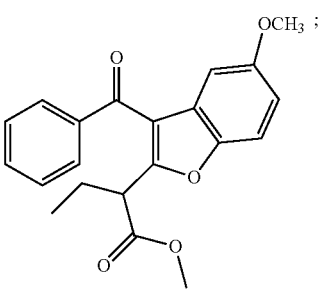 [SMILES: CCC(C(=O)OC)c1oc2ccc(OC)cc2c1C(=O)c1ccccc1]

Methyl 4-(3-benzoyl-5-methoxybenzofuran-2-yl)butanoate

131
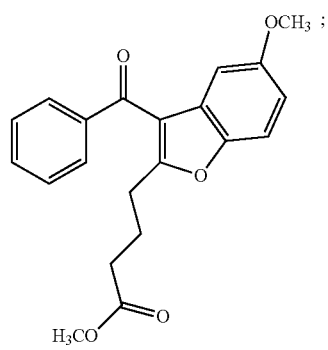 [SMILES: COC(=O)CCCc1oc2ccc(OC)cc2c1C(=O)c1ccccc1]
2-(3-benzoyl-5-methoxybenzofuran-2-yl)-N-isopropyl-propanamide
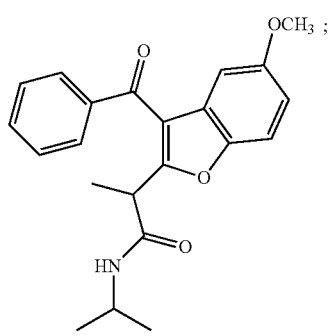 [SMILES: COc1ccc2oc(C(C)C(=O)NC(C)C)c(C(=O)c3ccccc3)c2c1]
3-(3-benzoyl-5-methoxybenzofuran-2-yl)-N-isopropyl-propanamide
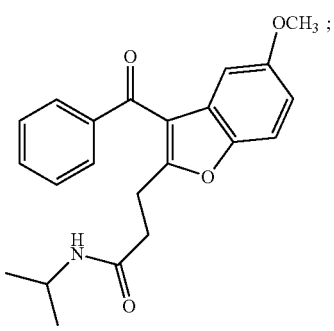 [SMILES: COc1ccc2oc(CCC(=O)NC(C)C)c(C(=O)c3ccccc3)c2c1]
Tert-butyl 3-(5-methoxy-3-(4-methoxybenzoyl)benzofuran-2-yl)propanoate
132
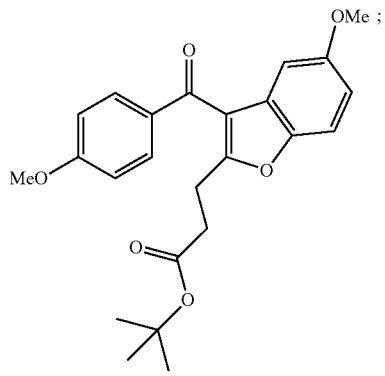 [SMILES: COc1ccc(C(=O)c2c(CCC(=O)OC(C)(C)C)oc3ccc(OC)cc23)cc1]
Methyl 3-(5-methoxy-3-(4-methoxybenzoyl)benzofuran-2-yl)-2-methylpropanoate
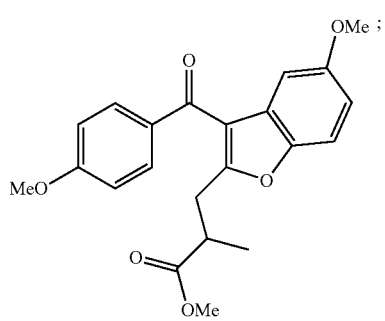 [SMILES: COC(=O)C(C)Cc1oc2ccc(OC)cc2c1C(=O)c1ccc(OC)cc1]
Methyl 4-(5-methoxy-3-(4-methoxybenzoyl)benzofuran-2-yl)butanoate
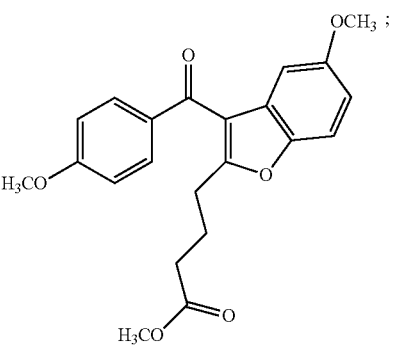 [SMILES: COC(=O)CCCc1oc2ccc(OC)cc2c1C(=O)c1ccc(OC)cc1]
Tert-butyl 3-(3-(4-bromobenzoyl)-5-methoxybenzofuran-2-yl)propanoate

133

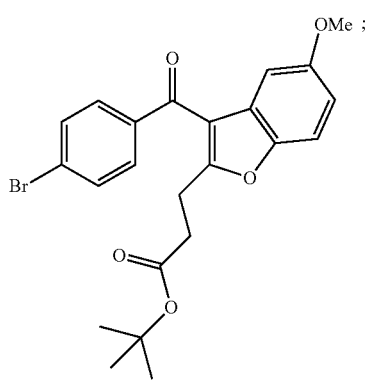 [SMILES: COc1ccc2oc(CCC(=O)OC(C)(C)C)c(C(=O)c3ccc(Br)cc3)c2c1]

Methyl 3-(3-(4-bromobenzoyl)-5-methoxybenzofuran-2-yl)-2-methylpropanoate

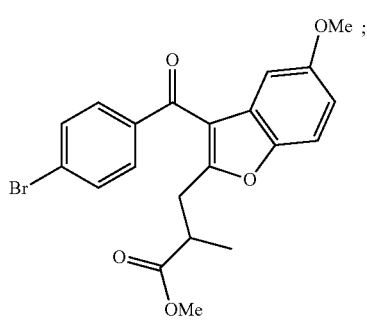 [SMILES: COC(=O)C(C)Cc1oc2ccc(OC)cc2c1C(=O)c1ccc(Br)cc1]

Methyl 4-(3-(4-bromobenzoyl)-5-methoxybenzofuran-2-yl)butanoate

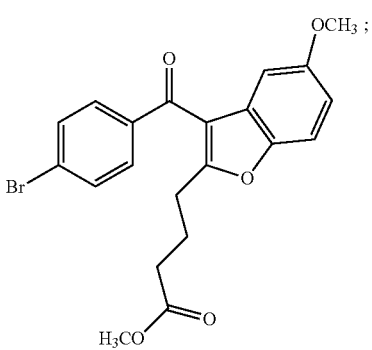 [SMILES: COC(=O)CCCc1oc2ccc(OC)cc2c1C(=O)c1ccc(Br)cc1]

Tert-butyl 3-(3-benzoyl-5-methoxynaphtho[1,2-b]furan-2-yl)propanoate

134

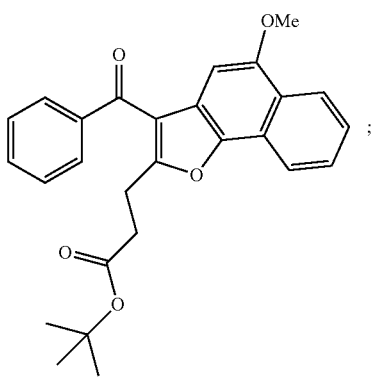 [SMILES: COc1cc2c(C(=O)c3ccccc3)c(CCC(=O)OC(C)(C)C)oc2c2ccccc12]

Methyl 3-(3-benzoyl-5-methoxynaphtho[1,2-b]furan-2-yl)-2-methylpropanoate

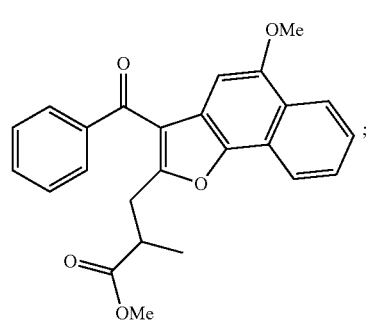 [SMILES: COC(=O)C(C)Cc1oc2c(cc(OC)c3ccccc32)c1C(=O)c1ccccc1]

Tert-butyl 3-(3-benzoyl-4,6-dibromo-5-methoxybenzofuran-2-yl)propanoate

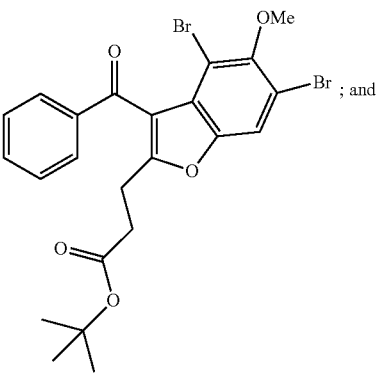 [SMILES: COc1c(Br)cc2oc(CCC(=O)OC(C)(C)C)c(C(=O)c3ccccc3)c2c1Br]

Methyl 3-(3-benzoyl-4,6-dibromo-5-methoxybenzofuran-2-yl)-2-methylpropanoate

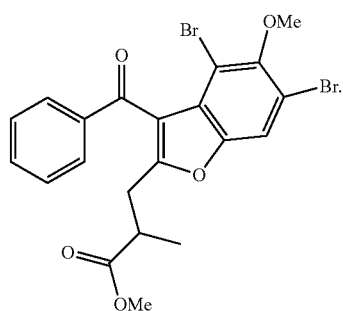 [SMILES: COC(=O)C(C)Cc1oc2cc(Br)c(OC)c(Br)c2c1C(=O)c1ccccc1]

22. The process according to claim 17, wherein said branched C2-alkylated 3-aroylbenzofuran compound is selected from group consisting of:

Methyl 2-(5-methoxy-3-(4-methoxybenzoyl)benzofuran-2-yl)butanoate

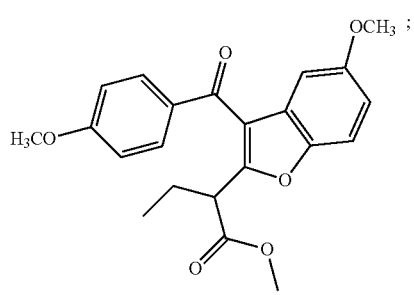 [SMILES: CCC(C(=O)OC)c1oc2ccc(OC)cc2c1C(=O)c1ccc(OC)cc1]

Methyl 2-(3-benzoyl-5-methoxybenzofuran-2-yl)butanoate

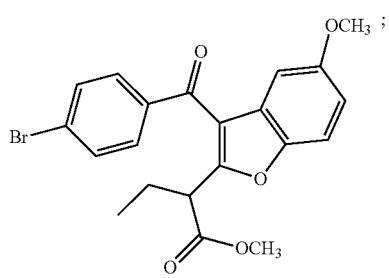 [SMILES: CCC(C(=O)OC)c1oc2ccc(OC)cc2c1C(=O)c1ccc(Br)cc1]

Methyl 2-(3-benzoyl-5-methoxynaphtho[1,2-b]furan-2-yl)butanoate

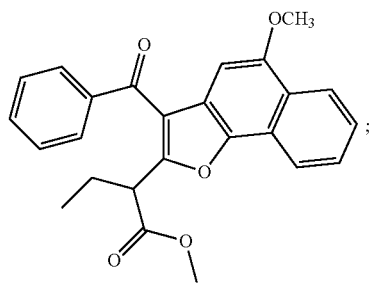 [SMILES: CCC(C(=O)OC)c1oc2c(cc(OC)c3ccccc32)c1C(=O)c1ccccc1]

Methyl 2-(3-benzoyl-4,6-dibromo-5-methoxybenzofuran-2-yl) butanoate

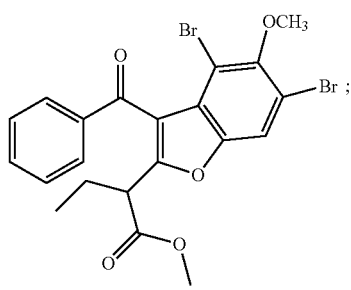 [SMILES: CCC(C(=O)OC)c1oc2cc(Br)c(OC)c(Br)c2c1C(=O)c1ccccc1]

N-isopropyl-2-(5-methoxy-3-(4-methoxybenzoyl)benzofuran-2-yl)propanamide

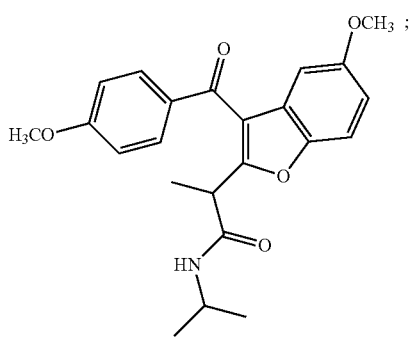 [SMILES: COc1ccc(C(=O)c2c(C(C)C(=O)NC(C)C)oc3ccc(OC)cc23)cc1]

N-isopropyl-3-(5-methoxy-3-(4-methoxybenzoyl)benzofuran-2-yl)propanamide

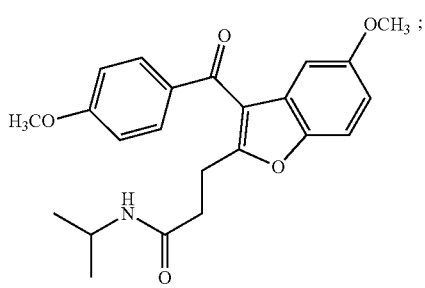 [SMILES: COc1ccc(C(=O)c2c(CCC(=O)NC(C)C)oc3ccc(OC)cc23)cc1]

2-(3-(4-bromobenzoyl)-5-methoxybenzofuran-2-yl)-N-isopropylpropanamide

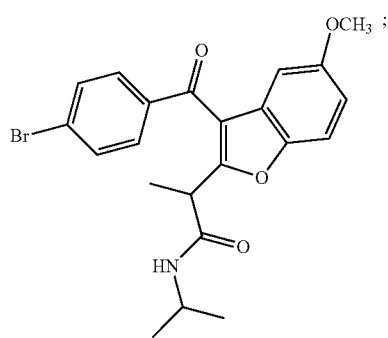 [SMILES: COc1ccc2oc(C(C)C(=O)NC(C)C)c(C(=O)c3ccc(Br)cc3)c2c1]

3-(3-(4-bromobenzoyl)-5-methoxybenzofuran-2-yl)-N-isopropylpropanamide

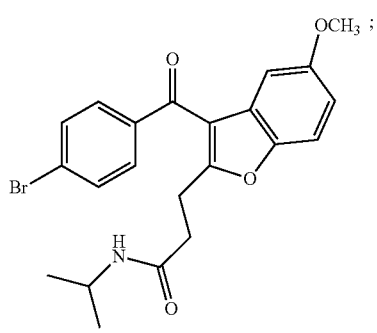 [SMILES: COc1ccc2oc(CCC(=O)NC(C)C)c(C(=O)c3ccc(Br)cc3)c2c1]
2-(3-benzoyl-5-methoxynaphtho[1,2-b]furan-2-yl)-N-isopropylpropanamide
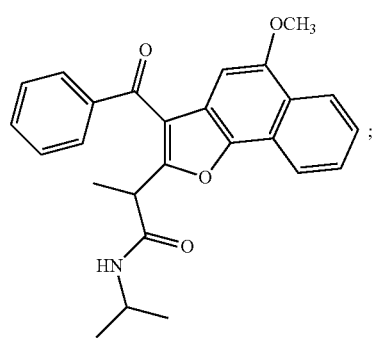 [SMILES: COc1cc2c(C(=O)c3ccccc3)c(C(C)C(=O)NC(C)C)oc2c2ccccc12]
3-(3-benzoyl-5-methoxynaphtho[1,2-b]furan-2-yl)-N-isopropylpropanamide
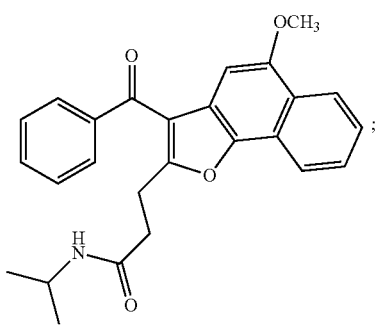 [SMILES: COc1cc2c(C(=O)c3ccccc3)c(CCC(=O)NC(C)C)oc2c2ccccc12]
2-(3-benzoyl-5-methoxybenzofuran-2-yl)-N-isopropylpropanamide
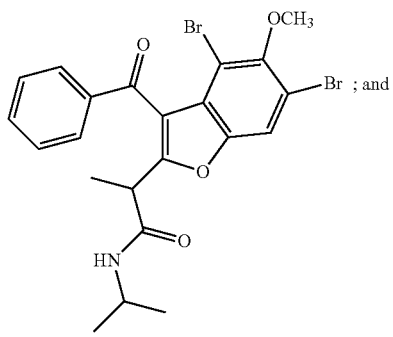 [SMILES: COc1c(Br)cc2oc(C(C)C(=O)NC(C)C)c(C(=O)c3ccccc3)c2c1Br]
3-(3-benzoyl-4,6-dibromo-5-methoxybenzofuran-2-yl)-N-isopropylpropanamide
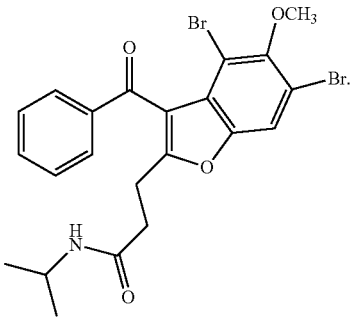 [SMILES: COc1c(Br)cc2oc(CCC(=O)NC(C)C)c(C(=O)c3ccccc3)c2c1Br]
\* \* \* \* \*